(12) United States Patent
Baker et al.

(10) Patent No.: US 8,669,376 B2
(45) Date of Patent: Mar. 11, 2014

(54) CYTOTOXIN COMPOUNDS AND METHODS OF ISOLATION

(75) Inventors: Bill Baker, Tampa, FL (US); Thushara Diyabalanage, Tampa, FL (US); James B. McClintock, Birmingham, AL (US); Charles D. Amsler, Pelham, AL (US)

(73) Assignees: University of South Florida, Tampa, FL (US); The UAB Research Foundation, Birmingham, AL (US)

( * ) Notice: Subject to any disclaimer, the term of this patent is extended or adjusted under 35 U.S.C. 154(b) by 1185 days.

(21) Appl. No.: 12/066,938

(22) PCT Filed: Sep. 18, 2006

(86) PCT No.: PCT/US2006/036484
§ 371 (c)(1),
(2), (4) Date: Aug. 28, 2008

(87) PCT Pub. No.: WO2007/035734
PCT Pub. Date: Mar. 29, 2007

(65) Prior Publication Data
US 2009/0192215 A1    Jul. 30, 2009

Related U.S. Application Data

(63) Continuation-in-part of application No. 10/906,386, filed on Feb. 17, 2005, now Pat. No. 7,625,885.

(60) Provisional application No. 60/717,598, filed on Sep. 16, 2005, provisional application No. 60/521,073, filed on Feb. 17, 2004.

(51) Int. Cl.
*C07D 313/00* (2006.01)
*C12N 9/99* (2006.01)
*A61K 31/335* (2006.01)
*A61P 35/00* (2006.01)

(52) U.S. Cl.
USPC .......................... 549/271; 514/450; 435/184

(58) Field of Classification Search
USPC .......................... 514/450; 549/271; 435/184
See application file for complete search history.

(56) References Cited

U.S. PATENT DOCUMENTS 5,324,739 A  6/1994  Gerwick et al.
5,405,859 A  4/1995  Ireland
(Continued)

FOREIGN PATENT DOCUMENTS

WO    WO 01/02413       1/2001
WO    WO 2005/063748 A1  7/2005

OTHER PUBLICATIONS

Morissette et al. "High-throughput crystallization: polymorphs, salts, co-crystals and solvates of pharmaceutical solids" Advanced Drug Delivery Reviews, 2004, 56, 275-300.*

(Continued)

*Primary Examiner* — Kortney L Klinkel
(74) *Attorney, Agent, or Firm* — Saliwanchik, Lloyd & Eisenschenk

(57) ABSTRACT

The present invention concerns groups of compounds derived from tunicates of the *Synoicum* species, as well as to pharmaceutical compositions comprising these compounds, and uses thereof. Extracts from tunicates show selective toxicity against several different cancer cell lines in the NCI 60 cell line panel. These compounds are useful in the effective treatment of cancers, particularly malignant melanomas, colon cancer, and renal cancer cell lines.

54 Claims, 24 Drawing Sheets

(56) References Cited

U.S. PATENT DOCUMENTS

| | | | |
|---|---|---|---|
| 5,626,860 | A | 5/1997 | Cincotta et al. |
| 6,548,485 | B2 | 4/2003 | Khosla et al. |
| 6,750,247 | B2 | 6/2004 | Crews et al. |
| 6,960,648 | B2 | 11/2005 | Bonny |
| 7,151,116 | B2 | 12/2006 | Wender et al. |
| 2003/0032594 | A1 | 2/2003 | Bonny |
| 2005/0187286 | A1 | 8/2005 | Baker et al. |

OTHER PUBLICATIONS

Seddon et al. "Pseudopolymorph: A Polemic" Crystal Growth and Design, 2004, 4, 1087.*
Vippagunta et al. "Crystalline solids" Advanced Drug Delivery Reviews, 2001, 48, 3-26.*
Braga et al. "Making crystals from crystals: a green route to crystal engineering and polymorphism" Chem. Commun. 2005, 3635-3645.*
Carroll, A.R. et al. "Prunolides A, B, and C: Novel tetraphenolic Bis-spiroketals from the Australian ascidian *Synoicum prunum*" *J. Org. Chem.*, 1999, 64:2680-2682.
Ortega, M.J. et al. "New rubrolides from the ascidian *Synoicum blochmanni*" *Tetrahedron*, 2000, 56:3963-3967.
Amundson, S.A. et al. "An Informatics Approach Identifying Markers of Chemosensitivity in Human Cancer Cell Lines" *Cancer Res.*, 2000, pp. 6101-6110, vol. 60.
Ankisetty, S. et al. "Chemical Investigation of Predator-Deterred Macroalgae from the Antarctic Peninsula" *J. Nat. Prod.*, 2004, pp. 1295-1302, vol. 67.
Arts, J. et al. "Histone Deacetylase Inhibitors: From Chromatin Remodeling to Experimental Cancer Therapeutics" *Curr. Med. Chem.*, 2003, pp. 2343-2350, vol. 10.
Aue, W.P. et al. "Two-Dimensional Spectroscopy. Application to Nuclear Magnetic Resonance" *J. Chem. Phys.*, 1976, pp. 2229-2246, vol. 64, No. 5.
Balimane, P.V. et al. "Current Industrial Practices of Assessing Permeability and P-Glycoprotein Interaction" *AAPS J.*, 2006, pp. E1-13, vol. 8(1), Article 1 (http://www.aapsj.org).
Bax, A. et al. "Natural Abundance $^{13}C$—$^{13}C$ Coupling Observed via Double-Quantum Coherence" *J. Am. Chem. Soc.*, 1980, pp. 4849-4851, vol. 102.
Bax, A. et al "$^{1}H$ and $^{13}C$ Assignments from Sensitivity-Enhanced Detection of Heteronuclear Multiple-Bond Connectivity by 2D Multiple Quantum NMR" *J. Am. Chem. Soc.*, 1986b, pp. 2093-2096, vol. 108.
Bax, A. et al, "Improved Resolution and Sensitivity in $^{1}H$-Dectected Heteronuclear Multiple-Bond Correlation Spectroscopy" *J Magnetic Resonance*, 1988, pp. 186-191, vol. 78.
Beutler, J.A. et al. "Novel Marine and Microbial Natural Product Inhibitors of Vacuolar ATPase" *Curr. Med. Chem*, 2003, pp. 787-796, vol. 10.
Bodenhausen, G. et al. "Natural Abundance Nitrogen-15 NMR by Enhanced Heteronuclear Spectroscopy" *Chem. Phys. Lett.*, 1980, pp. 185-189, vol. 69, Issue 1. Abstract.
Bowden, K. et al. "Researches on Acetylenic Compounds. Part I. The Preparation of Acetylenic Ketones by Oxidation of Acetylenic Carbinols and Glycols" *J. Chem. Soc.*, 1980, pp. 39-45.
Bowman, E.J. et al. "Identification of a New Chondropsin Class of Antitumor Compound That Selectively Inhibits V—ATPases" *J. Biol. Chem.*, 2003, pp. 44147-44152, vol. 278, No. 45.
Bowman, E.J. et al. "The Bafilomycin/Concanamycin Binding Site in Subunit c of the V—ATPases from *Neurospora crassa* and *Saccharomyces cerevisiae*" *J. Biol. Chem.*, 2004, pp. 33131-33138, vol. 279, No. 32.
Boyd, M.R. et al. "Discovery of a Novel Antitumor Benzolactone Enamide Class That Selectively Inhibits Mammalian Vacuolar-Type ($H^{+}$)-ATPases" *J. Pharmacol. Exp. Ther.* pp. 114-120, vol. 297, No. 1, 2001.
Braunschweiler, L. et al. "Coherence Transfer by Isotropic Mixing: Application to Proton Correlation Spectroscopy" *J. Mag. Res.*, 1983, pp. 521-528, vol. 53.

Brunner, H. et al. "Synthesis of New Optically Active Bis- and Tris(phosphines)" *Synthesis*, 1989, pp. 706-709. Abstract.
Chene, P. "The ATPases: A New Family for a Family-Based Drug Design Approach" *Expert Opin. Thera. Tar.*, 2003, pp. 453-461, vol. 7, No. 3. Abstract.
Choi, J. et al. "An Excellent Nickel Boride Catalyst for the Selective Hydrogenation of Olefins," *Synthesis* 1996, pp. 597-599. Abstract.
Coe, J.W. et al. "Studies of an Intramolecular Diels-Adler Approach to the Nargenicins; Involvement of Boatlike Transition States in the Cyclizations of Substituted 1, 7, 9-Decatrien-3-ones[1]" *J. Org. Chem.*, 1989, pp. 915-930, vol. 54.
Corey, E.J. et al. "Protection of Hydroxyl Groups as *tert*-Butyldimethylsityl Derivatives" *J. Am. Chem. Soc.*, 1972, pp. 6190-6191, vol. 94. No. 17.
Cunico, R.F. et al. "The Triisopropylsilyl Group as a Hydroxyl-Protecting Function" *J. Org. Chem.*, 1980, pp. 4797-4798, vol. 45.
Dess, D.B. et al. "Readily Accessible 12-I-5[1] Oxidant for the Conversion of Primary and Secondary Alcohols to Aldehydes and Ketones" *J. Org. Chem.*, 1983, pp. 4155-4156, vol. 48.
Dess, D.B. et al. "A Useful 12-I-5 Triacetoxyperiodinane (the Dess-Martin Periodinane) for the Selective Oxidation of Primary or Secondary Alcohols and a Variety of Related 12-I-5 Species" *J. Am. Chem. Soc.*, 1991, pp. 7277-7287, vol. 113.
Di Grandi, M.J. et al. "Synthesis of Competent Nucleophiles for Delivering the A Ring of Taxol" *J. Org. Chem.*, 1993, pp. 4989-4992, vol. 58.
Diyabalanage, T. et al. Palmerolide A, a Cytotoxic Macrolide from the Antarctic Tunicate *Synoicum adareanum*. *J. Am. Chem. Soc.*, 2006, pp. 5630-5631, vol. 128.
Dolder, M. et al. "Synthetic Studies Directed Toward the Pseurotins. Part I. Synthesis of Related Furan-3(2H)-ones" *Helv. Chem. Acta*, 1990, pp. 63-68, vol. 73, No. 1. Abstract.
Duggan, M.E. et al. "Copper(I) Chloride Catalyzed Addition of Alcohols to Alkyl Isocyanates. A Mild and Expedient Method for Alkyl Carbamate Formation" *Synthesis*, 1989, pp. 131-132. Abstract.
Eaton, J.T. et al. "Hydrolysis in the Absence of Bulk Water 1. Chemoselective Hydrolysis of Amides using Tetrahalophthalic Anhydrides" *Tetrahedron Lett.*, 1988, pp. 6553-6556, vol. 29, Issue 50. Abstract.
Erickson, K.L. et al. "*Salicylihalainides* A and B, Novel Cytotoxic Macrolides from the Marine Sponge *Haliclona* sp." *J. Org. Chem.*, 1997, pp. 8188-8192, vol. 62.
Evans, D.A. et al. "Enantioselective Aldol Condensations. 2. Erythro-Selective Chiral Aldol Condensations via Boron Enolates" *J. Am. Chem. Soc.*, 1981, pp. 2127-2129, vol. 103.
Foucault, A.P. et al. "Biphasic Mixture of Water, Dimethyl Sulfoxide, and Tetrahydrofuran for use in Centrifugal Partition Chromatography" *Anal. Chem.*, 1993, pp. 2150-2154, vol. 65.
Furihata, K. et al. "*J*-Resolved HMBC, a New NMR Technique for Measuring Heteronuclear Long-Range Coupling Constants" *Tetrahedron Lett.*, 1999, pp. 6271-6275, vol. 40.
Griesinger, C. et al. "Two-Dimensional Correlation of Connected NMR Transitions" *J. Am. Chem. Soc.*, 1985, pp. 6394-6396, vol. 107 No. 22.
Grubbs, R.H. et al. "Ring-Closing Metathesis and Related Processes in Organic Synthesis" *Acc. Chem. Res.*, 1995, pp. 446-452, vol. 28.
Gunasekera, S.P. et al. "Discodermolide: a New Bioactive Polyhydroxylated Lactone from the Marine Sponge *Discodermia dissoluta*" *J. Org. Chem.*, 1990, pp. 4912-4915, vol. 55.
Hanessian, S. et al. "Preparation and Synthetic Utility of *tert*-Butyldiphenylsilyl Ethers" *Can. J. Chem.*, 1975, pp. 2975-2977, vol. 53, No. 19.
Hagiwara, H. et al. "A total synthesis of (+)-Perrottetianal A" *J. Chem. Soc., Chem. Commun.* 1987, pp. 1351-1353. Abstract.
Harris, L. et al. "Synthetic approaches to rapamycin. 3. Synthesis of a C1—C21 fragment" *Synlett*, 1996, pp. 903-905. Abstract.
Horwitz, S.B. "Personal Recollections of the early Development of Taxol" *J. Nat. Prod.*, 2004, pp. 136-138, vol. 67.
Hoye, T.R. et al. "A general, Practical, and Versatile Strategy for Accessing ω-Functional 1, 2-diols of high Enantiomeric Excess" *J. Org. Chem.*, 1998, pp. 8554-8557, vol. 63.

(56) References Cited

OTHER PUBLICATIONS

Huss, M. et al. "Concanamycin A, the Specific Inhibitor of V-ATPases, Binds to the $V_o$ Subunit c" *J. Biol. Chem.*, 2002, pp. 40544-40548, vol. 277, No. 43.

Jacobsen, E.N. et al. "Asymmetric Dihydroxylation via Ligand Accelerated Catalysis" *J. Am. Chem. Soc.*, 1988, pp. 1968-1970, vol. 110.

Jiang, L. et al. "Copper-Catalyzed Coupling of Amides and Carbamates with Vinyl Halides" *Org. Lett*, 2003, pp. 3667-3669, vol. 5, No. 20.

Jones, R.P.O. et al. "Expression, Purification and Secondary Structure Analysis of *Saccharomyces cerevisiae* Vacuolar Membrane $H^+$-ATPase Subunit F (Vma7p)" *Mol. Membrane Biol.*, 2001, pp. 283-290, vol. 18.

Kim, J.W. et al. "Oximidines I and II: Novel Antitumor Macrolides from *Pseudomonas* sp." *J. Org. Chem.*, 1999, pp. 153-155, vol. 64.

Kim, K.S. et al. "Efficient and Selective Cleavage of Acetals and Ketals using Ferric Chloride Adsorbed on Silica Gel" *J. Org. Chem.*, 1986, pp. 404-407, vol. 51.

Kim, S. et al. "Selective Cleavage of Acetal-type Ethers with Magnesium Bromide and Butyl Mercapton in Diethyl-Ether" *Synlett*, 1991, pp. 183-184. Abstract.

Klapars, A. et al. "A general and Efficient Copper Catalyst for the Amidation of Aryl Halides and the N-Arylation of Nitrogen Heterocycles" *J. Am. Chem. Soc.*, 2001, pp. 7727-7729, vol. 123.

Kluge, A.F. et al. "Synthesis of Prostaglandin Models and Prostaglandins by Conjugate Addition of a Functionalized Organocopper Reagent," *J. Am. Chem. Soc.*, 1972, pp. 7827-7832, vol. 94, No. 22.

Kocovsky, P. "Carbamates: A Method of Synthesis and Some Synthetic Applications" *Tetrahedron Lett*, 1986, pp. 5521-5524, vol. 27, Issue 45.

Larcheveque, M. et al. "Synthese Enantiospecifique Du 5-Hexadecanolide, Pheromone De 'Vespa Orientalis'" *Tetrahedron*, 1984, pp. 1061-1065, vol. 40, Issue 6.

Laurencot, C.M. et al. "Inhibitors of Intracellular pH Regulation Induce Cisplatin Resistance in EMT6 Mouse Mammary Tumor Cells" *Oncol. Res.*, 1995, pp. 363-369, vol. 7(7-8). Abstract.

Lin, J. et al. "Effects of Astragali Radix on the Growth of Different Cancer Cell Lines" *World J. Gastroenterol.*, 2003, pp. 670-673, vol. 9(4).

Lipinski, C.A. et al. "Experimental and Computational Approaches to Estimate Solubility and Permeability in Drug Discovery and Development Settings" *Adv. Drug Deliv. Rev.*, 2001, pp. 3-26, vol. 46.

Martinez-Zaguilan, R. "Angiostatin's Partners" *Science*, 1999a, pp. 433-434, vol. 284, No. 5413.

Martinez-Zaguilan, R. et al., "Distinct Regulation of $pH^{in}$ and $[CA^{2+}]^{in}$ in Human Melanoma Cells with Different Metastatic Potential" *J. Cell Physiol.*, 1998, pp. 196-205. vol. 176.

Martinez-Zaguilan, R. et al. "pH and Drug Resistance. I. Functional Expression of Plasmalemmal V-type $H^+$-ATPase in Drug-Resistant Human Breast Carcinoma Cell Lines" *Biochem. Pharmacol.*, 1999b, pp. 1037-1046, vol. 57.

Martinez-Zaguilan, R. et al. "Vacuolar-Type $H^+$-ATPases are Functionally Expressed in Plasma Membranes of Human Tumor Cells" *Am. J. Physiol. Cell Physiol.*, 1993, pp. C1015-C1029, vol. 265 (4). Abstract.

Maudsley, A.A. et al. "Coherence Transfer Echoes" *Chem. Phys. Lett.*, 1978, pp. 9-14, vol. 55, Issue 1. Abstract.

McKee, T.C. et al. "The Lobatamides, Novel Cytotoxic Macrolides from Southwestern Pacific Tunicates" *J. Org. Chem.*, 1998, pp. 7805-7810, vol. 63.

Meng, D. et al. "Total Synthesis of Epothilones A and B" *J. Am. Chem. Soc.*, 1997, pp. 10073-10092, vol. 119.

Miracco, C. et al. "Evaluation of MDR1, LRP, MRP, and Topoisomerase IIα Gene mRNA Transcripts Before and After Interferon-α, and Correlation with the mRNA Expression Level of the Telomerase Subunits hTERT and TEP1 in Five Unselected Human Melanoma Cell Lines" *Int. J. Oncol.*, 2003, pp. 213-220, vol. 23.

Morel, N. et al. "Specific Sorting of the a1 Isoform of the V-$H^+$ ATPase a Subunit to Nerve Terminals Where it Associates with Both Synaptic Vesicles and the Presynaptic Plasma Membrane" *J. Cell Sci.*, 2003, pp. 4751-4762, vol. 116(23).

Murata, M. et al. "Absolute Configuration of Amphidinol 3, the First Complete Structure Determination from Amphidinol Homologues: Application of a New Configuration Analysis Based on Carbon-Hydrogen Spin-Coupling Constants" *J. Am. Chem. Soc.*, 1999, pp. 870-871, vol. 121.

Murata, T. et al. "Structure of the Rotor of the V-type $Na^+$-ATPase from *Enterococcus hirae*" *Science*, 2005, pp. 654-659, vol. 308.

Myers, M.A. et al. "Toxic type 1 Diabetes" *Rev. Endo. Metab. Disord.*, 2003, pp. 225-231, vol. 4.

Myers, M.A. et al. "Dietary Microbial Toxins and Type 1 diabetes" *Ann. N.Y. Acad. Sci.*, 2003, pp. 418-422, vol. 1005.

Nakajima, N. et al. "MPM (4-methoxybenzyl) Protection of Hydroxy Functions Under Mild Acidic Conditions" *Tetrahedron Lett.*, 1988, pp. 4139-4142, vol. 29, Issue 33.

Nicolaou, K.C. et al. "Activation of 7-Endo over 6-Exo Epoxide Openings. Synthesis of Oxepane and Tetrahydropyran Systems" *J. Am. Chem. Soc.*, 1989, pp. 5335-5340, vol. 111.

Nishi, T. et al. "The Vacuolar ($H^+$)-ATPases—Nature's Most Versatile Proton Pumps" *Nat. Rev. Mol. Cell Biol.*, 2002, pp. 94-103, vol. 3.

Nomiyama, H. et al. "Identification of Genes Differentially Expressed in Osteoclast-like Cells" *J. Interferon & Cyto. Res*, 2005, pp. 227-231, vol. 25.

Ohi, H. et al. "Efficient Route to Functionalized Eight-Membered Lactones Based on Intramolecular Silicon-Directed Acylative Ring-Opening Reactions of 3 (Tetrahydro-2-furyl)propanoic Acid Derivatives" *Synlett*, 1999, pp. 1757-1759. Abstract.

Ohtani, I. et al. "High-Field FT NMR Application of Mosher's Method. The Absolute Configurations of Marine Terpenoids" *J. Am. Chem. Soc.*, 1991, pp. 4092-4096, vol. 113.

Páli, T. et al. "Interaction of Inhibitors of the Vacuolar $H^+$-ATPase with the Transmembrane $V_o$-sector" *Biochem.*, 2004, pp. 12297-12305, vol. 43.

Paterson, I. et al. "A Practical Synthesis of (+)-Discodermolide and Analogues: Fragment Union by Complex Aldol Reactions" *J. Am. Chem. Soc.*, 2001, pp. 9535-9544, vol. 123.

Petasis, N.A. et al. "Titanium-Mediated Carbonyl Olefinations. 1. Methylenations of Carbonyl Compounds with Dimethyltitanocene" *J. Am. Chem. Soc.*, 1990, pp. 6392-6394, vol. 112.

Raghunand, N. et al. "pH and Drug Resistance. II. Turnover of Acidic Vesicles and Resistance to Weakly Basic Chemotherapeutic Drugs" *Biochem. Pharmacol.*, 1999, pp. 1047-1058, vol. 57.

Reiter, B. et al. "Mammalian Exocrine Secretions.XVIII: Chemical Characterization of Interdigital Secretion of Red Hartebeest, *Alcelaphus buselophus caama*" *J. Chem. Ecol.*, 2003, pp. 2235-2252, vol. 29, No. 10.

Ruiz-Cabello, J. et al. "Gradient-Enhanced Heteronuclear Correlation Spectroscopy: Theory and Experimental Aspects" *J. Mag. Res.* 1992, pp. 282-302, vol. 100, No. 2. Abstract.

Schlessinger, R.H. et al. "Total Synthesis of (+)-Rosaramicin Aglycone and its Diacetate" *J. Am. Chem. Soc.*, 1986, pp. 3112-3114, vol. 108.

Sennoune, S.R. et al. "Plasmalemmal Vacuolar-Type $H^+$-ATPase in Cancer Biology" *Cell Biochem. Biophys.*, 2004, pp. 185-206, vol. 40, No. 2.

Shen, R. et al. "Synthesis and V-ATPase Inhibition of Simplified Lobatamide Analogues" *Org. Lett.*, 2002, pp. 3103-3106, vol. 4, No. 18.

Shen, R. et al. "Synthesis of Enamides Related to the Salicylate Antitumor Macrolides Using Copper-Mediated Vinylic Substitution" *Org. Lett.*, 2000, 1333-1336, vol. 2, No. 9.

Smith, III, A.B. et al. "Evolution of a Gram-Scale Synthesis of (+)-Discodermolide" *J. Am. Chem. Soc.*, 2000, pp. 8654-8664, vol. 122.

Stocksdale, M.G. et al. "Asymmetric Total Synthesis of an Important 3-(Hydroxymethyl) Carbocephalosporin" *J. Org. Chem.*, 1998, pp. 1221-1225, vol. 63.

Sunazuka, T. et al. "Total synthesis of (+)-Madindoline A, and (−)-Mandinoline B, Potent, Selective Inhibitors of Interleukin 6. Deter-

(56) References Cited

OTHER PUBLICATIONS mination of the Relative and Absolute Configurations" *J. Am. Chem. Soc.*, 2000, pp. 2122-2123, vol. 122.
Sundquist, K. et al. "Inhibition of osteoclast proton transport by bafilomycin $A_1$ abolishes bone resorption" *Biochem. Biophys. Res. Commun.*, 1990, pp. 309-313, vol. 168. Abstract.
Sun-Wada, G-H. et al. "Diverse and Essential Roles of Mammalian Vacuolar-Type Proton Pump ATPase: Toward the Physiological Understanding of Inside Acidic Compartments" *Biochim. Biophys. Acta*, 2004, pp. 106-114, vol. 1658.
Takai, K. et al. "Simple and Selective Method for RCHO→(E)–RCH=CHX Conversion by Means of a $CHX_3$—$CrCl_2$ System" *J. Am. Chem. Soc.*, 1986, pp. 7408-7410, vol. 108.
Vogt, A. et al. "A Scalable High-Content Cytotoxicity Assay Insensitive to Changes in Mitochondrial Metabolic Activity" *Oncol. Res.*, 2004, pp. 305-314, vol. 14 (6). Abstract.
Wiley, G.A. et al. "Studies in Organophosphorus Chemistry. I. Conversion of Alcohols and Phenols to Halides by Tertiary Phosphine Dihaldes" *J. Am. Chem. Soc.*, 1964, pp. 964-965, vol. 86.
Xie, X.-S. et al. "Salicylihalamide A Inhibits the $V_o$ Sector of the V-ATPase Through a Mechanism Distinct from Bafilomycin $A_1$" *J. Biol. Chem.*, 2004, pp. 19755-19763, vol. 279, No. 19.
Yoon, N.M. "Selective Reduction of Organic Compounds with Aluminum and Boron Hydrides" *Pure Appl. Chem.*, 1996, pp. 843-848, vol. 68, No. 4.
Yoshida, W. et al. "Pteroenone; A Defensive Metabolite of the Abducted Antarctic Pteropod Clione antartica" *J. Org. Chem.*, 1995, pp. 780-782, vol. 60.
Zhang, J. et al. "Proton conduction and Bafilomycin Binding by the $V_o$ Domain of the Coated Vesical V-ATPase" *J. Biol. Chem.*, 1994, pp. 23518-23523, vol. 269, No. 38.
Zhu, Q. et al. "Studies toward the Total Synthesis of Clavulactone" *J. Org. Chem.*, 2001, 2692-2699, vol. 66.
De Bruijn, J. et al. "Determination of Octanol/Water Partition Coefficients for Hydrophobic Organic Chemicals With the 'Slow-Stirring' Method" *Environ. Toxicol. Chem.*, 1989, pp. 449-512, vol. 8, abstract.
Ellegaard, J. et al. "Elevated Lymphocyte ATP-ase Activity in Patients With Cancer of the Uterine Cervix" *Acta Obstet. Gynecol. Scand.*, 1975, pp. 223-226, vol. 54.
Li, G. et al. "Catalytic Asymmetric Aminohydroxylations (AA) of Olefins," *Angew Chem. Int. Ed. Engl.*, 1996, pp. 451-454, vol. 35, Abstract.
Lipshutz, B.H. et al. "β-(Trimethylsilyl) Ethoxymethyl Chloride—a New Reagent for the Protection of the Hydroxyl Group" *Tetrahedron Lett.*, 1980, pp. 3343-3346, vol. 21.
Wu, Y. et al. "Revision of the Absolute Configuration of Salicylihalamide A Through Asymmetric Total Synthesis" *Angew. Chem. Int. Ed.*, 2000, pp. 4308-4310, vol. 39.

\* cited by examiner

Palmerolide A NMR Data

| Position | δ¹H (ppm, mult, $J$(Hz)) | δ¹³C | gHMBC |
|---|---|---|---|
| 1 | | 166.1 | |
| 2 | 5.78 (1H, d, 15.2) | 121.3 | 1, 4 |
| 3 | 6.72 (1H, ddd, 5.0, 9.9, 15.2) | 150.0 | 1, 2, 4, 5 |
| 4 | 2.11 (2H, m) | 32.6 | 2, 3, 5, 6 |
| 5 | a  1.30 (1H, m)<br>b  1.05 (1H, m) | 25.7 | 7<br>6 |
| 6 | a  1.50 (1H, ddd, 4.5, 8.2, 11.2)<br>b  1.30 (1H, m) | 38.5 | 5, 7, 8<br>5, 7, 8 |
| 7 | 3.83 (1H, ddd, 4.4, 7.4, 7.6) | 74.5 | 5, 9 |
| 8 | 5.55 (1H, dd, 7.7, 15.5) | 134.3 | 6, 7, 9, 10 |
| 9 | 5.50 (1H, dd, 2.9, 15.5) | 129.6 | 7, 8, 10 |
| 10 | 4.15 (1H, br s) | 69.9 | |
| 11 | 4.49 (1H, dd, 2.2, 5.0, 10.5) | 73.2 | 9, 10, 12/13, $\underline{C}$ONH₂ |
| 12 | a  1.59 (1H, m)<br>b  0.98 (1H, m) | 30.1 | 12/13<br>11, 12/13 |
| 13 | 1.96 (2H, m) | 30.1 | 12/13, 14, 15 |
| 14 | 5.42 (1H, ddd, 4.7, 10.1, 14.6) | 132.7 | 12/13, 16 |
| 15 | 6.05 (1H, dd, 11.1, 14.6) | 128.4 | 12/13, 16, 17 |
| 16 | 5.60 (1H, d, 11.4) | 127.1 | 14, 15, 18, 25 |
| 17 | | 132.3 | |
| 18 | a  2.17 (1H, dd, 1.3, 13.2)<br>b  2.00 (1H, dd, 11.2, 13.2) | 43.9 | 16, 17, 19, 25<br>16, 17, 19, 20, 25 |
| 19 | 4.85 (1H, ddd, 1.3, 7.4, 11.2) | 75.8 | 1, 17, 18, 20, 21, 26 |
| 20 | 2.69 (1H, qdd, 6.5, 7.4, 9.6) | 37.3 | 18, 19, 21, 22, 26 |
| 21 | 5.14 (1H, d, 9.6) | 130.5 | 1  9, 20, 23, 26, 27 |
| 22 | | 133.3 | |
| 23 | 5.85 (1H, d, 14.2) | 117.2 | 21, 22, 24, 25 |
| 24 | 6.86 (1H, dd, 10.1, 14.2) | 122.9 | 22, 23, 1' |
| 25 | 1.62 (3H, s) | 13.3 | 21, 22, 23 |
| 26 | 0.90 (3H, d, 6.5) | 17.7 | 19, 20, 21 |
| 27 | 1.71 (3H, s) | 16.9 | 16, 17, 18 |
| 1' | | 163.9 | |
| 2' | 5.70 (1H, br s, 1.0) | 118.8 | 1', 3', 4', 5' |
| 3' | | 152.5 | |
| 4' | 1.83 (3H, s) | 27.7 | 1', 2', 3', 5' |
| 5' | 2.13 (3H, s) | 20.4 | 1', 2', 3', 4' |
| $\underline{C}$ONH₂ | 6.49 (2H, br) | 157.3 | |
| 24-N$\underline{H}$ | 9.84 (1H, d, 10.1) | | 23, 24, 1' |
| 10-O$\underline{H}$ | 5.18 (1H, d, 4.9) | | 9, 10, 11 |
| 7-O$\underline{H}$ | 4.69 (1H, d, 3.9) | | 6, 7, 8 |

FIG. 2

PALMEROLIDE A

| Panel/Cell Line | Percent Growth | | | | |
|---|---|---|---|---|---|
| | -8 | -7 | -6 | -5 | -4 |
| Leukemia | | | | | |
| CCRF-CEM | 74 | 56 | 62 | 57 | 52 |
| HL60(TB0 | 69 | 76 | 66 | 42 | 17 |
| K-562 | 70 | 55 | 51 | 21 | 8 |
| MOLT-4 | 39 | 45 | 36 | 36 | 18 |
| RPMI-8226 | 44 | 44 | 46 | 32 | 41 |
| SR | 34 | 30 | 28 | 25 | 24 |
| Non-Small Cell Lung Cancer | | | | | |
| A549/ATCC | 65 | 54 | 52 | 25 | -83 |
| EKVX | 127 | 116 | 103 | 58 | -90 |
| HOP-62 | N/A | N/A | N/A | N/A | N/A |
| HOP-92 | 78 | 72 | 70 | 66 | -3 |
| NCI-H226 | N/A | N/A | N/A | N/A | N/A |
| NCI-H23 | N/A | N/A | N/A | N/A | N/A |
| NCI-H322M | N/A | N/A | N/A | N/A | N/A |
| NCI-460 | 82 | 93 | 83 | 13 | -90 |
| NCI-H522 | 110 | 108 | 88 | 25 | -60 |
| Colon Cancer | | | | | |
| COLO 205 | 58 | 57 | 61 | 29 | -39 |
| HCC-2998 | 53 | -4 | -9 | -59 | -99 |
| HCT-116 | 51 | 45 | 51 | 11 | -100 |
| HCT-15 | 90 | 88 | 82 | 32 | -69 |
| HT29 | 94 | 65 | 69 | 12 | -34 |
| KM12 | 53 | 46 | 45 | 2 | -42 |
| SW-620 | 70 | 69 | 76 | 35 | -83 |
| CNS Cancer | | | | | |
| SF-268 | 93 | 93 | 44 | 13 | -82 |
| SF-295 | 81 | 55 | 41 | -9 | -78 |
| SF-539 | 100 | 67 | 56 | -61 | -89 |
| SNB-19 | 123 | 135 | 130 | 85 | -43 |
| SNB-75 | 40 | 23 | 29 | -13 | . |
| U251 | 83 | 78 | 58 | 34 | -70 |

FIG. 4A

PALMEROLIDE A

| Panel/Cell Line | Percent Growth | | | | |
|---|---|---|---|---|---|
| | -8 | -7 | -6 | -5 | -4 |
| Melanoma | | | | | |
| LOX IMVI | 53 | 47 | 37 | 17 | -44 |
| M14 | -20 | -54 | -65 | -91 | -97 |
| SK-MEL-2 | 52 | 55 | 55 | -1 | -62 |
| SK-MEL-28 | 131 | 115 | 108 | 16 | -29 |
| SK-MEL-5 | 56 | 60 | 42 | 4 | -70 |
| UACC-257 | 53 | 44 | 29 | -1 | -80 |
| UACC-62 | 2 | -29 | -11 | -39 | -68 |
| Ovarian Cancer | | | | | |
| IGROV1 | 50 | 69 | 50 | 56 | -82 |
| OVCAR-3 | 72 | 51 | 28 | -4 | -75 |
| OVCAR-4 | 97 | 88 | 98 | 79 | -21 |
| OVCAR-5 | 70 | 76 | 65 | 53 | -89 |
| OVCAR-8 | 105 | 100 | 93 | 26 | -80 |
| SK-OV-3 | 121 | 110 | 103 | 90 | -59 |
| Renal Cancer | | | | | |
| 786-0 | 124 | 113 | 104 | 40 | -88 |
| A498 | N/A | N/A | N/A | N/A | N/A |
| ACHN | 107 | 114 | 72 | 42 | -58 |
| CAKI-1 | 91 | 83 | 44 | 20 | -87 |
| RFX 393 | . | -8 | -21 | -57 | -85 |
| SN12C | 100 | 93 | 93 | 57 | -51 |
| TK-10 | 82 | 76 | 56 | -30 | -76 |
| UO-31 | 93 | 86 | 57 | 21 | -95 |
| Prostate Cancer | | | | | |
| PC-3 | 76 | 79 | 72 | 48 | 1 |
| DU-145 | N/A | N/A | N/A | N/A | N/A |
| Breast Cancer | | | | | |
| MCF7 | -17 | 24 | -18 | -78 | -99 |
| NCI/ADR-RES | 100 | 99 | 85 | 39 | -64 |
| MDA-MB-231/ATCC | 95 | 79 | 75 | 23 | -72 |
| HS 578T | N/A | N/A | N/A | N/A | N/A |
| MDA-MB-435 | 90 | 84 | 82 | 31 | -80 |
| BT-549 | 87 | 53 | 56 | 11 | -78 |
| T-47D | 140 | 85 | 139 | 99 | 38 |

FIG. 4B

Palmerolide C NMR Data

| Position | δ¹H (ppm, mult, J(Hz)) | ¹³C | gHMBC |
|---|---|---|---|
| 1 | | 165.32 | |
| 2 | 5.73 (1H, d, 15.5) | 121.33 | 1, 4 |
| 3 | 6.77 (1H, dt, 7.5, 15.5) | 148.92 | 1, 4, 5 |
| 4 | 1.35 (1H, m) | 31.02 | 3, 5, 6 |
|   | 2.13 (1H, m) | 31.02 | 2 |
| 5 | 1.89 (1H, m) | 31.42 | 6, 7 |
|   | 1.98 (1H, m) | 31.42 | 7 |
| 6 | 5.54 (1H, m) | 131.22 | 5, 7, 8 |
| 7 | 5.58 (1H, m) | 130.4 | 8 |
| 8 | 3.96 (1H, dd, 1.8, 5.6) | 72.2 | 6, 7 |
| 9 | 3.56 (1H, dd, 1.0, 6.6) | 75.00 | 8, 10 |
| 10 | 4.56 (1H, ddd, 2.2, 6.9, 10.7) | 73.76 | 8, O$\underline{C}$ONH$_2$ |
| 11 | 1.30 (1H, m) | 27.94 | 10 |
|    | 1.49 (1H, m) | 27.94 | |
| 12 | 1.95 (1H, m) | 30.27 | 10 |
|    | 1.54 (1H, m) | 30.27 | 13, 14 |
| 13 | 1.90 (1H, m) | 29.48 | 15 |
|    | 1.99 (1H, m) | 29.48 | 14, 15 |
| 14 | 5.46 (1H, ddd, 4.7, 10.0, 14.8) | 131.85 | 13, 15, 16 |
| 15 | 6.08 (1H, dd, 11.2, 14.5) | 126.52 | 13, 14, 16 |
| 16 | 5.63 (1H, d, 11.0) | 128.21 | 14, 15, 27 |
| 17 | | 131.56 | |
| 18 | 2.07 (1H, m) | 43.16 | 16, 17, 19, 27 |
|    | 2.18 (1H, m) | 43.16 | 16, 17, 27 |
| 19 | 4.85 (1H, ddd, 2.0, 8.0, 11.2) | 74.07 | 1, 26 |
| 20 | 2.72 (1H, qdd, 7.0, 8.0, 10.0) | 36.81 | 19, 21, 22, 26 |
| 21 | 5.15 (1H, d, 9.5, 10.2) | 129.84 | 9, 20, 23, 26, 25 |
| 22 | | 132.70 | |
| 23 | 5.85 (1H, d, 14.5) | 116.55 | 21, 22, 24, 25 |
| 24 | 6.85 (1H, dd, 10.3, 13.8) | 122.17 | 22, 23, 1' |
| 25 | 1.69 (3H, s) | 12.77 | 21, 22, 23 |
| 26 | 0.90 (3H, d, 7.2) | 17.30 | 19, 20, 21 |
| 27 | 1.59 (3H, s) | 15.98 | 16, 17, 18 |
| 1' | | 163.16 | |
| 2' | 5.68 (1H, br t, 1.0) | 118.08 | 1', 4', 5' |
| 3' | | 151.63 | |
| 4' | 1.82 (3H, s) | 27.15 | 2', 3', 5' |
| 5' | 2.11 (3H, s) | 19.72 | 1', 2', 3', 4' |
| O$\underline{C}$ONH$_2$ | | 156.91 | |
| OCON$\underline{H}_2$ | 6.37 (2H, br) | | |
| 24-N$\underline{H}$ | 9.85 (1H, d, 11.5) | | 23, 1' |
| 8-O$\underline{H}$ | 4.62 (1H, d, 5.0) | | 7, 8, 9 |
| 9-O$\underline{H}$ | 4.72 (1H, d, 5.0) | | 8, 9, 10 |

FIG. 10

PALMEROLIDE C

| Panel/Cell Line | Percent Growth | | | | |
|---|---|---|---|---|---|
| | -8 | -7 | -6 | -5 | -4 |
| Leukemia | | | | | |
| CCRF-CEM | 98 | 86 | 60 | -24 | -24 |
| HL60(TB0 | 101 | 92 | 64 | 1 | -23 |
| K-562 | 84 | 63 | 55 | 18 | 16 |
| MOLT-4 | 84 | 44 | 16 | -60 | -78 |
| RPMI-8226 | 68 | 45 | 6 | -32 | -29 |
| SR | | | | | |
| Non-Small Cell Lung Cancer | | | | | |
| A549/ATCC | 86 | 71 | 45 | 19 | -11 |
| EKVX | 102 | 107 | 118 | 86 | -56 |
| HOP-62 | 102 | 105 | 99 | -17 | -74 |
| HOP-92 | 100 | 88 | 54 | 10 | -67 |
| NCI-H226 | 104 | 102 | 115 | 89 | -43 |
| NCI-H23 | 99 | 88 | 70 | -13 | -82 |
| NCI-H322M | 103 | 102 | 111 | 65 | -60 |
| NCI-460 | 95 | 93 | 86 | 21 | |
| NCI-H522 | 97 | 95 | 87 | 14 | -33 |
| Colon Cancer | | | | | |
| COLO 205 | 97 | 90 | 76 | 9 | 2 |
| HCC-2998 | 109 | 83 | 92 | -75 | -77 |
| HCT-116 | 92 | 59 | 56 | -25 | -85 |
| HCT-15 | 91 | 87 | 79 | -51 | -60 |
| HT29 | 85 | 73 | 53 | -3 | 3 |
| KM12 | 100 | 100 | 95 | 21 | -20 |
| SW-620 | 95 | 95 | 91 | 14 | -3 |
| CNS Cancer | | | | | |
| SF-268 | 101 | 107 | 106 | 59 | -46 |
| SF-295 | 87 | 55 | -26 | -66 | -89 |
| SF-539 | 99 | 103 | 113 | 12 | -71 |
| SNB-19 | 92 | 115 | 105 | 57 | -13 |
| SNB-75 | 66 | 56 | 19 | 16 | -37 |
| U251 | 103 | 99 | 68 | 21 | -69 |

FIG. 11A

PALMEROLIDE C

| Panel/Cell Line | Percent Growth | | | | |
|---|---|---|---|---|---|
| | -8 | -7 | -6 | -5 | -4 |
| Melanoma | | | | | |
| LOX IMVI | 106 | 103 | 78 | -10 | -4 |
| M14 | 95 | 55 | -41 | -80 | -85 |
| SK-MEL-2 | 107 | 96 | 79 | 7 | -46 |
| SK-MEL-28 | 93 | 96 | 85 | 20 | -23 |
| SK-MEL-5 | 104 | 82 | 55 | -55 | -48 |
| UACC-257 | 85 | 72 | 41 | -22 | -52 |
| UACC-62 | 98 | 99 | 24 | -43 | -56 |
| Ovarian Cancer | | | | | |
| IGROV1 | 88 | 61 | 77 | 37 | -42 |
| OVCAR-3 | 104 | 95 | 85 | -66 | -91 |
| OVCAR-4 | 88 | 98 | 104 | 32 | -49 |
| OVCAR-5 | 120 | 129 | 124 | 72 | -72 |
| OVCAR-8 | 97 | 97 | 94 | 29 | -12 |
| SK-OV-3 | 96 | 108 | 109 | 73 | -9 |
| Renal Cancer | | | | | |
| 786-0 | 96 | 91 | 82 | -10 | -68 |
| A498 | 101 | 106 | 81 | -5 | -50 |
| CAKI-1 | 74 | 41 | -19 | -56 | -93 |
| RFX 393 | 72 | 62 | 55 | -14 | -40 |
| SN12C | 96 | 94 | 87 | 46 | -33 |
| TK-10 | 101 | 101 | 171 | 64 | -55 |
| UO-31 | 99 | 100 | 63 | -27 | -47 |
| Prostate Cancer | | | | | |
| PC-3 | 95 | 88 | 64 | -14 | -88 |
| DU-145 | 96 | 101 | 90 | 52 | -68 |
| Breast Cancer | | | | | |
| MCF7 | 100 | 94 | 47 | 9 | -40 |
| NCI/ADR-RES | 106 | 107 | 109 | 54 | -58 |
| MDA-MB-231/ATCC | 100 | 106 | 72 | -15 | -40 |
| HS 578T | 92 | 91 | 81 | 31 | -9 |
| MDA-MB-435 | 96 | 76 | 67 | -65 | -81 |
| BT-549 | 95 | 104 | 97 | 52 | -43 |
| T-47D | 96 | 92 | 80 | 50 | 12 |

FIG. 11B

Palmerolide D NMR Data

| Position | ¹H (ppm. Mul, $J$ (Hz)) | ¹³C | gHMBC |
|---|---|---|---|
| 1 | | 166.08 | |
| 2 | 5.76 (1H, d, 15.8) | 121.18 | 1, 3, 4 |
| 3 | 6.71 (1H, ddd) | 150.02 | 1, 2, 4 |
| 4 | 2.11 (1H, m) | 33.04 | 2, 3, 5 |
| | 2.15 (1H, m) | 33.04 | 2, 3 |
| 5 | 1.98 (1H, m) | 30.08 | 3, 4 |
| | 1.30 (1H, m) | 38.35 | 3, 6 |
| 6 | 1.48 (1H, m) | 38.35 | |
| 7 | 3.82 (1H, m) | 73.17 | 6, 8, 9 |
| 8 | 5.53 (1H, m) | 134.21 | 7, 9, 10 |
| 9 | 5.49 (1H, m) | 129.56 | 7, 8, 11, 12 |
| 10 | 4.15 (1H, m) | 69.92 | 8, 9, 12 |
| 11 | 4.48 (1H, m) | 75.82 | 9, 10, 13 OCONH₂ |
| 12 | 1.94 (1H, m) | 30.04 | |
| 13 | 1.94 (1H, m) | 30.04 | |
| 14 | 5.41 (1H, m) | 133.62 | 13, 15, 16 |
| 15 | 6.04 (1H, dd, 11.6, 14) | 126.95 | 14, 16 |
| 16 | 5.59 (1H, d, 12) | 128.37 | 14, 15, 25 |
| 17 | | 132.24 | 15, 16, 18, 25 |
| 18 | 2.16 (1H, m) | 43.87 | 16, 19, 25 |
| | 2.00 (1H, m) | 43.87 | 16, 19 |
| 19 | 4.84 (1H, m) | 74.50 | 17, 18, 20, 26 |
| 20 | 2.68 (1H, m) | 37.28 | 18, 19, 21, 26 |
| 21 | 5.14 (1H, d, 9.7) | 130.67 | 19, 20, 26, 27 |
| 22 | | 133.34 | 21, 23, 27 |
| 23 | 5.86 (1H, d, 14.6) | 117.47 | 21, 24, 27 |
| 24 | 6.85 (1H, dd, 10.4, 15) | 122.65 | 22, 23, 1' |
| 25 | 1.60 (3H, s) | 16.84 | 15, 16, 18 |
| 26 | 0.89 (3H, d) | 17.74 | 19, 20, 21 |
| 27 | 1.70 (3H, s) | 13.34 | 21, 23 |
| | | | |
| 1' | | 163.49 | |
| 2' | 5.81 (1H, s) | 120.27 | 1', 4', 7' |
| 3' | | 153.23 | |
| 4' | | 40.83 | 2', 3', 5', 7' |
| 5' | | 143.61 | |
| 6' | 4.72 (2H, d) | 112.57 | 4', 8' |
| 7' | 1.76 (3H, s) | 24.76 | 2', 3', 4' |
| 8' | 1.61 (3H, s) | 22.68 | 4', 5', 6' |
| OCONH₂ | 6.45 (2H, br) | 157.41 | |
| 24-N$\underline{H}$ | 9.94 (1H, d, 10.3) | | |

FIG. 14

Palmerolide E NMR Data

| Position | $^1$H (ppm. Mul, $J$ (Hz)) | $^{13}$C | gHMBC |
|---|---|---|---|
| 1 | | 165.31 | |
| 2 | 5.78 (1H, d, 15.7) | 120.32 | 1, 4 |
| 3 | 6.74 (1H, ddd) | 149.74 | 1, 4, 5 |
| 4 | 2.11 (1H, m) | 32.37 | 2, 3, 5 |
| | 2.14 (1H, m) | 32.37 | 2, 3 |
| 5 | 1.30 (1H, m) | 24.94 | 7 |
| | 1.05 (1H, m) | 24.94 | |
| 6 | 1.49 (1H, m) | 34.72 | 4, 5, 7 |
| | 1.29 (1H, m) | 34.72 | 5, 7 |
| 7 | 3.81 (1H, m) | 72.55 | 5, 9 |
| 8 | 5.53 (1H, dd, 1.4, 8.1) | 133.56 | 7, 9, 10 |
| 9 | 5.49 (1H, d, 2.9) | 128.91 | 7, 8, 10 |
| 10 | 4.12 (1H, m) | 69.22 | 8, 9, 11, 12/13 |
| 11 | 4.47 (1H, ddd, 1.5, 5.1, 10.7) | 75.13 | 9, 10, 12/13, $\underline{C}$ONH2 |
| 12 | 1.05 (2H, m) | 29.39 | 10, 13 |
| 13 | 1.95 (2H, m) | 29.39 | 12 |
| 14 | 5.42 (1H, ddd, 5.0, 10.0, 14.7) | 132.18 | 12/13, 15, 16 |
| 15 | 6.05 (1H, dd, 10.8, 14.8) | 126.30 | 12/13, 17, 16 |
| 16 | 5.61 (1H, d, 10.6) | 127.97 | 15, 14, 18, 27 |
| 17 | | 131.24 | |
| 18 | 2.09 (1H, m) | 42.94 | 16, 19, 20, 27 |
| | 2.16 (1H, m) | 42.94 | 16, 17, 19, 27 |
| 19 | 5.02 (1H, ddd, 2.2, 7.6, 10.8) | 72.49 | 1, 17, 20, 21, 26 |
| 20 | 2.94 (1H, qdd, 7.0, 7.6, 10.8) | 37.43 | 18, 19, 21, 22, 26 |
| 21 | 6.55 (1H, dd, 1.5, 10.2) | 154.88 | 19, 22, 23, 25, 26 |
| 22 | | 138.88 | |
| 23 | 9.41 (1H, s) | 195.64 | 21, 22, 26 |
| 25 | 1.67 (3H, d, 1.2) | 9.18 | 21, 22, 23 |
| 26 | 1.01 (3H, d, 7.3) | 15.49 | 19, 21, 20 |
| 27 | 1.63 (3H, s) | 16.13 | 16, 17, 18 |
| O$\underline{C}$ONH$_2$ | | 156.66 | |
| OCON$\underline{H}_2$ | 6.46 (2H, br) | | |

FIG. 16

PALMEROLIDE E

| Panel/Cell Line | Percent Growth | | | | |
|---|---|---|---|---|---|
| | -8 | -7 | -6 | -5 | -4 |
| Leukemia | | | | | |
| CCRF-CEM | N/A | N/A | N/A | N/A | N/A |
| HL60(TB0 | 75 | 97 | 94 | 73 | 40 |
| K-562 | 65 | 61 | 55 | 22 | 51 |
| MOLT-4 | 79 | 85 | 92 | 55 | 27 |
| RPMI-8226 | N/A | N/A | N/A | N/A | N/A |
| SR | 101 | 66 | 31 | 9 | 3 |
| Non-Small Cell Lung Cancer | | | | | |
| A549/ATCC | 41 | 44 | 40 | 19 | -44 |
| EKVX | 98 | 102 | 103 | 97 | -40 |
| HOP-62 | 93 | 93 | 90 | -53 | -78 |
| HOP-92 | N/A | N/A | N/A | N/A | N/A |
| NCI-H226 | 107 | 125 | 131 | 105 | -27 |
| NCI-H23 | 75 | 85 | 77 | -30 | -84 |
| NCI-H322M | 93 | 97 | 90 | 70 | -58 |
| NCI-460 | 99 | 92 | 91 | 47 | 1 |
| NCI-H522 | 92 | 80 | 69 | -28 | -29 |
| Colon Cancer | | | | | |
| COLO 205 | 63 | 62 | 36 | 1 | 6 |
| HCC-2998 | 71 | 75 | 62 | -65 | -74 |
| HCT-116 | 57 | 50 | 46 | -66 | -94 |
| HCT-15 | 89 | 86 | 75 | 3 | -93 |
| HT29 | 47 | 53 | 37 | 3 | 4 |
| KM12 | 99 | 98 | 97 | 55 | -32 |
| SW-620 | 77 | 81 | 82 | 6 | 2 |
| CNS Cancer | | | | | |
| SF-268 | 101 | 99 | 101 | 71 | -36 |
| SF-295 | 32 | 20 | -5 | -57 | -62 |
| SF-539 | 100 | 106 | 105 | 40 | -66 |
| SNB-19 | 104 | 107 | 100 | 16 | -8 |
| SNB-75 | 22 | 35 | 25 | 6 | -28 |
| U251 | 107 | 103 | 101 | 43 | -86 |

FIG. 17A

PALMEROLIDE E

| Panel/Cell Line | Percent Growth | | | | |
|---|---|---|---|---|---|
| | -8 | -7 | -6 | -5 | -4 |
| Melanoma | | | | | |
| LOX IMVI | 109 | 106 | 110 | 22 | -62 |
| M14 | -24 | -29 | -57 | -80 | -82 |
| SK-MEL-2 | 57 | 31 | 12 | -41 | -51 |
| SK-MEL-28 | 93 | 96 | 79 | -21 | -28 |
| SK-MEL-5 | 50 | 46 | 50 | -47 | -21 |
| UACC-257 | 42 | 41 | 28 | -41 | -55 |
| UACC-62 | 102 | -4 | -22 | -30 | -42 |
| Ovarian Cancer | | | | | |
| IGROV1 | 75 | 44 | 48 | 11 | -59 |
| OVCAR-3 | 77 | 85 | 70 | -51 | -49 |
| OVCAR-4 | 117 | 122 | 110 | 58 | -20 |
| OVCAR-5 | 122 | 133 | 125 | 70 | -86 |
| OVCAR-8 | 101 | 106 | 94 | 21 | -16 |
| SK-OV-3 | 104 | 107 | 104 | 54 | -22 |
| Renal Cancer | | | | | |
| 786-0 | 94 | 91 | 77 | -28 | -37 |
| A498 | 93 | 93 | 54 | -30 | -35 |
| ACHN | 102 | 106 | 94 | 34 | -100 |
| CAKI-1 | . | -7 | -18 | -39 | -76 |
| RFX 393 | 66 | 63 | 61 | -9 | -12 |
| SN12C | 97 | 95 | 91 | 56 | -1 |
| TK-10 | 96 | 99 | 91 | 102 | -55 |
| UO-31 | 105 | 73 | 58 | -35 | -60 |
| Prostate Cancer | | | | | |
| PC-3 | N/A | N/A | N/A | N/A | N/A |
| DU-145 | 99 | 105 | 102 | 58 | -48 |
| Breast Cancer | | | | | |
| MCF7 | 102 | 93 | 99 | 14 | -35 |
| NCI/ADR-RES | 116 | 122 | 110 | 76 | -61 |
| MDA-MB-231/ATCC | 103 | 82 | 75 | 9 | -18 |
| HS 578T | 83 | 92 | 87 | 18 | -11 |
| MDA-MB-435 | 75 | 74 | 56 | -28 | -51 |
| BT-549 | 95 | 105 | 100 | 66 | -32 |
| T-47D | 65 | 74 | 60 | 32 | 8 |

FIG. 17B

Palmerolide B NMR Data

| Position | δ ¹H (ppm, mult, $J$ (Hz)) | δ ¹³C | HMBC |
|---|---|---|---|
| 1 | | 168.2 | |
| 2 | 5.70 (1H, d, 15) | 122.3 | 1, 4 |
| 3 | 6.74 (1H, ddd, 4.0, 11, 15) | 150.7 | 1, 4, 5 |
| 4 | 2.14 (1H, m) | 34.0 | |
| | 2.10 (1H, m) | | |
| 5 | 1.34 (1H, m) | 26.1 | |
| | 1.14 (1H, m) | | |
| 6 | 1.08 (1H, m) | 31.8 | |
| | 1.55 (1H, m) | | |
| 7 | 4.57 (1H, m) | 77.4 | 6, 8, O$\underline{C}$ONH$_2$ |
| 8 | 4.20 (1H, m) | 72.1 | 9 |
| 9 | 5.72 (1H, m) | 133.4 | 8, 10 |
| 10 | 5.64 (1H, m) | 131.0 | 8, 11 |
| 11 | 4.64 (1H, m) | 81.6 | |
| 12 | 1.53 (1H, m) | 36.6 | 11 |
| | 1.79 (1H, m) | | 11 |
| 13 | 1.21 (1H, m) | 30.9 | |
| | 1.96 (1H, m) | | |
| 14 | 5.38 (1H, ddd, 4, 10.5, 14.5) | 133.3 | 15 |
| 15 | 6.01 (1H, dd, 10.5, 14.5) | 128.0 | 14, 17 |
| 16 | 5.57 (1H, d, 10.9) | 129.8 | 15, 18 |
| 17 | | 132.8 | |
| 18 | 2.15 (1H, m) | 45.2 | 20 |
| | 1.99 (1H, m) | | |
| 19 | 4.82 (1H, m) | 76.6 | 1, 20 |
| 20 | 2.68 (1H, qdd, 5, 10, 10) | 38.7 | |
| 21 | 5.08 (1H, d, 10) | 132.2 | 19, 20, 22, 25 |
| 22 | | 134.5 | |
| 23 | 5.85 (1H, d, 15) | 119.6 | 21, 22, 24, 25 |
| 24 | 6.86 (1H, d, 14.5) | 122.7 | 22, 23, 1' |
| 25 | 1.58 (3H, s) | 16.7 | 16, 17, 18 |
| 26 | 0.88 (3H, d, 6.5) | 17.7 | 19, 20, 21 |
| 27 | 1.71 (3H, s) | 13.2 | 21, 22, 23 |
| 1' | | 166.7 | |
| 2' | 5.64 (1H, br s) | 118.9 | 1', 3', 4', 5' |
| 3' | | 154.9 | 1', 2', 5' |
| 4' | 1.81 (3H, s) | 27.7 | 1', 2', 3', 5' |
| 5' | 2.09 (3H, s) | 20.4 | |
| O$\underline{C}$ONH$_2$ | | 159.9 | |

FIG. 20

Palmerolide F NMR Data

| Position | δ ¹H (ppm, mult, J (Hz)) | δ ¹³C | HMBC |
|---|---|---|---|
| 1 | | 167.4 | |
| 2 | 5.77 (1H, d, 15.8) | 120.2 | 1, 4 |
| 3 | 6.71 (1H, ddd, 5.0, 9.9, 15.2) | 149.3 | 1, 2, 4, 5 |
| 4 | 2.13 (2H, m) | 32.2 | 2, 3, 5 |
| 5 | 1.31 (1H, m) | 24.9 | 7 |
|   | 1.01 (1H, m) | 24.9 | |
| 6 | 1.48 (1H, m) | 37.9 | 5, 7, 8 |
|   | 1.30 (1H, m) | 37.9 | 7, 8 |
| 7 | 3.82 (1H, br d) | 72.8 | 5 |
| 8 | 5.54 (1H, dd, 7.7, 15.0) | 133.4 | 6, 7, 9, 10 |
| 9 | 5.49 (1H, dd, 2.9, 15.6) | 128.7 | 7, 8, 10 |
| 10 | 4.14 (1H, br s) | 69.5 | |
| 11 | 4.49 (1H, dd, 4.6, 10.2) | 75.0 | 9, 10, 12/13, OCONH₂ |
| 12 | 1.55 (1H, m) | 29.3 | 12/13, 14 |
|   | 0.98 (1H, m) | 29.3 | 11, 12/13 |
| 13 | 1.91 (2H, m) | 29.3 | 12/13, 14, 15 |
| 14 | 5.41 (1H, ddd, 4.7, 10.1, 14.6) | 131.9 | 12/13, 16 |
| 15 | 6.04 (1H, dd, 11.1, 14.8) | 126.3 | 12/13, 16, 17 |
| 16 | 5.60 (1H, d, 11.4) | 127.7 | 14, 15, 17, 18, 25 |
| 17 | | 132.3 | 8, 9, 11, 12/13 |
| 18 | 2.13 (1H, dd, 1.3, 14.8) | 43.2 | 16, 17, 19, 25 |
|   | 1.99 (1H, dd, 10.5, 14.8) | 43.2 | 16, 17, 19, 20, 25 |
| 19 | 4.86 (1H, ddd, 1.3, 8.2, 10.5) | 73.7 | 1, 17, 18, 20, 21, 26 |
| 20 | 2.68 (1H, qdd, 6.2, 8.2, 9.7) | 36.5 | 17, 18, 19, 21, 22, 26 |
| 21 | 5.15 (1H, d, 9.7) | 130.1 | 19, 20, 23, 26, 27 |
| 22 | | 131.5 | |
| 23 | 5.87 (1H, d, 14.9) | 116.9 | 21, 22, 24, 27 |
| 24 | 6.77 (1H, dd, 10.0, 15.3) | 121.8 | 22, 23, 1' |
| 25 | 1.69 (3H, s) | 12.6 | 16, 17, 18, 23 |
| 26 | 0.89 (3H, d, 6.2) | 16.9 | 19, 20, 21 |
| 27 | 1.60 (3H, s) | 16.1 | 19, 21, 22, 23, 26 |
| 1' | | 165.2 | |
| 2' | 2.92 (2H, s) | 44.4 | 1', 3', 4', 5' |
| 3' | | 139.8 | |
| 4' | 4.82 (2H, m) | 113.5 | 1', 2', 3', 5' |
| 5' | 1.71 (3H, s) | 22.4 | 1', 2', 3', 4' |
| OCONH₂ | | 156.5 | |
| 24-NH | 9.94 (1H, d, 10.0) | | 23, 24, 1' |
| 10-OH | 5.18 (1H, br d, 3.8) | | 9, 10, 11 |
| 7-OH | 4.69 (1H, m) | | 6, 7, 8 |

FIG. 21

Palmerolide G NMR Data

| Position | δ ¹H (ppm, mult, J (Hz)) | δ ¹³C | HMBC |
|---|---|---|---|
| 1 | | 165.4 | |
| 2 | 5.75 (1H, d, 14.4) | 120.7 | 1, 4 |
| 3 | 6.71 (1H, ddd, 5.0, 9.9, 15.2) | 149.6 | 1, 2, 4, 5 |
| 4 | 2.06 (2H, m) | 32.7 | 2, 3, 5 |
| 5 | 1.29 (1H, m) | 25.2 | 7 |
| | 1.02 (1H, m) | 25.2 | |
| 6 | 1.49 (1H, ddd, 4.5, 8.2, 11.2) | 37.9 | 5, 7, 8 |
| | 1.27 (1H, m) | 37.9 | 7, 8 |
| 7 | 3.82 (1H, m) | 72.7 | 5 |
| 8 | 5.55 (1H, dd, 7.7, 15.0) | 133.8 | 6, 7, 9, 10 |
| 9 | 5.47 (1H, dd, 2.9, 15.6) | 129.1 | 7, 8, 10 |
| 10 | 4.13 (1H, br s) | 69.5 | 11 |
| 11 | 4.48 (1H, dd, 4.6, 10.2) | 75.4 | 9, 10, 12/13, O$\underline{C}$ONH$_2$ |
| 12 | 1.54 (1H, m) | 29.4 | 12/13, 14 |
| | 0.94 (1H, m) | 29.7 | 11, 12/13 |
| 13 | 1.90 (2H, m) | 29.7 | 12/13, 14, 15 |
| 14 | 5.41 (1H, ddd, 4.7, 10.1, 14.6) | 132.2 | 12/13, 16 |
| 15 | 6.04 (1H, dd, 11.1, 14.8) | 126.6 | 12/13, 16, 17 |
| 16 | 5.58 (1H, d, 11.4) | 128.0 | 14, 15, 18, 25 |
| 17 | | 131.6 | 8, 9, 11, 12/13 |
| 18 | 2.17 (1H, dd, 1.3, 14.8) | 43.7 | 16, 17, 19, 25 |
| | 1.99 (1H, dd, 10.5, 14.8) | 43.7 | 16, 17, 19, 20, 25 |
| 19 | 4.81 (1H, ddd, 1.3, 8.2, 10.5) | 74.1 | 1, 17, 18, 20, 21, 26 |
| 20 | 2.65 (1H, qdd, 6.2, 8.2, 9.7) | 36.4 | 18, 19, 21, 22, 26 |
| 21 | 5.00 (1H, d, 9.7) | 128.6 | 19, 20, 23, 26, 27 |
| 22 | | 131.2 | |
| 23 | 6.18 (1H, d, 14.4) | 109.3 | 21, 22, 24, 27 |
| 24 | 6.93 (1H, dd, 10.9, 14.3) | 124.7 | 22, 23, 1' |
| 25 | 1.60 (3H, s) | 16.4 | 16, 17, 18 |
| 26 | 0.89 (3H, d, 6.2) | 17.5 | 19, 20, 21 |
| 27 | 1.77 (3H, s) | 20.6 | 19, 21, 22, 23, 26 |
| 1' | | 163.3 | |
| 2' | 5.68 (1H, br s, 1.0) | 118.1 | 1', 3', 4', 5' |
| 3' | | 152.5 | |
| 4' | 1.83 (3H, s) | 27.4 | 1', 2', 3', 5' |
| 5' | 2.11 (3H, s) | 19.9 | 1', 2', 3', 4' |
| O$\underline{C}$ONH$_2$ | | 156.7 | |
| 24-NH | 9.84 (1H, d, 10.1) | | 23, 24, 1' |
| 10-OH | 5.20 (1H, d, 4.9) | | 9, 10, 11 |
| 7-OH | 4.74 (1H, d, 3.9) | | 6, 7, 8 |

FIG. 22

Palmerolide H NMR Data

| Position | δ ¹H (ppm, mult, J (Hz)) | δ ¹³C | HMBC |
|---|---|---|---|
| 1 | | 168.2 | |
| 2 | 5.70 (1H, d, 15.5) | 122.3 | 1, 3, 4 |
| 3 | 6.75 (1H, ddd, 4, 11.5, 15.7) | 150.7 | 1, 2, 4 |
| 4 | 2.10 (1H, m) | 33.9 | 2, 3, 5 |
|   | 2.14 (1H, m) | | 2, 3 |
| 5 | 1.18 (1H, m) | 26.1 | 3, 4 |
|   | 1.32 (1H, m) | | 3, 6 |
| 6 | 1.10 (1H, m) | 31.8 | |
|   | 1.56 (1H, m) | | 8 |
| 7 | 4.58 (1H, m) | 77.5 | 9 |
| 8 | 4.20 (1H, m) | 72.2 | 7 |
| 9 | 5.74 (1H, m) | 132.3 | 8 |
| 10 | 5.63 (1H, m) | 131.1 | 9, 13, O$\underline{C}$ONH$_2$ |
| 11 | 4.66 (1H, m) | 81.7 | |
| 12 | 1.55 (1H, m) | 36.6 | |
|   | 1.80 (1H, m) | | 13 |
| 13 | 1.21 (1H, m) | 30.8 | 14 |
|   | 1.96 (1H, m) | | 14, 15 |
| 14 | 5.38 (1H, m) | 133.4 | 15, 16 |
| 15 | 6.02 (1H, dd, 10, 14.5) | 128.1 | 16 |
| 16 | 5.57 (1H, d, 11.5) | 129.7 | 19 |
| 17 | | 133.0 | 18, 25 |
| 18 | 2.00 (1H, m) | 45.2 | 19, 21, 25 |
|   | 2.15 (1H, m) | | 19, 20, 25 |
| 19 | 4.84 (1H, m) | 76.2 | 21, 26 |
| 20 | 2.68 (1H, m) | 38.7 | 21, 26 |
| 21 | 5.09 (1H, d, 10) | 132.3 | 22, 23 |
| 22 | | 134.5 | |
| 23 | 5.87 (1H, d, 14.6) | 119.7 | 22, 24, 26 |
| 24 | 6.87 (1H, d, 14.5) | 122.8 | 22, 23, 1' |
| 25 | 1.59 (3H, s) | 13.2 | 16, 18 |
| 26 | 0.89 (3H, d, 6.7) | 17.7 | 19, 20, 21 |
| 27 | 1.72 (3H, s) | 16.6 | 22, 23 |
| 1' | | 166.0 | |
| 2' | 5.76 (1H, s) | 120.5 | 1', 4' |
| 3' | | 155.7 | |
| 4' | 3.44 (2H, s) | 42.1 | 2', 3', 5' |
| 5' | | 144.6 | |
| 6' | 4.69 (2H, s) | 112.6 | |
| 7' | 1.61 (3H, s) | 22.4 | 4', 8' |
| 8' | 1.76 (3H, s) | 24.8 | 4', 5', 6' |
| O$\underline{C}$ONH$_2$ | | 159.9 | |

FIG. 23

Palmerolide K NMR Data

| Position | δ ¹H (ppm, mult, $J$ (Hz)) | δ ¹³C | HMBC |
|---|---|---|---|
| 1 | | 164.5 | |
| 2 | 5.75 (1H, d, 14.7) | 120.7 | 1, 4 |
| 3 | 6.81 (1H, m) | 149.4 | 1, 4, 5 |
| 4 | 2.15 (1H, m) | 30.7 | 2, 3, 5 |
|   | 2.13 (1H, m) | | |
| 5 | 1.37 (1H, m) | 27.9 | 3, 4, 6, 7 |
|   | 1.34 (1H, m) | | 3 |
| 6 | 5.55 (1H, m) | 130.6 | 7, 8 |
| 7 | 5.55 (1H, m) | 130.6 | 6, 8 |
| 8 | 3.97 (1H, m) | 72.0 | 6, 7 |
| 9 | 3.57 (1H, m) | 74.8 | 6, 7, 8, 10, 11 |
| 10 | 4.56 (1H, m) | 73.4 | 9, 11, 12 |
| 11 | 1.34 (1H, m) | 29.8 | 12 |
|   | 1.30 (1H, m) | | 12 |
| 12 | 1.54 (1H, m) | 30.1 | 13, 14 |
|   | 1.52 (1H, m) | | 14 |
| 13 | 1.97 (1H, m) | 31.2 | 12, 14 |
|   | 1.92 (1H, m) | | 12, 14 |
| 14 | 5.48 (1H, m) | 132.1 | 15 |
| 15 | 6.10 (1H, dd, 11.8, 14.7) | 126.4 | 13 |
| 16 | 5.67 (1H, d, 11.8) | 128.3 | 17, 18, 25 |
| 17 | | 130.1 | |
| 18 | 2.18 (2H, m) | 42.9 | 16, 17, 19, 20, 26 |
| 19 | 5.04 (1H, q, 6.7) | 72.5 | 1, 17, 21, 26 |
| 20 | 2.98 (1H, m) | 37.3 | 19, 21, 22, 26 |
| 21 | 6.58 (1H, d, 10.3) | 154.5 | 20, 23, 24, 26 |
| 22 | | 138.4 | |
| 23 | 9.41 (1H, s) | 194.9 | 22, 24 |
| 24 | 1.61 (3H, s) | 15.6 | 16, 17, 18 |
| 25 | 1.03 (3H, d, 6.7) | 15.6 | 19, 20, 21 |
| 26 | 1.68 (3H, s) | 8.6 | 21, 22, 23 |
| OCONH₂ | | 156.7 | |
| OCON$\underline{H}$₂ | 6.36 (2H, br) | | |
| 8-OH | 4.62 | | 9, 7, 8, 9 |
| 9-OH | 4.72 | | 8, 9, 10 |

CYTOTOXIN COMPOUNDS AND METHODS OF ISOLATION

CROSS REFERENCE TO RELATED APPLICATIONS

This application is the National Stage of International Application Number PCT/US2006/036484, filed Sep. 18, 2006, which claims the benefit of U.S. Provisional Application Ser. No. 60/717,598, filed Sep. 16, 2005, and this application is a continuation-in-part of U.S. application Ser. No. 10/906,386, filed Feb. 17, 2005, which claims the benefit of U.S. Provisional Application Ser. No. 60/521,073, filed Feb. 17, 2004, each of which is hereby incorporated by reference in its entirety including any tables, figures, or drawings.

This invention was developed under support from the National Science Foundation under grants OPP-9901076 and OPP-0125152; accordingly the U.S. government has certain rights in the invention.

BACKGROUND OF THE INVENTION

One of the greatest efforts of modern medicine is the control and abatement of cellular proliferative disorders, such as cancers. Considerable research has been conducted searching for new biologically active compounds having useful activity for specific cancers and the organisms which produce these compounds. For example, certain marine soft corals have shown to be a source of biologically active cytotoxins. Also, compounds from sponges have proven effective against lipoxygenase-mediated conditions in humans (See U.S. Pat. No. 6,750,247).

Tunicates have proven to be an important source of bioactive natural products. Among marine natural products that have advanced as cancer treatments the ecteinascidins and didemnins are derived from tunicates, and the eudistomins have potent antiviral activity. As part of an ongoing study of bioactivity among Antarctic marine invertebrates, the inventors had the occasion to study the tunicate _Synoicum adareanum_.

_S. adareanum_ is a circumpolar tunicate common in the shallow waters around Anvers island (64° 46'S, 64° 03'W) on the Antarctic Peninsula from 15 to 796 meters depth. _S. adareanum_ colonies consist of large rounded or club-shaped heads with the bottom stalk being wrinkled and leathery and only slightly narrower than the head. _S. adareanum_ colonies can be up to eighteen centimeters high with a diameter of twelve centimeters. _S. adareanum_ colonies may comprise a single head or, up to six heads can arise from a single stalk.

BRIEF SUMMARY OF THE INVENTION

The subject invention concerns extracts from _S. adareanum_ comprising Palmerolide A, Palmerolide B, Palmerolide C, Palmerolide E, Palmerolide E, Palmerolide F, Palmerolide G, Palmerolide H, and/or Palmerolide K and uses thereof. Compounds of the invention exhibit bioactivity in field-based feeding-deterrent assays. Presented are novel, isolated polyketides, Palmerolide A, Palmerolide B, Palmerolide C, Palmerolide D, Palmerolide E, Palmerolide F, Palmerolide G, Palmerolide H, and Palmerolide K as the major natural product from extracts of _S. adareanum_. These polyketides display selective cytotoxicity in the National Cancer Institute (NCI) 60 cell line panel inhibiting, inter alia, melanoma (UACC-64, $LC_{50}$ 0.018 µM) with three orders of magnitude greater sensitivity relative to other cell lines tested.

The present invention also concerns methods of treating a subject with cancer, comprising administering to the subject a therapeutically effective amount of at least one isolated compound obtained from extracts of a _Synoicum_ species. In one embodiment, the _Synoicum_ species is _S. adareanum_ and the isolated compound is a Palmerolide. In a specific embodiment, the Palmerolide is chosen from Palmerolide A1, Palmerolide B, Palmerolide C, Palmerolide D, Palmerolide E, Palmerolide F, Palmerolide G. Palmerolide H, and Palmerolide K.

BRIEF DESCRIPTION OF THE DRAWINGS

FIG. 2 shows a chart showing the NMR Data for Palmerolide A.

FIG. 4A shows a chart showing the National Cancer Institute (NCI) Developmental Therapeutics Program In-Vitro Testing Results for Palmerolide A.

FIG. 4B shows a continued chart, showing the National Cancer Institute (NCI) Developmental Therapeutics Program In-Vitro Testing Results for Palmerolide A.

FIG. 10 shows a chart showing the NMR Data for Palmerolide C.

FIG. 11A shows a chart showing the National Cancer Institute (NCI) Developmental Therapeutics Program In-Vitro Testing Results for Palmerolide C.

FIG. 11B shows a continued chart, showing the National Cancer Institute (NCI) Developmental Therapeutics Program In-Vitro Testing Results for Palmerolide C.

FIG. 14 shows a chart showing the NMR Data for Palmerolide D.

FIG. 16 shows a chart showing the NMR Data for Palmerolide E.

FIG. 17A shows a chart showing the National Cancer Institute (NCI) Developmental Therapeutics Program In-Vitro Testing Results for Palmerolide E.

FIG. 17B shows a continued chart, showing the National Cancer Institute (NCI) Developmental Therapeutics Program In-Vitro Testing Results for Palmerolide E.

FIG. 20 shows a chart showing the NMR Data for Palmerolide B.

FIG. 21 shows a chart showing the NMR Data for Palmerolide F.

FIG. 22 shows a chart showing the NMR Data for Palmerolide G.

FIG. 23 shows a chart showing the NMR Data for Palmerolide H.

FIG. 24 shows a chart showing the NMR Data for Palmerolide K.

DETAILED DISCLOSURE OF THE INVENTION

Figure 1:
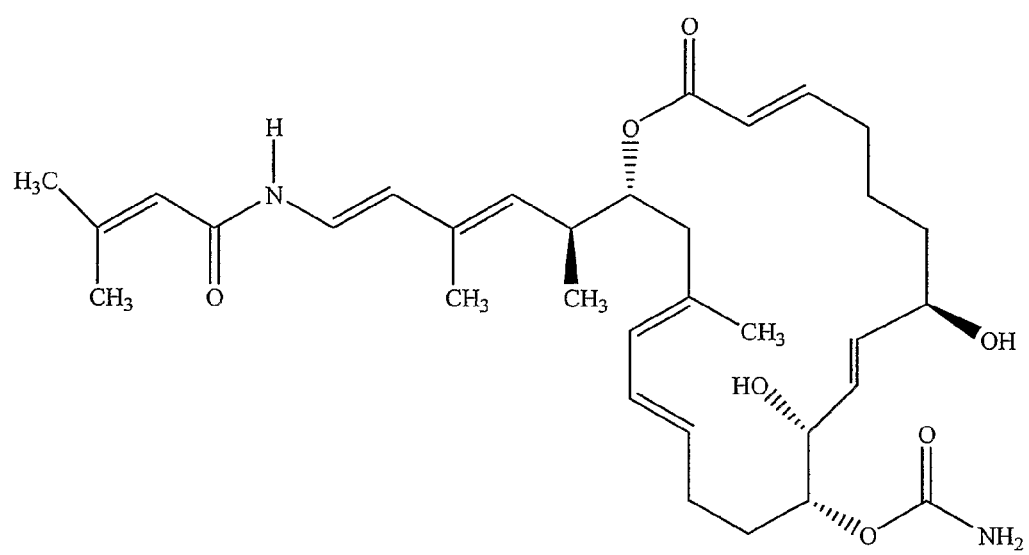
FIG. 1 shows a perspective view of the chemical formula for Palmerolide A.

The subject invention concerns extracts from *S. adareanum* comprising compounds, referred to herein as Palmerolides, and uses thereof. Palmerolides specifically exemplified herein include Palmerolide A, Palmerolide B, Palmerolide C, Palmerolide D, Palmerolide E, Palmerolide F, Palmerolide G, Palmerolide H, and Palmerolide K. Compounds of the invention exhibit bioactivity in field-based feeding-deterrent assays. The subject compounds display selective cytotoxicity in the National Cancer Institute (NCI) 60 cell line panel inhibiting, inter alia, melanoma cell lines.

Compounds of the present invention include those compounds having the chemical structure shown in formula (I):

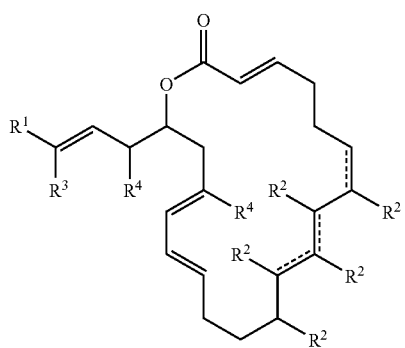

(I)

wherein:
═══ = single or double bond
$R^1$ is carboxaldehyde, —CHCHNHC(O)-Alkyl, —OC-Alkyl, —OC-aryl, —OC-amino, aryl, amino, -vinylamido, arylamido, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbony, heterocycloalkoxycarbonyl, a halogen, or —CHO, any of which can be optionally substituted with H, alkyl, alkoxy, —OH, —NO$_2$, —NH$_2$, —COOH, a halogen, or —CH$_3$;
$R^2$ is, independently, OH, O-Acyl, carbamate, H, O-alkyl, amino, —OSO$_3$H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbony, heterocycloalkoxycarbonyl, a halogen, and/or oxo;
$R^3$ is H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbony, heterocycloalkoxycarbonyl, halogen, any of which can be optionally substituted with alkyl, alkoxy, —OH, —NO$_2$, —NH$_2$, —COOH, a halogen, and/or —CH$_3$;
$R^4$ is, independently, H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbony, heterocycloalkoxycarbonyl, halogen, any of which can be optionally substituted with alkyl, alkoxy, —OH, —NO$_2$, —NH$_2$, —COOH, a halogen, and/or —CH$_3$;
and isomers, racemates or racemic mixtures thereof, or pharmaceutically acceptable salts or crystalline forms thereof.

In one embodiment, at least one $R^2$ is —OC(NH$_2$)O.
In one embodiment, $R^3$ is methyl.
In one embodiment, at least one $R^4$ is methyl. In a further embodiment, both $R^4$ are methyl.
In one embodiment, $R^1$ is —CHCHNHC(O)CHC(CH$_3$)$_2$.
In one embodiment, $R^1$ is —CHCHNHC(O)CHC(CH$_3$)CH$_2$C(CH$_3$)CH$_2$.
In one embodiment, $R^1$ is —CHCH—NHC(O)CH$_2$C(CH$_3$)CH$_2$
In one embodiment, $R^1$ is —CH═O.
In one embodiment, at least one $R^2$ is —OH.
In one embodiment, at least one $R^2$ is —OSO$_3$H.
In one embodiment, at least two $R^2$ are —OH and at least one $R^2$ is —OC(NH$_2$)O, and optionally $R^3$ and $R^4$ are —CH$_3$.

Compounds of the present invention include those compounds having the chemical structure shown in formula (II):

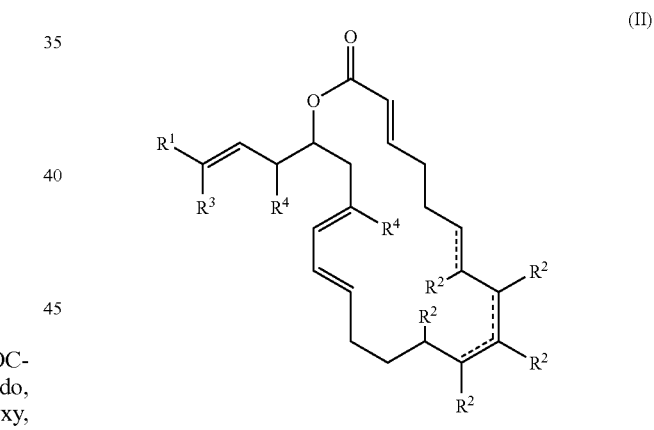

(II)

wherein:
═══ = single or double bond
$R^1$ is carboxaldehyde, —CHCHNHC(O)-Alkyl, —OC-Alkyl, —OC-aryl, —OC-amino, aryl, amino, -vinylamido, arylamido, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbony, heterocycloalkoxycarbonyl, a halogen, or —CHO, any of which can be optionally substituted with H, alkyl, alkoxy, —OH, —NO$_2$, —NH$_2$, —COOH, a halogen, or —CH$_3$;
$R^2$ is, independently, OH, O-Acyl, carbamate, H, O-alkyl, amino, —OSO$_3$H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbony, heterocycloalkoxycarbonyl, a halogen, and/or oxo;

$R^3$ is H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbony, heterocycloalkoxycarbonyl, halogen, any of which can be optionally substituted with alkyl, alkoxy, —OH, —NO$_2$, —NH$_2$, —COOH, a halogen, and/or —CH$_3$;

$R^4$ is, independently, H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbony, heterocycloalkoxycarbonyl, halogen, any of which can be optionally substituted with alkyl, alkoxy, —OH, —NO$_2$, —NH$_2$, —COOH, a halogen, and/or —CH$_3$;

and isomers, racemates or racemic mixtures thereof, or pharmaceutically acceptable salts or crystalline forms thereof.

In one embodiment, at least one $R^2$ is —OC(NH$_2$)O.

In one embodiment, $R^3$ is methyl.

In one embodiment, at least one $R^4$ is methyl. In a further embodiment, both $R^4$ are methyl.

In one embodiment, $R^1$ is —CHCHNHC(O)CHC(CH$_3$)$_2$.

In one embodiment, $R^1$ is —CHCHNHC(O)CHC(CH$_3$)CH$_2$C(CH$_3$)CH$_2$.

In one embodiment, $R^1$ is —CHCH—NHC(O)CH$_2$C(CH$_3$)CH$_2$

In one embodiment, $R^1$ is —CH=O.

In one embodiment, at least one $R^2$ is —OH.

In one embodiment, at least one $R^2$ is —OSO$_3$H.

In one embodiment, at least two $R^2$ are —OH and at least one $R^2$ is —OC(NH$_2$)O, and optionally $R^3$ and $R^4$ are —CH$_3$.

In one embodiment, a composition (or an isomer, racemate or racemic mixture thereof, or a pharmaceutically acceptable salt or crystalline form thereof) is provided comprising an isolated Palmerolide A compound of formula (III):

(III)

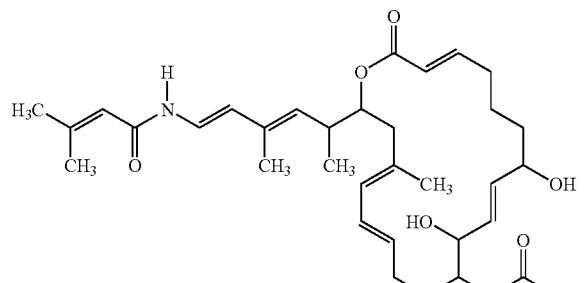

In yet another embodiment the present invention provides for a composition (or an isomer, racemate or racemic mixture thereof, or a pharmaceutically acceptable salt or crystalline form thereof) comprising an isolated Palmerolide C compound of formula (IV):

(IV)

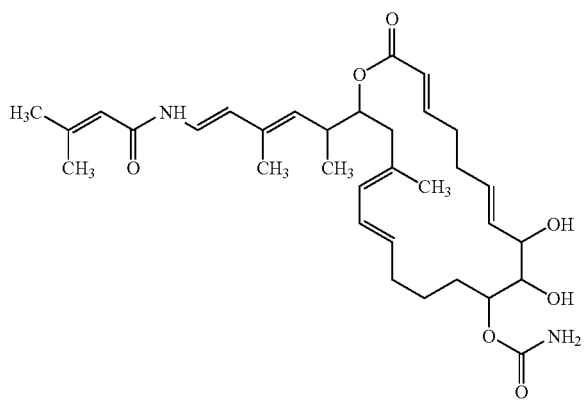

An additional embodiment the present invention provides for a composition (or an isomer, racemate or racemic mixture thereof, or a pharmaceutically acceptable salt or crystalline form thereof) comprising an isolated Palmerolide D compound of formula (V):

(V)

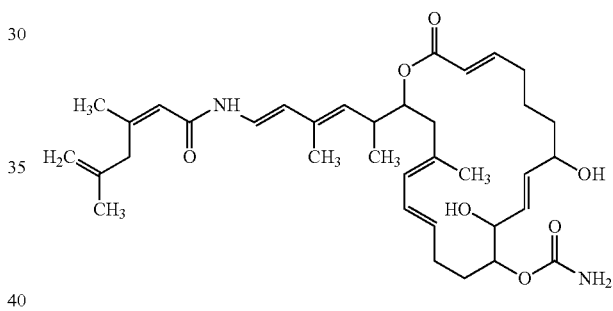

The present invention also provides for a composition (or an isomer, racemate or racemic mixture thereof, or a pharmaceutically acceptable salt or crystalline form thereof) comprising an isolated Palmerolide E compound of formula VI:

(VI)

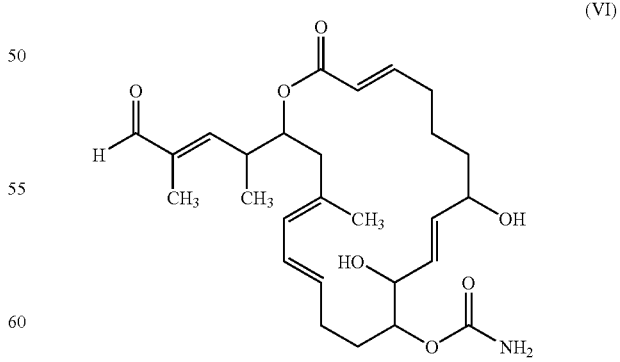

The present invention also provides for a composition (or an isomer, racemate or racemic mixture thereof, or a pharmaceutically acceptable salt or crystalline form thereof) comprising an isolated Palmerolide B compound of formula VII:

(VII)

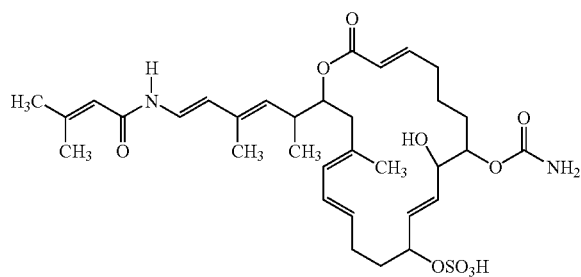

The present invention also provides for a composition (or an isomer, racemate or racemic mixture thereof, or a pharmaceutically acceptable salt or crystalline form thereof) comprising an isolated Palmerolide F compound of formula (VIII):

(VIII)

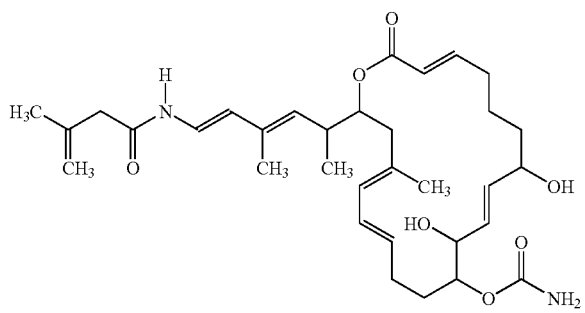

The present invention also provides for a composition (or an isomer, racemate or racemic mixture thereof, or a pharmaceutically acceptable salt or crystalline form thereof) comprising an isolated Palmerolide G compound of formula (IX):

(IX)

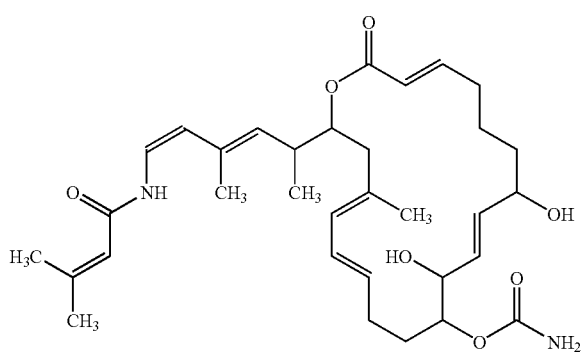

The present invention also provides for a composition (or an isomer, racemate or racemic mixture thereof, or a pharmaceutically acceptable salt or crystalline form thereof) comprising an isolated Palmerolide H compound of formula (X):

(X)

The present invention also provides for a composition (or an isomer, racemate or racemic mixture thereof, or a pharmaceutically acceptable salt or crystalline form thereof) comprising an isolated Palmerolide K compound of formula (XI):

(XI)

In preferred embodiments of the invention, the new compounds are substantially pure; ideally containing at least 95% of the compound as determined by established analytical methods, acceptably containing at least 90% of the desired compound, permissibly containing at least 75% of the compound.

Also provided by the discoveries of the invention are new pharmaceutical compositions between about 0.01% to 60% by weight, preferably 0.1% to 50% by weight, and more preferably 1% to 35% by weight based on the total weight of the composition, of one of the new compounds of the invention, or a mixture of two or more such compounds, and one or more pharmaceutically acceptable carriers or diluents.

Those skilled in the art will recognize that the Palmerolide compounds disclosed herein can exist in several tautomeric forms. All such tautomeric forms are considered as part of this invention.

As used herein, alkyl means straight or branched chain, saturated or mono- or polyunsaturated hydrocarbon groups having from 1 to 20 carbon atoms and $C_{1-X}$ alkyl means straight or branched chain alkyl groups containing from one Up to X carbon atoms, and includes alkyls, alkenyl, and alkynyls. For example, $C_{1-6}$ alkyl means straight or branched chain alkyl groups containing from 1 up to 6 carbon atoms. Alkoxy means an alkyl-O— group in which the alkyl group is as previously described. Cycloalkyl includes a nonaromatic monocyclic or multicyclic ring system, including fused and Spiro rings, of from about three to about 10 carbon atoms. A cyclic alkyl may optionally be partially unsaturated. Cycloalkoxy means a cycloalkyl-O— group in which cycloalkyl is as defined herein. Aryl means an aromatic monocyclic or multicyclic carbocyclic ring system, including fused and spiro rings, containing from about six to about 14 carbon atoms. Aryloxy means an aryl-O— group in which the aryl group is as described herein. Alkylcarbonyl means a RC(O)— group where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group where R is a cycloalkyl group as previously described.

Heteroalkyl means a straight or branched-chain having from one to 20 carbon atoms and one or more heteroatoms selected from nitrogen, oxygen, or sulphur, wherein the nitrogen and sulphur atoms may optionally be oxidized, i.e., in the form of an N-oxide or an S-oxide. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulphur atoms. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulphur and wherein an N atom may be in the form of an N-oxide. Arylcarbonyl means an aryl-CO— group in which the aryl group is as described herein. Heteroarylcarbonyl means a heteroaryl-CO— group in which the heteroaryl group is as described herein and heterocycloalkylcarbonyl means a heterocycloalkyl-CO— group in which the heterocycloalkyl group is as described herein. Aryloxycarbonyl means an ROC(O)— group where R is an aryl group as previously described. Heteroaryloxycarbonyl means an ROC(O)— group where R is a heteroaryl group as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane. Aryl groups include, for example, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, thiazolyl, pyrazolyl, pyridyl, indolyl, quinolinyl, isoquinolinyl, benzoquinolinyl, carbazolyl, and diazaphenanthrenyl.

As used herein, halogen means the elements fluorine (F), chlorine (Cl), bromine (Br), and iodine (I).

As used herein, oxo refers to compounds containing an oxygen atom, =O, doubly bonded to carbon or another element. The term embraces aldehydes, carboxylic acids, ketones, sulfonic acids, amides, and esters.

The subject invention also concerns kits, comprising in one or more containers a compound or composition of the invention. In a specific embodiment, a kit of the invention comprises one or more of a Palmerolide A, Palmerolide B, Palmerolide C, Palmerolide D, Palmerolide E, Palmerolide F, Palmerolide G, Palmerolide H, and Palmerolide K. In one embodiment, a kit further comprises a pharmaceutically acceptable carrier, such as a diluent. In another embodiment, a kit further comprises an antitumor or anticancer compound.

The subject invention also concerns methods for inhibiting a vacuolar adenosine triphosphatase (V-ATPase) enzyme, comprising contacting or exposing a V-ATPase to an effective amount of a compound or composition of the present invention sufficient to inhibit activity or block function of the V-ATPase. In one embodiment, the compound or composition comprises one or more Palmerolides selected from Palmerolide A, Palmerolide B, Palmerolide C, Palmerolide D, Palmerolide E, Palmerolide F, Palmerolide G, Palmerolide H, and Palmerolide K.

The subject invention also concerns methods for inhibiting or killing a cancer cell, comprising contacting the cell with an effective amount of a compound or composition of the invention. In one embodiment, the compound or composition comprises one or more Palmerolides selected from Palmerolide A, Palmerolide B, Palmerolide C, Palmerolide D, Palmerolide E, Palmerolide F, Palmerolide G, Palmerolide H, and Palmerolide K. Types of cancer cells that can be inhibited or killed according to the present invention include, but are not limited to cancer and/or tumor cells of bone, breast, kidney, mouth, larynx, esophagus, stomach, testis, cervix, head, neck, colon, ovary, lung, bladder, skin (e.g., melanoma), liver, muscle, pancreas, prostate, blood cells (including lymphocytes), and brain.

The subject invention also concerns methods for treating a condition associated with abnormal expression or overexpression of a V-ATPase enzyme comprising administering to a person or animal having the condition and in need of treatment of an effective amount of a compound or composition of the present invention. Conditions that can be treated according to the present invention include, but are not limited to, cell proliferation disorders, such as cancer; diabetes; pancreatitis; and osteoporosis. In one embodiment, the compound or composition comprises one or more Palmerolides selected from Palmerolide A, Palmerolide B, Palmerolide C, Palmerolide D, Palmerolide E, Palmerolide F, Palmerolide G, Palmerolide H, and Palmerolide K.

The present invention also provides methods of treating a person or animal with cancer or an oncological disorder. In one embodiment, a method comprises administering to the person or animal a therapeutically effective amount of at least one isolated compound obtained from extracts of a *Synoicum* species. The animal can be, but is not limited to, a mammal, such as primate (monkey, chimpanzee, ape, etc.), dog, cat, cow, pig, or horse, or other animals having an oncological disorder. Methods of the invention can optionally include identifying a person or animal who is or may be in need of treatment of cancer or an oncological disorder. In one embodiment, the *Synoicum* species is *S. adareanum* and the isolated compound is a Palmerolide. In a specific embodiment, the Palmerolide is chosen from Palmerolide A, Palmerolide B, Palmerolide C, Palmerolide D, Palmerolide E, Palmerolide F, Palmerolide G, Palmerolide H, and Palmerolide K. Types of cancer that can be treated according to the present invention include, but are not limited to cancer and/or tumors of the bone, breast, kidney, mouth, larynx, esophagus, stomach, testis, cervix, head, neck, colon, ovary, lung, bladder, skin (e.g., melanoma), liver, muscle, pancreas, prostate, blood cells (including lymphocytes), and brain. For the treatment of oncological disorders, the compounds and compositions of this invention can be administered to a patient in need of treatment in combination with other antitumor or anticancer substances or with radiation and/or photodynamic therapy or with surgical treatment to remove a tumor. These other substances or radiation treatments may be given at the same as or at different times from the compounds or compositions of this invention. For example, the compounds or compositions of the present invention can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

The subject invention also concerns methods for isolating and purifying a compound of the present invention. In one embodiment, the method comprises subjecting a *Synoicum* tunicate to solvent extraction; removing said solvent to provide an extract; and fractionating said extract to isolate said Palmerolide.

The subject invention also concerns methods for synthesizing a compound of the present invention.

"Pharmaceutically acceptable carrier" refers to any carrier, diluent, excipient, wetting agent, buffering agent, suspending agent, lubricating agent, adjuvant, vehicle, delivery system, emulsifier, disintegrant, absorbent, preservative, surfactant, colorant, flavorant, or sweetener, preferably non-toxic, that would be suitable for use in a pharmaceutical composition.

"Pharmaceutically acceptable equivalent" includes, without limitation, pharmaceutically acceptable salt or crystalline forms, hydrates, metabolites, prodrugs, and isosteres. Many pharmaceutically acceptable equivalents are expected to have the same or similar in vitro or in vivo activity as the compounds of the invention.

"Pharmaceutically acceptable salt or crystalline form" refers to a salt of the inventive compounds which possesses the desired pharmacological activity and which is neither biologically nor otherwise undesirable. The salt can be formed with acids that include, without limitation, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, thiocyanate, tosylate, and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. The basic nitrogen-containing groups can be quaternized with agents including lower alkyl halides such as methyl, ethyl, propyl, and butyl chlorides, bromides, and iodides; dialkyl sulfates such as dimethyl, diethyl, dibutyl, and diamyl sulfates; long chain halides such as decyl, lauryl, myristyl, and stearyl chlorides, bromides, and iodides; and aralkyl halides such as benzyl and phenethyl bromides.

"Prodrug" refers to a derivative of the inventive compounds that undergoes biotransformation, such as by metabolism, before exhibiting a pharmacological effect. The prodrug is formulated with the objective of improved chemical stability, improved patient acceptance and compliance, improved bioavailability, prolonged duration of action, improved organ selectivity, improved formulation (for example, increased hydrosolubility), and/or decreased side effects (for example, toxicity). The prodrug can be readily prepared from the inventive compounds using methods known in the art, such as those described by Burger's Medicinal Chemistry and Drug Chemistry, Fifth Ed., Vol. 1, pp. 172-178, 949-982 (1995).

"Palmerolide," as used herein, refers to a multi-membered macrocyclic polyketide bearing carbonate and amide-functionality. In one embodiment, the Palmerolide is isolated from the tunicate *Synoicum adareanum*; collected from the vicinity of Palmer Station on the Antarctic Peninsula.

"Polyketides," as used herein, refers to any natural compound containing alternating carbonyl and methylene groups ('β-polyketones'), derived from repeated condensation of acetyl coenzyme A.

"Macrocycle," as use herein, refers to a large molecule arranged in a circle with various semi-compounds attached at various points. The point of attachment and the nature of the sub-molecule determine the nature and physiological effect of the compound which contains it.

"Macrolide," as used herein, refers to a class of antibiotics characterized by molecules made up of large-ring lactones.

"Olefin," as used herein, is synonymous with "alkene" and refers to an acyclic hydrocarbon containing one or more double bonds.

As used herein, "a clinical response" is the response of a cell proliferative disorder, such as melanoma, colon, and renal cancer, to treatment with novel compounds disclosed herein. Criteria for determining a response to therapy are widely accepted and enable comparisons of the efficacy alternative treatments (see Slapak and Kufe, Principles of Cancer Therapy, in Harrison's Principles of Internal Medicine, 13th edition, eds. Isselbacher et al., McGraw-Hill, Inc. 1994). A complete response (or complete remission) is the disappearance of all detectable malignant disease. A partial response is an approximately 50 percent decrease in the product of the greatest perpendicular diameters of one or more lesions. There can be no increase in size of any lesion or the appearance of new lesions. Progressive disease means at least an approximately 25 percent increase in the product of the greatest perpendicular diameter of one lesion or tumor or the appearance of new lesions or tumors. The response to treatment is evaluated after the subjects had completed therapy.

A "pharmaceutical composition" of the invention is formulated to be compatible with its intended route of administration. Examples of routes of administration include parenteral, e.g., intravenous, intradermal, subcutaneous, oral or nasal (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol, and/or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g. a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

Compounds and compositions of the invention can be delivered to a cell either through direct contact with the cell or via a carrier means. Carrier means for delivering compositions to cells are known in the art and include, for example, encapsulating the compound or composition in a liposome moiety. Another means for delivery of a compound of the invention to a cell comprises attaching the compound to a protein or nucleic acid that is targeted for delivery to the target cell. U.S. Pat. No. 6,960,648 and Published U.S. Patent Application Nos. 20030032594 disclose amino acid sequences that can be coupled to another compound and that allows the compound to be translocated across biological membranes. Published U.S. Patent Application No. 20020035243 also describes compositions for transporting biological moieties across cell membranes for intracellular delivery. Compounds and compositions can also be incorporated into polymers, examples of which include poly(D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

It will be appreciated by those skilled in the art that compounds of the invention may contain one or more asymmetrically substituted carbon atoms which can give rise to stereoisomers. All such stereoisomers, including enantiomers, and diastereoisomers and mixtures, including racemic mixtures thereof, are contemplated within the scope of the present invention.

A "therapeutically effective amount" is the amount of a Palmerolide of the invention, including Palmerolides A, B, C, D, E, F, G, H, and K, or any combination thereof necessary to provide a therapeutically effective amount of the corresponding compound in vivo. The amount of the compound must be effective to achieve a response, including but not limited to total prevention of (e.g., protection against and complete cure) and to improved survival rate or more rapid recovery, or improvement or elimination of symptoms associated with a cellular proliferative disease or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

Example 1

Hollow Fiber Assay for Preliminary In Vivo Testing

The Biological Testing Branch of the Developmental Therapeutics Program has adopted a preliminary in vivo screening tool for assessing the potential anticancer activity of compounds identified by the large scale in vitro cell screen. This hollow fiber based assay has been in use since June, 1995.

Each compound is tested against a standard panel of 12 human tumor cell lines including NCI-H23, NCI-H522, MDA-MB-231, MDA-MB-435, SW-620 COLO 205, LOX IMVI, UACC-62, OVCAR-3, OVCAR 5, U251 and SF-295. The cell lines are cultivated in RPMI-1640 containing 10% FBS and 2 mM glutamine. On the day preceding hollow fiber preparation the cells are given a supplementation of fresh medium to maintain log phase growth. For fiber preparation the cells are harvested by standard trypsinization technique and resuspended at the desired cell density (varies by cell line between $2$–$10 \times 10^6$ cells/ml). The cell suspension is flushed into 1 mm I.D. polyvinylidene hollow fibers with a molecular weight exclusion of 500,000 Da. The hollow fibers are heat-sealed at 2 cm intervals and the samples generated from these seals are placed into tissue culture medium and incubated at 37° C. in 5% $CO_2$ for 24-48 hours prior to implantation. A total of 3 different tumor lines are prepared for each experiment so that each mouse receives 3 intraperitoneal implants (1 of each tumor line) and 3 subcutaneous implants (1 of each tumor line).

On the day of implantation, samples of each tumor cell line are quantitated for viable cell mass by a stable endpoint MTT assay so that the time zero (0) cell mass is known. Thus, the cytostatic and cytocidal capacities of the test compound can be assessed. Mice are treated with experimental agents starting on day 3 or 4 following fiber implantation and continuing once daily for a total of 4 doses. Each agent is assessed by intraperitoneal injection at 2 dose levels with 3 mice/dose/experiment. Vehicle controls consist of 6 mice receiving the compound diluent only. The fibers are collected from the mice on the day following the fourth compound treatment and subjected to the stable endpoint MTT assay. The optical density of each sample is determined spectrophotometrically at 540 nm and the mean of each treatment group is calculated. The percent net cell growth in each treatment group is calculated and compared to the percent net cell growth in the vehicle treated controls. Each compound is assessed in a total of 4 experiments (3 cell lines/experiment×4 experiments=12 cell lines).

Compounds are selected for further testing (for example, time/dose exposure studies preliminary pharmacology studies, subcutaneous xenograft efficacy studies) on the basis of several hollow fiber assay criteria. These include: (1) a reduction in net cell growth of 50% or greater in 10 of the 48 possible test combinations (12 cell lines X 2 sites X 2 compound doses); (2) a reduction in net cell growth of 50% or greater in a minimum of 4 of the 24 distant site combinations (intraperitoneal drug/subcutaneous culture); and/or (3) cell kill of 1 or more cell lines in either implant site (reduction in the viable cell mass below the level present at the start of the experiment).

To simplify evaluation, a point system has been adopted which allows rapid viewing of the activity of a given compound. For this, a value of 2 is assigned for each compound dose which results in a 50% or greater reduction in viable cell mass. The intraperitoneal and subcutaneous samples are scored separately so that criteria (1) and (2) can be evaluated. Compounds with a combined IP+SC score 20, a SC score 8, or a net cell kill of one or more cell lines can be considered for further studies. The maximum possible score for an agent is 96 (12 cell lines×2 sites×2 dose levels×2 [score]). These criteria were statistically validated by comparing the activity outcomes of >80 randomly selected compounds in the hollow fiber assay and in xenograft testing. This comparison indicated that there was a very low probability of missing a xenograft active compound if the hollow fiber assay were used as the initial in viva screening tool. Because of the design of the hollow fiber assay, the results of individual cell lines are not reported since the statistical power of the assay is based on the impact of a compound against the entire panel of cells. In addition to the hollow fiber results, other factors (for example, unique structure, mechanism of action, etc.) may result in referral of a compound for further studies without the compound meeting these hollow fiber assay criteria.

Example II

Palmerolide Isolation

Extracts from *S. adareanum*, Palmerolide A, Palmerolide C, Palmerolide D, and Palmerolide E displayed bioactivity in field-based feeding-deterrent assays, leading the inventors to investigate the chemical nature of the activity. Presented are novel, isolated polyketides, Palmerolide A, Palmerolide C, Palmerolide D, and Palmerolide E as the major natural product from extracts of *S. adareanum*. These polyketides display selective cytotoxicity in the National Cancer Institute (NCI) 60 cell line panel inhibiting, inter alia, melanoma (UACC-64, $LC_{50}$ 0.018 µM) with three orders of magnitude greater sensitivity relative to other cell lines tested.

Figure 19:
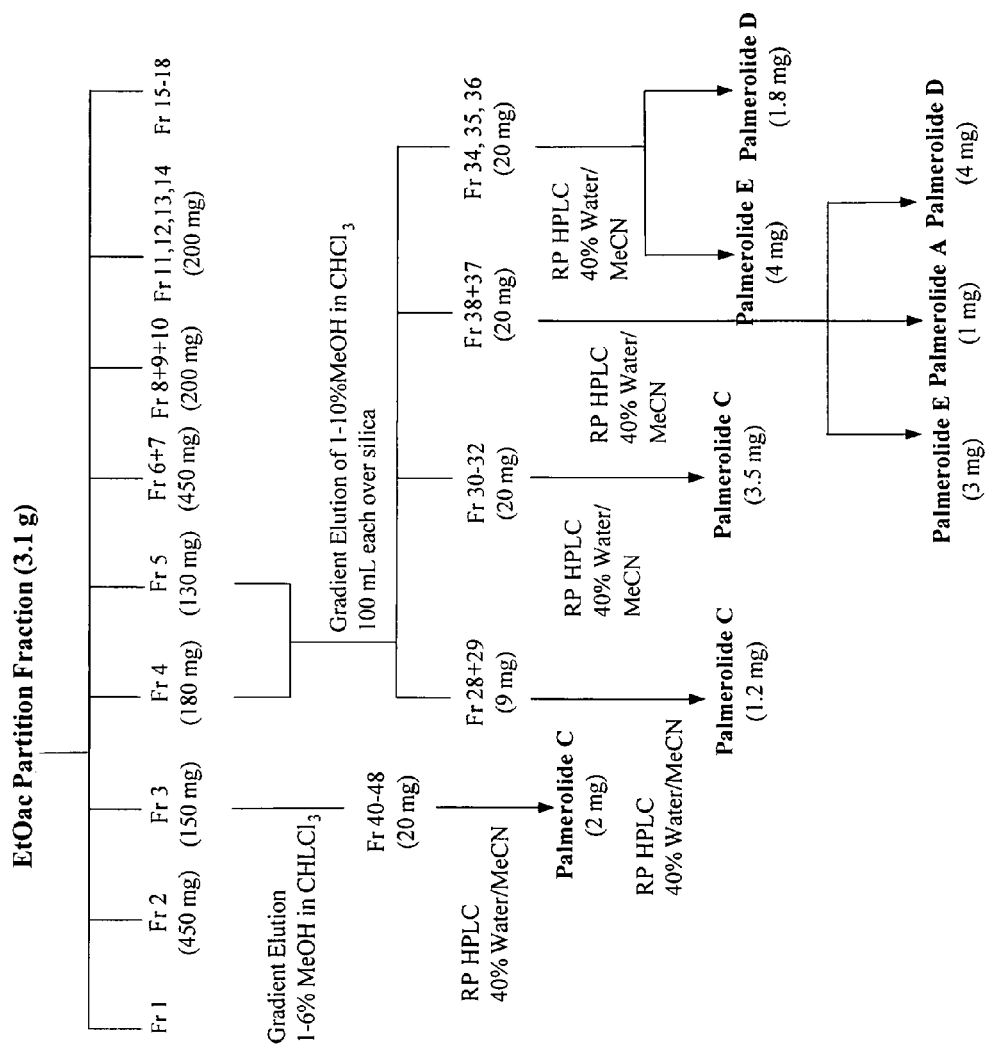
FIG. 19 shows the purification steps for isolating Palmerolide A-G.

In a similar manner, Palmerolides A-H, and K have been isolated to date using our standard protocols for fractionation of lipophilic natural products. Freeze-dried biomass was exhaustively extracted with dichloromethane/methanol 1:1 (3×) and the combined extract concentrated to dryness. The extract was applied to a silica gel column packed in 100% hexanes. Elution of two column volumes of hexanes as two fractions was followed by a step gradient of two column volumes of 1:9, 2:8, 4:6, 8:2 ethyl acetate/hexanes, 100% ethyl acetate, and finally 5%, 10% and 20% MeOH/ethyl acetate, collecting each column volume as a fraction. Repeated high pressure liquid chromatography (HPLC; Waters YMC 5µ, ODS 10 mm×30 mm using varying amounts water in MeCN, depending on the isolate) resulted in purification of five palmerolides. (see FIG. 19). Additional palmerolide metabolites can be isolated from the more polar fractions of the lipophilic extract. For example, further fractionation of the ethyl acetate/methanol eluting fractions from flash chromatography of the lipophilic extract has resulted in three more polar palmerolides (based on inspection of the $^1$H NMR spectrum, these palmerolides are more highly hydroxylated). Bioassays as described herein, and other known in the art, can confirm the bioactivity of any of these isolates.

More polar palmerolides or other melanoma-bioactive compounds present in the hydrophilic extracts can be fractionated by reversed phase vacuum chromatography. C-18 modified silica gel is packed, in water, in a vacuum funnel, then the extract applied and two bed volumes of water, 1:9, 2:8, 4:6, 8:2 methanol/water, then 100% methanol pulled through under vacuum, collecting one fraction per bed volume. Alternatively, polar constituents can be adsorbed onto polystyrene resins (HP-20 or XAD) and eluted with a similar gradient profile of methanol or acetone. Chromatographic fractions thus obtained are then concentrated and bioassayed. Subsequent or alternative chromatographic steps can be performed as is well known in the art, utilizing the same stationary phase described above, over a more narrow solvent gradient, or by another stationary phase, such as gel permeation (LH-20 or G-10), as necessary to achieve purification.

Final purification of bioactive isolates is by HPLC. Separations on HPLC utilize any number of stationary phases based on the chromatographic behavior of the isolate. Typically, reversed-phase (C-18, phenyl) columns work well with non-polar compounds, normal-phase with compounds of moderate polarity, and the variety of other bonded-phase (amino, cyano, diol) columns work with compounds having character similar to the packing. However, the use of reversed-phase HPLC on the separations of even the most polar organic compounds is not uncommon. We have had considerable success using polymeric stationary phase C-18 (YMC and/or Waters), which accommodate pure water and/or buffer solvents, so that even the most polar metabolites (amino acids, nucleosides) can be separated by reversed phase HPLC. Our HPLC instruments are equipped with both mass-sensitive (differential refractive index (RI) and/or evaporative light scattering (ELSD)) and ultraviolet detectors in series. Dual detection is important because the RI or ELSD detectors, while relatively insensitive, have a response proportional to quantity. The ultraviolet detector is highly sensitive, but the response is variable depending on the extinction coefficient of the chromophore. This HPLC instrumentation includes analytical, semi-preparative and preparative capabilities (four instruments, 0.1 mL/min to 300 mL/min) and our LC/MS can be integrated with any of the instruments to add MS (total ion chromatogram, TIC) detection when necessary, with the added advantage of securing mass spectral profiles of the isolates.

Although we have HPLC instrumentation for preparative isolation of palmerolides, this methodology has certain drawbacks which can be overcome by using centrifugal countercurrent chromatography (CCC) or centrifugal partition chromatography (CPC) well known in the art. CCC and CPC have the advantage of being based on the partition of the analyte between two immiscible phases, a physical property that lends itself to higher recovery than adsorption chromatography. Instrumentation available today includes multiple volume rotors (both techniques utilize a rotary-induced gravity gradient) for developmental through preparative scale separations. Foucault et al. achieved an effective purification of a polyketide macrolide (amphotericin B) using a water/DMSO/THF system which works as a good starting point for palmerolide purification. (Foucault, A. P. et al., 1993).

Example III

Palmerolide A

Palmerolide A was isolated as a white solid from the 1:1 methanol/ethyl acetate fraction eluting from silica gel chromatography of the crude lipophilic (1:1 methanol/dichloromethane) extract. Mass spectroscopic analysis provided a molecular formula of $C_{33}H_{48}N_2O_7$ (HRFABMS m/z 585.3539, Δ 0.1 mmu for [M$^+$+1]). The C-1 to C-24 carbon backbone of palmerolide A could be unambiguously assigned based on $^1H$-$^{13}C$ connectivity assignments from gHMBC spectra. The macrocycle was completed by observation of a correlation between the C-19 (δ 73.69) methine to the C-1 ester carbonyl. Hydroxy methines at C-7 and C-10 were conclusively assigned based on observation of coupling of the hydroxyl protons in both the gHMBC and COSY spectra: in the gHMBC spectrum, the hydroxy protons correlated to the respective α- and β-carbons, while in the COSY spectrum correlations were observed between the hydroxyl protons and the hydroxy methine protons. An isopentenoyl amide, established by 2D NMR analysis, completed the gross structure with the exception of $CO_2NH_2$ remaining unassigned from the molecular formula. This remaining carbon was correlated with the proton on the oxygen-bearing C-11 (δ 75.25), but no further connectivity was evident. The last remaining valence must be occupied by the —$NH_2$, resulting in a carbamoyl group at C-11 and completing the planar structure of palmerolide A.

Stereochemical analysis found all disubstituted olefins to bear the E configuration based on their large coupling constants (>14 Hz). The trisubstituted olefin at C-16 was also assigned as E based on observation of a correlation in the ROESY spectrum of H-16 to $H_2$-18 and of H-15 to $H_3$-25. Similarly, the C-21 olefin could be assigned the E configuration based on ROESY correlations of H-24 to $H_3$-27, of H-23 to $H_3$-27 and H-21, and of $H_3$-27 to H-20 and $H_3$-26. (R)- and (S)-MTPA esters[41] of palmerolide A demonstrated both C-7 and C-10 to bear the R configuration. Configurational analysis[42] of the C-10/C-11 fragment identified a gauche relationship between H-10 and H-11 based on the small $^3J_{H-10/H-11}$ observed between the vicinal protons and the large $^3J_{CH}$ for both the H-10/C-12 and the H-11/C-9 relationships. Further support for the conformation was found in $^2J_{C-11/H-10}$ and $^2J_{C-10/H-11}$, both of which were large and negative, defining the absolute stereochemistry of C-11 as R. Similarly, configurational analysis of the C-19/C-20 system suggested an anti relationship of the respective protons based on the large $^3J_{H-19/H-20}$, small $^3J_{C-21/H-19}$, $^3J_{C-26/H-19}$ and $^3J_{C-18/H-20}$, as well as the large $^2J_{C-19/H-20}$. The relative position of C-18 in this fragment was secured by the observation of ROESY correlations between $H_2$-18 and H-20 as well as $H_2$-18 and $H_3$-26 while no ROESY correlation was observed between $H_2$-18 and H-21, requiring the relative configuration 19R*, 20S*. The NMR data for Palmerolide A can be found in FIG. 2.

Figure 3:
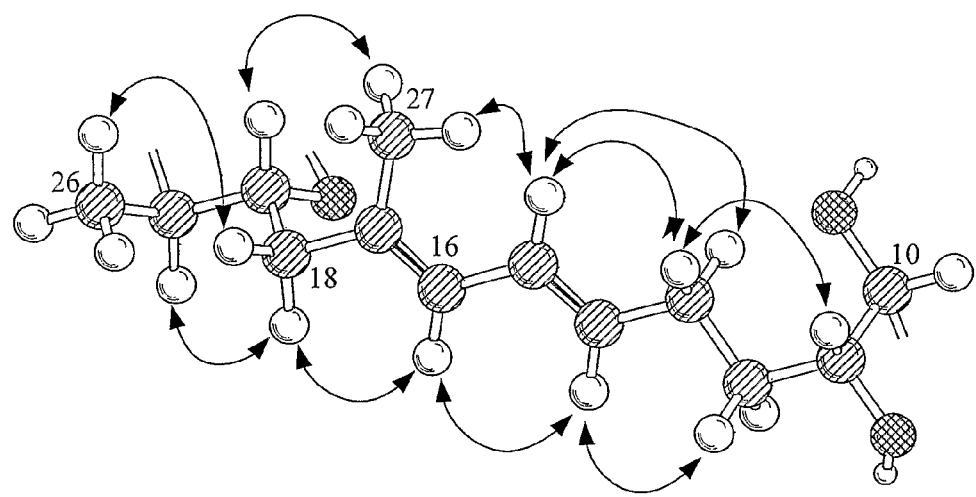
FIG. 3 shows selected ROE correlations relating the relative stereochemistry between C-11 and C-19.

The four olefins in the macrocycle constrain the flexibility often found in macrolides, facilitating stereochemical analysis by NOE studies. Further analysis of the ROESY spectrum revealed the macrolide to adopt two largely planar sides of a tear-drop shaped cycle, one side consisting of C-1 through C-6, the other C-11 through C-19, with C-7 through C-10 providing a curvilinear connection. In particular, H-19, $H_3$-27, H-15 and $H_2$-13 (see FIG. 3) are sequentially correlated in the ROESY spectrum, as are $H_3$-26, $H_2$-18, H-16, H-14 and H-12, defining the periphery of the top and bottom face of the western hemisphere. H-11 correlates only to the top series of protons, a result consistent only with C-19 and C-11 both adopting the R configuration.

Tunicates are not well known as producers of type I polyketides, though the patellazoles and iejimalides are significant, bioactive, representatives. Palmerolide A is unusual in bearing a small macrocycle, with 20 members, compared to 24 in the patellazoles and iejimalides, and a vinyl amide, a feature more commonly associated with cyanophyte-derived macrolides such as tolytoxin. Palmerolide A displays cytotoxicity toward several other melanoma cell lines, FIG. 2, [M14($LC_{50}$ 0.076 μM), SK-MEL-5 (6.8 μM) and LOX IMVI (9.8 μM)] as well as the previously mentioned UACC-62. Besides melanoma, FIG. 3, one colon cancer cell line (HCC-2998, 6.5 μM), FIG. 4A, and one renal cancer cell line (RXF 393, 6.5 μM), FIG. 4B, Palmerolide A was largely devoid of cytotoxicity ($LC_{50}$>10 μM), representing a selectivity index among tested cell lines of $10^3$ for the most sensitive cells. Significantly, Palmerolide A is COMPARE-negative against the NCI database, suggestive of a previously un-described mechanism of action.

Figure 5:
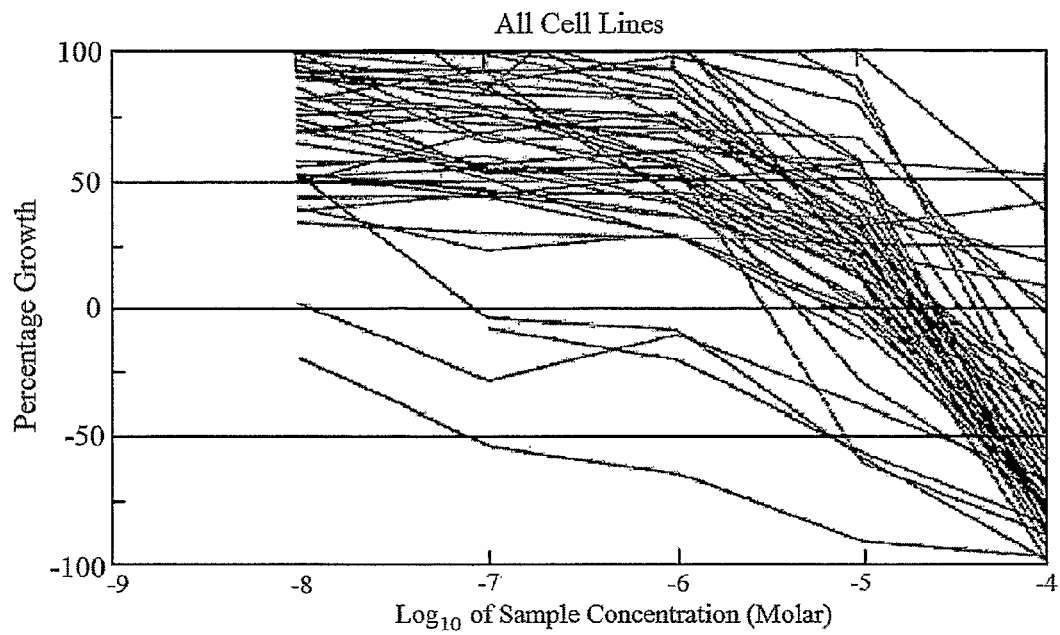
FIG. 5 shows a graph showing National Cancer Institute (NCI) Developmental Therapeutics Program Dose Response Curves for all cell lines tested for Palmerolide A.
Figure 6:
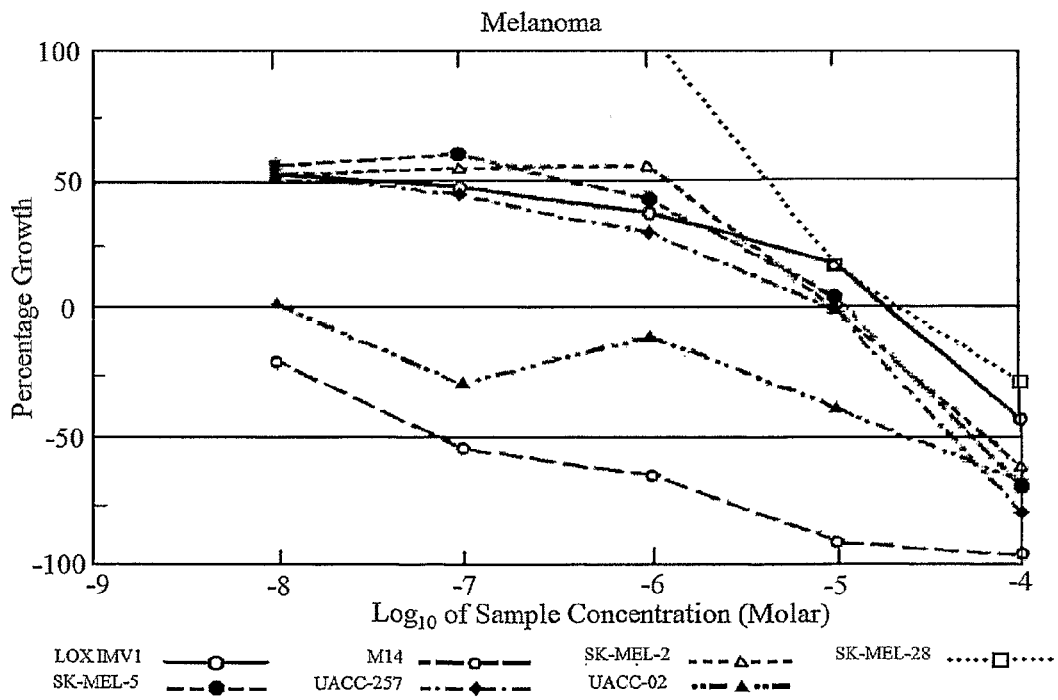
FIG. 6 shows a graph showing National Cancer Institute (NCI) Developmental Therapeutics Program Dose Response Curves for Melanoma cell lines tested for Palmerolide A.
Figure 7:
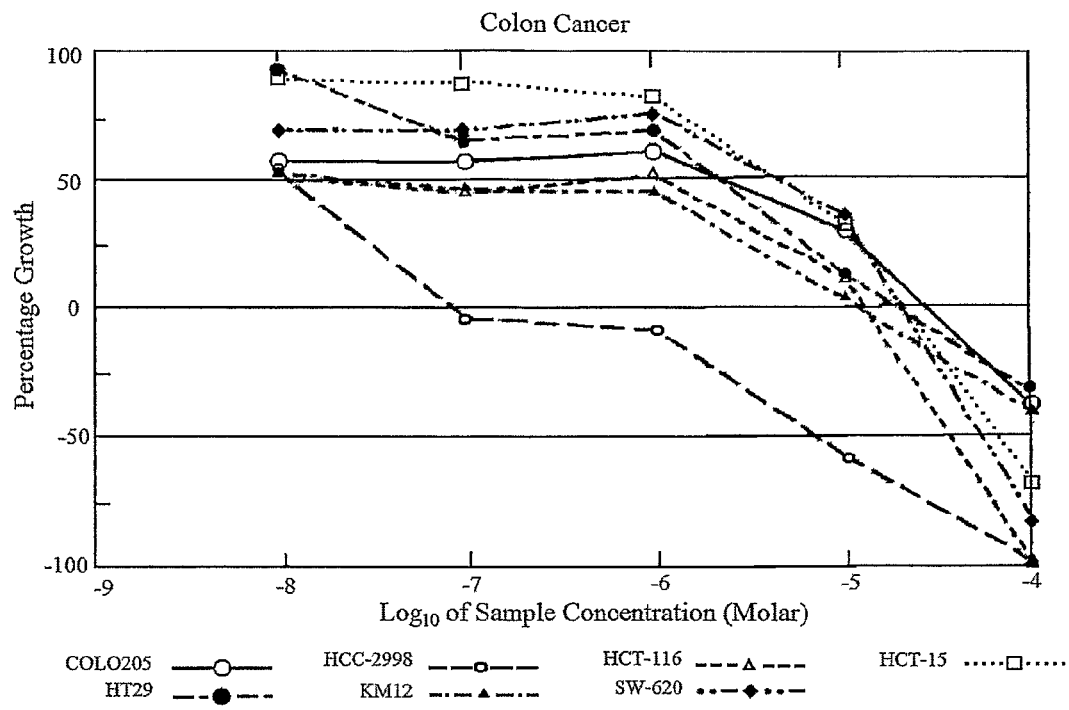
FIG. 7 shows a graph showing National Cancer Institute (NCI) Developmental Therapeutics Program Dose Response Curves for Colon Cancer cell lines tested for Palmerolide A.
Figure 8:
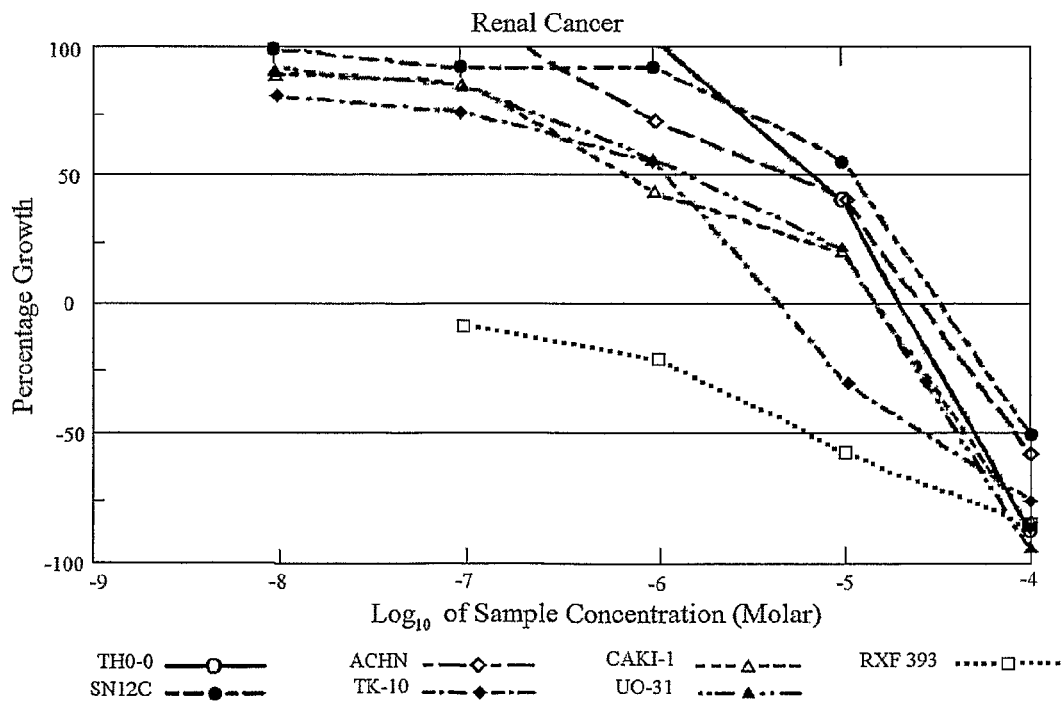
FIG. 8 shows a graph showing National Cancer Institute (NCI) Developmental Therapeutics Program Dose Response Curves for Renal Cancer cell (lines tested for Palmerolide A.

FIGS. 4A and 4B, indicate the National Cancer Institutes Developmental Therapeutics Program In-Vitro Testing Results for Palmerolide A. FIG. 5 shows the National Cancer Institute (NCI) Developmental Therapeutics Program Dose Response Curves for all cell lines tested for Palmerolide A. In comparison, individual results are shown for Melanoma (FIG. 6), Colon Cancer (FIG. 7) and Renal Cancer (FIG. 8).

Example IV

Cytotoxicity of Palmerolide C

Figure 9:
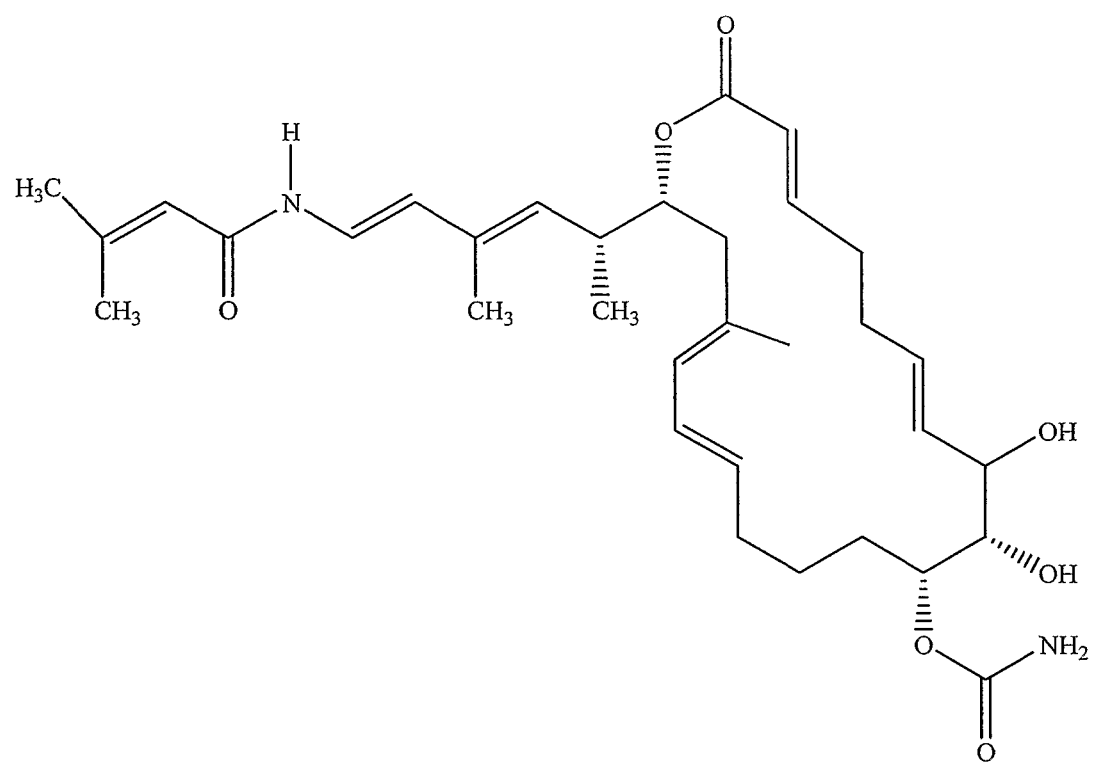
FIG. 9 shows a perspective view of the chemical formula for Palmerolide C.
Figure 12:
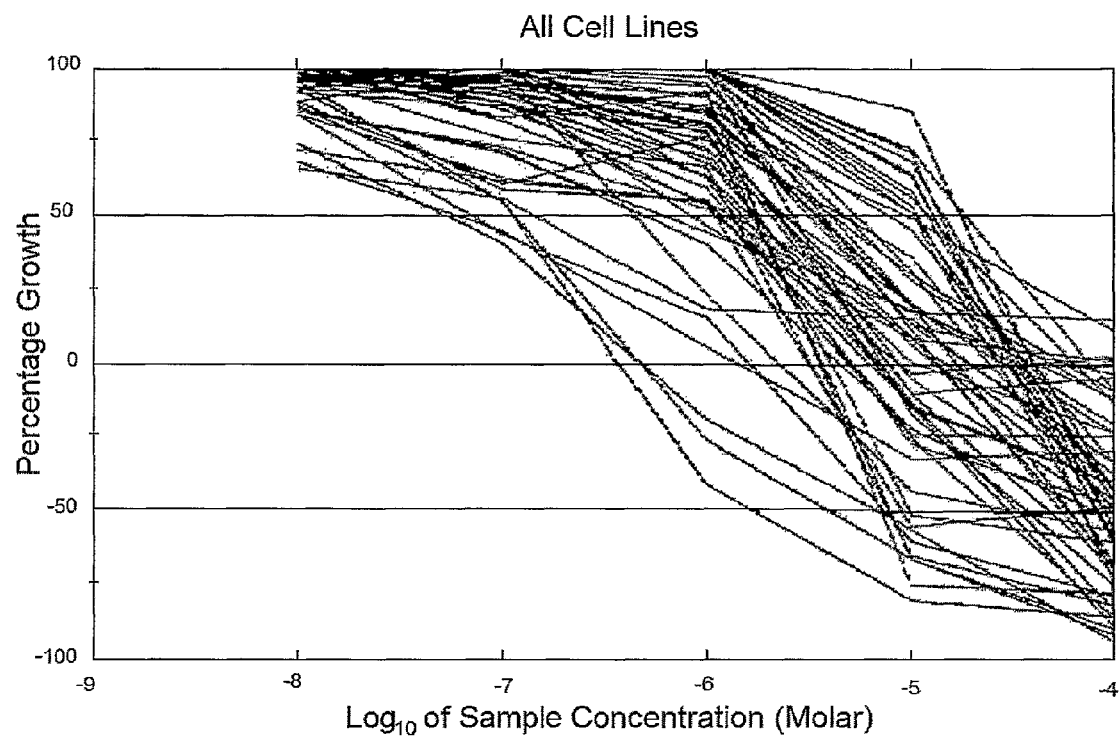
FIG. 12 shows a graph showing National Cancer Institute (NCI) Developmental Therapeutics Program Dose Response Curves for all cell lines tested for Palmerolide C.

Palmerolide C, shown below and in FIG. 9, has the chemical formula $C_{33}H_{49}N_2O_7$ (for NMR data see FIG. 10). NCI cytotoxicity is shown in FIG. 11A and FIG. 11B. NCI Dose Response Curves for all cell lines are presented in FIG. 12.

Example V

Cytotoxicity of Palmerolide D

Figure 13:
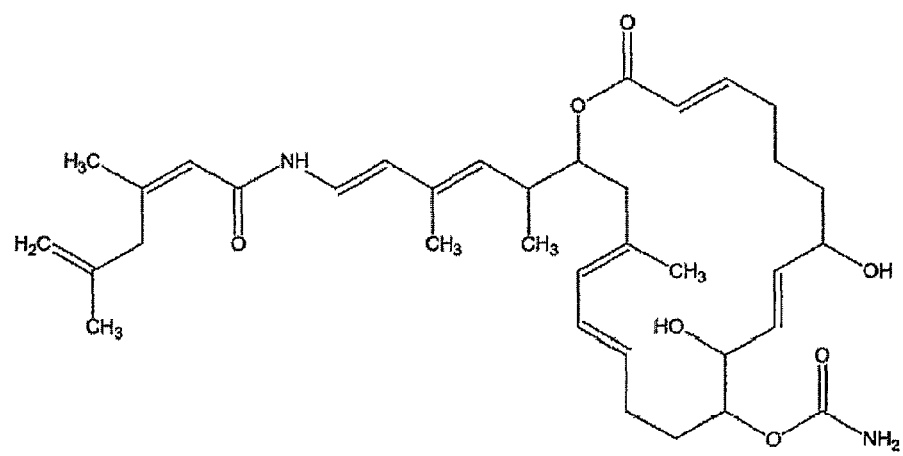
FIG. 13 shows a perspective view of the chemical formula for Palmerolide D.

Palmerolide D, shown below and in FIG. 13, has the chemical formula $C_{36}H_{53}N_2O_7$. Palmerolide D NMR Data is shown in FIG. 14.

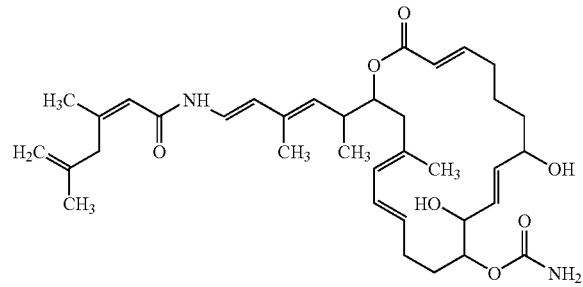 [SMILES: C=C(C)C/C(C)=C\C(=O)N/C=C/C(C)=C/C(C)C1C/C(C)=C/C=C/CCC(OC(N)=O)C(O)/C=C/C(O)CCC/C=C/C(=O)O1]

Example VI

Cytotoxicity of Palmerolide E

Figure 15:
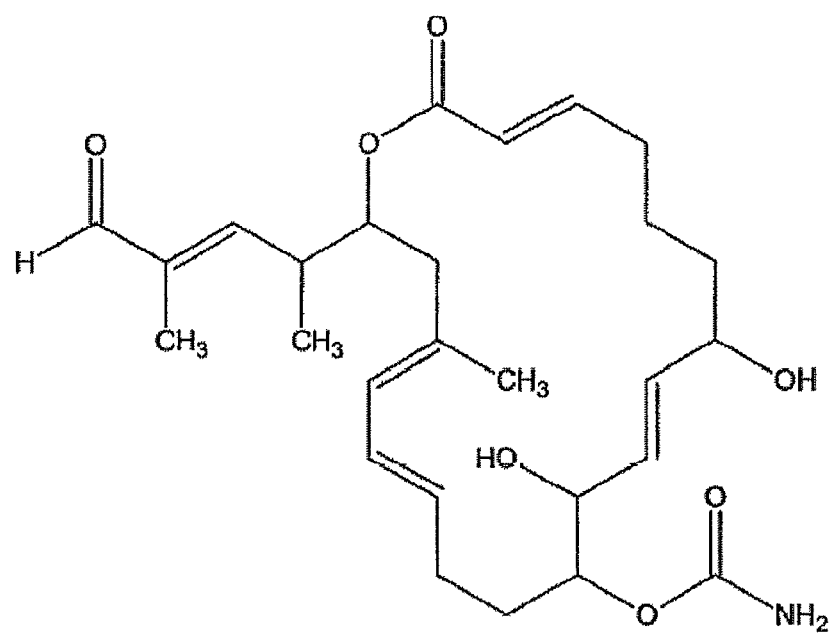
FIG. 15 shows a perspective view of the chemical formula for Palmerolide E.
Figure 18:
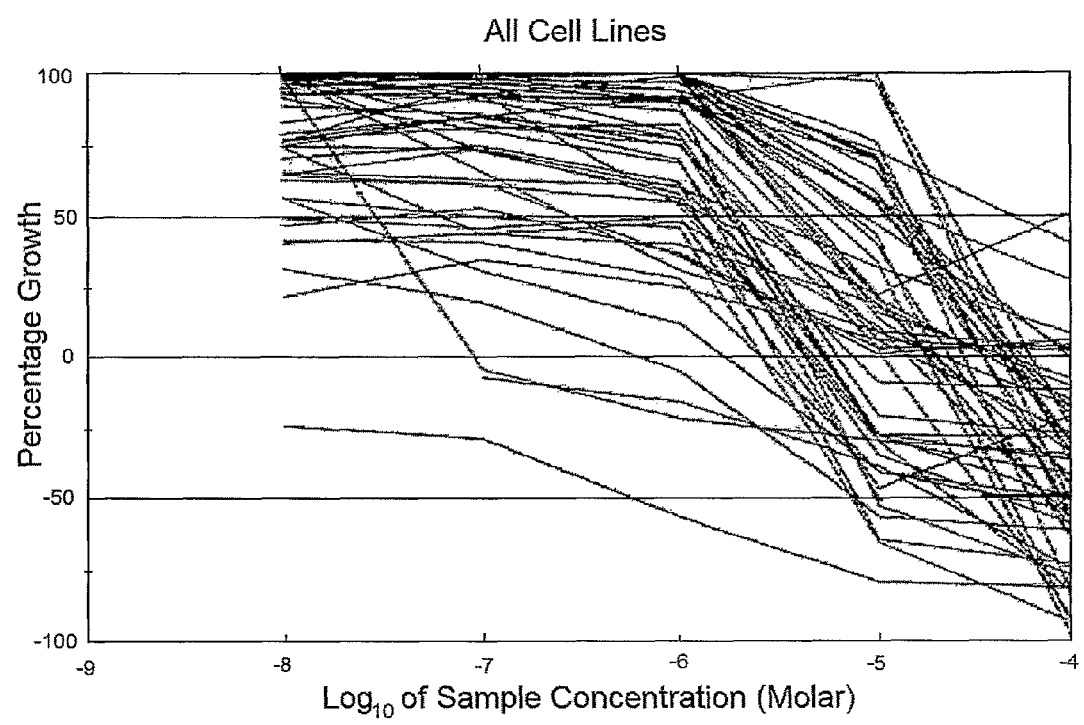
FIG. 18 shows a graph showing National Cancer Institute (NCI) Developmental Therapeutics Program Dose Response Curves for all cell lines tested for Palmerolide E.

Palmerolide E, shown below and in FIG. 15, has the chemical formula $C_{27}H_{39}NO_7$ (for NMR data see FIG. 16). NCI cytotoxicity is shown in FIG. 17A and FIG. 17B. NCI Dose Response Curves for all cell lines are presented in FIG. 18.

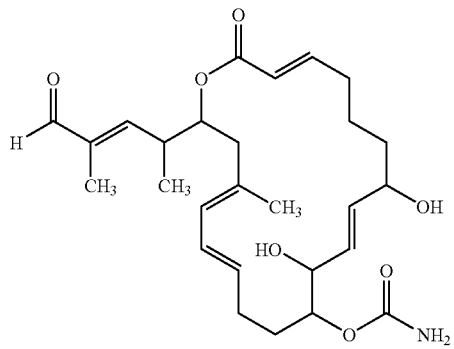 [SMILES: C/C(C=O)=C\C(C)C1C/C(C)=C/C=C/CCC(OC(N)=O)C(O)/C=C/C(O)CCC/C=C/C(=O)O1]

Example VII

Bioassay

Established cell lines (UACC-62, SK-MEL-5 and MK14, which are all sensitive to palmerolide A) have been obtained from the NCI Standard protocols for cell culture are used. UACC-62 (Amundson et al. 2000) and MEL14 (Lin et al., 2003) Cells will be grown in RPMI 1640 medium supplemented with 10% fetal bovine serum and glutamine and treated with antibiotics (100 units/mL penicillin, 100 mg/mL streptomycin) in a humidified atmosphere of 95% air with 5% $CO_2$ at 37° C.

SK-MEL-5 (Miracco et al., 2003). Cells are grown in Eagle's minimal essential medium with Earle's BSS, adjusted to contain 1.5 g/L sodium bicarbonate, 0.1 mM non-essential amino acids and 1.0 mM sodium pyruvate in a humidified atmosphere of 95% air with 5% $CO_2$ at 37° C.

Our bioassays use a 96-well format MTT-based (Vogt et al., 2004) method for the quantification of cell growth inhibition or cell lethality caused by palmerolides and their derivatives. In this assay, metabolically active cells cleave methylthiazol tetrazolium (MTT), which is yellow, to form a purple formazan pigment with a concomitant ultraviolet shift which can be quantified using a plate reader monitoring absorbance at 540 nm n.

Example VIII

Structure Elucidation of Bioactive Metabolites

Upon isolation of a metabolite, it is important to establish the identity of the isolate (dereplication). Inspection of the $^1$H NMR spectrum, in conjunction with mass spectral information from LC/MS and/or ESIMS, can often lead to identification of previously described compounds. Database search and retrieval of marine natural product data greatly assists in dereplication; databases of marine natural products produced by Drs. J. Blunt and M. Munro (Blunt, J. W.; Munro, M. H. G. MarinLit. University of Canterbury, Christchurch, New Zealand, ver 12.4, 2004) and mass spectral libraries from NIST and Wiley are available in this regard. New compounds are subjected to thorough spectroscopic analysis, as described in the Preliminary Data section for Palmerolide A.

Contemporary spectroscopic methods are employed for structure determination of new isolates (Crews et al., 1998; Silverstein et al., 1998). One-dimensional proton and carbon NMR spectroscopy, in conjunction with mass spectral analysis (from LC/MS or electrospray ionization (ESI) or matrix assisted laser desorption ionization (MALDI) mass spectrometers) can secure assignment of the molecular formula of a new compound. Two- and three-bond proton-proton connectivity can be established using a combination of two-dimensional NMR techniques such as COSY (Aue et al., 1976), or extended spin systems with TOCSY (Braunschweiler et al., 1983). Proton-carbon connectivity can be established using HMQC or HSQC (Bax et al., 1986a; Bodenhausen et al., 1980) (one bond) and HMBC (Bax et al., 1986b) (two or three bond). These NMR experiments are most often acquired in gradient (Maudsley et al., 1978; Ruiz-Cabello et al., 1992) mode for maximal sensitivity, using solvent suppression where necessary. If sufficient material is available, carbon-carbon connectivity can be established by obtaining the 2D-INADEQUATE spectrum (Bax et al., 1980); the direct measure of $^{13}C$-$^{13}C$ couplings enable significant portions of the structure to be readily assessed. Stereochemical assignments in conformationally constrained systems are based on coupling constant data and the results of nuclear Overhauser enhancement or NOESY (Crews et al., 1998; Silverstein et al., 1998) techniques where possible, or by derivatization or degradation. Stereochemical analysis of flexible systems (linear or large ring) can be achieved using Murata's method (Murata et al., 1999) of analyzing $^3J_{HH}$ and $^{2,3}J_{CH}$, derived from decoupling and/or ECOSY (Griesinger et al., 1985) ($^3J_{HH}$) or J-resolved HMBC (Furihata et al 1999) ($^{2,3}J_{CH}$), respectively. In the event that spectroscopic methods are not definitive, chemical derivatization and/or degradation techniques can be employed to further clarify the structure or crystals can be grown to facilitate X-ray crystallographic analysis (Yoshida et al., 1995; Anikisetty et al., 2004).

Example IX

Degradative Studies

The palmerolides provide ample functionalization for degradative studies. Reductive ozonolysis of palmerolides A, D, and/or E will lead to three hexane polyols (11-13, Scheme 1). Stereochemical conformation of C-7 in these palmerolides is achieved by comparison of the optical rotation of 11 to that of authentic (R,+)-1,2,6-trihydroxyhexane (Wu et al., 2000).

Positions C-10 and C-11 can be verified by comparison to tetra-ol 12, a compound not reported in the chemical literature. Tetra-ol 12 can be readily prepared from D-galactose (Scheme 2) based on a scheme modeled after the preparation of a similar compound (Zhu et al., 2001). Periodate cleavage of the D-galactose 1,3-acetaldehyde acetal (16) (Dolder et al., 1990), followed by homologation via a Wittig reaction, hydrogenation (Zhu et al., 2001) and hydrolysis will provide the desired 12 for comparison.

Scheme 1: Degradation studies (ozonolysis of parmerolides A (1), D (8) and E (9).

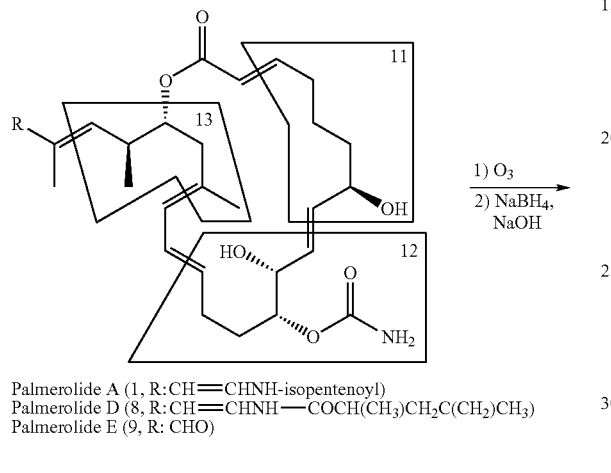

Palmerolide A (1, R:CH═CHNH-isopentenoyl)
Palmerolide D (8, R:CH═CHNH—COCH(CH₃)CH₂C(CH₂)CH₃)
Palmerolide E (9, R: CHO)

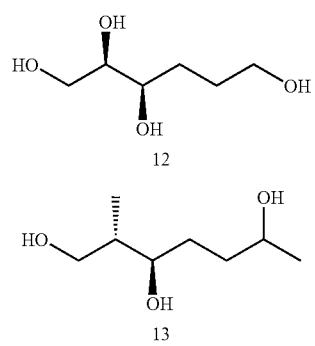

Scheme 2: Synthetic procedures for preparation of (2R,3R)-1,2,3,6-tetrahydroxyhexane (12)

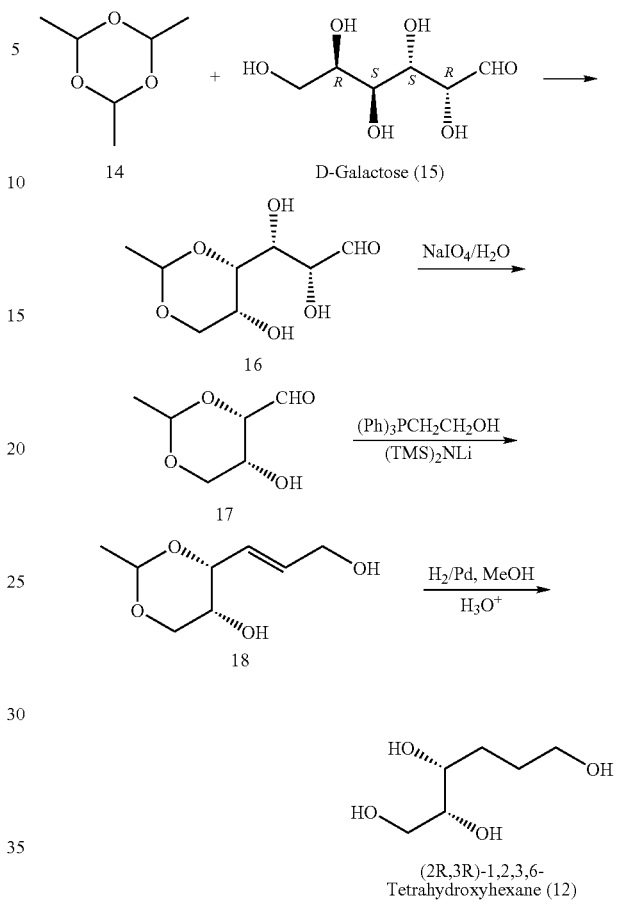

The stereocenters at positions C-19 and C-20 can be confirmed by comparison of compound 13 to a synthetic sample derived via a previously published route (Scheme 3) (Ohi et al., 1999). Chiral induction in the published route was achieved by Sharpless epoxidation of 6-methyl-2,6-hepten-1-ol (19), which was treated with methyl lithium to introduce the methyl group on the opposite face from the alcohol. The published procedure used L-diethyltartrate (L-DET) to achieve the 2S,3S isomer; the subject preparation requires the 2R,3R isomer, so one begins with D-diethyltartrate (D-DET). Protected as the acetaldehyde acetal 22, the C-6 alcohol can be oxidized to the ketone which can be homologated via Wittig reaction, yielding compound 23, which lacks only deprotection to make the comparison sample 21.

Scheme 3.

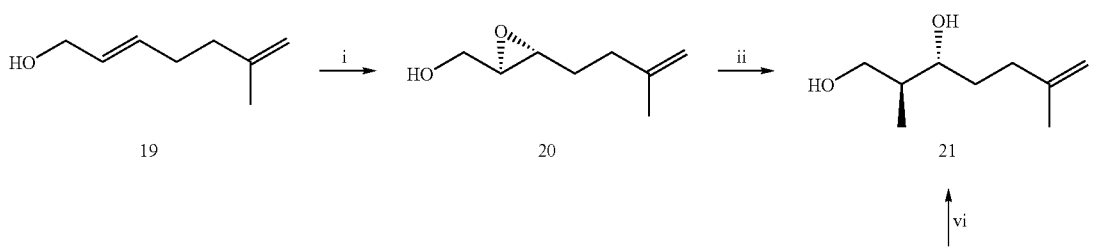

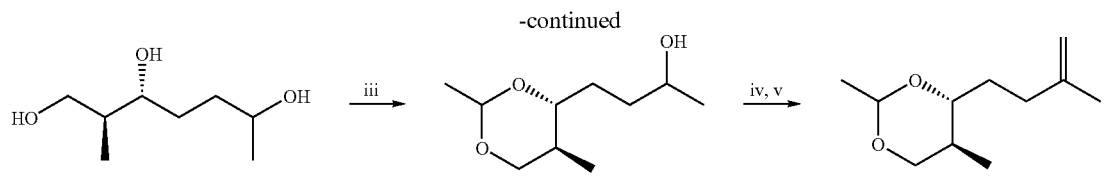

i) Ti(O-i-Pr)$_4$ (0.2 eq), D-DET (0.3 eq), t-BuOOH. ii) CuCN, MeLi, Et$_2$O. iii) 11, TsOH. iv) Swern oxidation (Mancuso et. al., 1981) v) Ph$_3$PCH$_3$, BuLi. vi) TsOH, H$_2$O.

Degradation studies of palmerolides B (6) and C (7) can similarly provide polyols (Scheme 4 and 5). It is expected that C-19 and C-20 stereochemistry will be the same in all the palmerolides, so the ozonolysis products from palmerolides B and C will provide the same product (13) containing those stereocenters. For palmerolide B, two new degradation products (24, 25) result. Both enantiomers of 24 are known, from D- and L-glutamic acid (Brunner et al., 1989; Larcheveque et al., 1984), providing a chiroptical comparison once our assignment has been made. Product 25, with its terminal triol function, is accessible via Scheme 2 techniques, optionally beginning with an alternate sugar, as necessary, and homologation with a C$_3$ Wittig reagent derived from 3-bromopropanol.

-continued

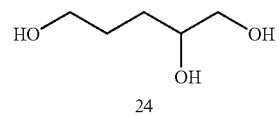

24

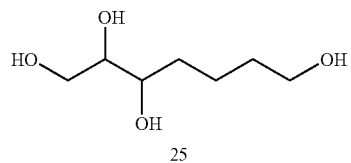

25

Scheme 4. Ozonolysis of palmerolide B (6).

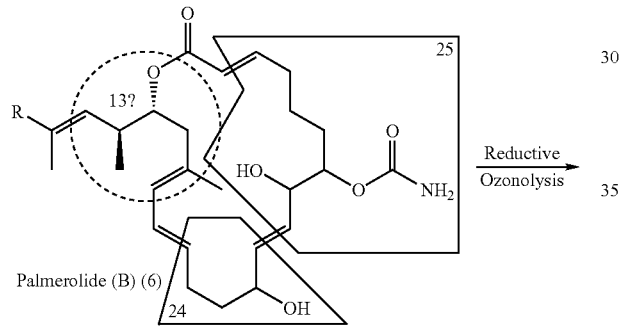

Scheme 5. Ozonolysis of palmerolide C (7).

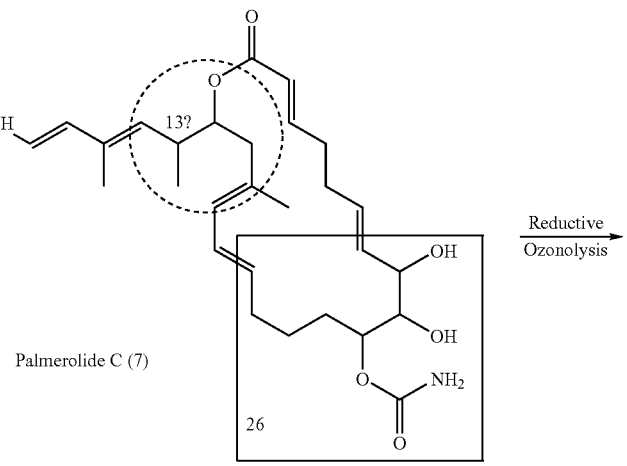

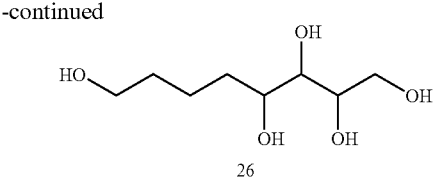

26

Penta-ol 26, derived from reductive ozonolysis of palmerolide C (7) (Scheme 5), is prepared from a precursor chosen from the pool of $C_5$ sugars (Scheme 6), as appropriate to address the stereochemistry determined spectroscopically.

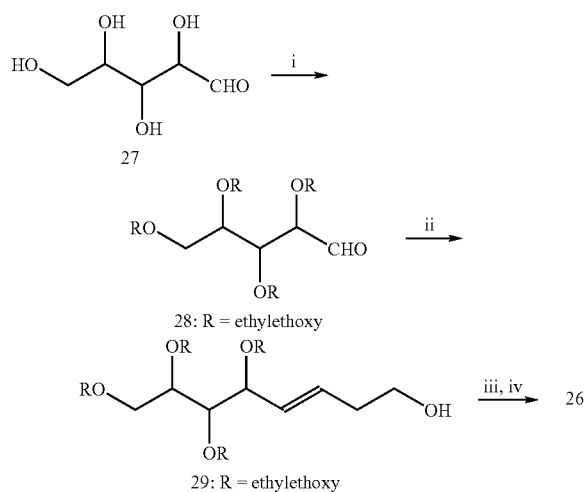

i) Ethyl vinyl ether, PPTS, $CH_2Cl_2$. ii) $Ph_3PCH_2CH_2CH_2OH$, $(TMS)_2NLi$. iii) $H_2/Pd$. iv) 1 N HCl, rt.

Schemes 1 through 6 summarize our degradative structure proofs of palmerolide A-G stereochemistry. As new palmerolides are isolated they can be treated accordingly to confirm all stereochemical assignments.

Example X

Structure-Activity Studies of Palmerolides

The palmerolides exert their melanoma activity by inhibition of vacuolar adenosine triphosphatases (V-ATPases). These are multi-protein trans-membrane enzymes responsible for translocation of protons out of the cytoplasm, resulting in pH regulation of intracellular compartments, a critical function for homeostasis (Sun-Wadaa et al., 2004). They are ubiquitous in eukaryotic cells and found occasionally in prokaryotes. The two domains of the enzyme are each composed of roughly half a dozen subunits and ultimately comprise a 20-protein assemblage. The $V_O$ domain, which is imbedded in the membrane, is the locus of proton transfer while the sub-membrane VI domain bears catalytic (ATP to ADP) activity (Nishi et al., 2002). In addition to pH regulation, V-ATPases play a role in endocytosis, membrane fusion (Morel et al., 2003), bone resorption (Nomiyama et al., 2005) and other functions which are not simply functions of acidity (Nishi et al., 2002). However, they may have specialized roles in cancer-regulatory pathways involved in cell growth, differentiation (Martinez-Zaguilan et al., 1993) angiogenesis (Martinez-Zaguilan et al., 1999a), multidrug-resistance (Laurencot et al., 1995; Raghunand et al., 1999; Martinez-Zaguilan et al., 1999b; Sennoune et al., 2004) and metastasis (Martinez-Zaguilan et al., 1998).

Structural studies on V-ATPases which may lead to a better understanding of ligand/receptor interactions include NMR studies of the F subunit (Jones et al., 2001) and more recent X-ray data (Murata et al., 2005) on the K ring subunit of prokaryotic V-type $Na^+$-ATPase, which is homologous to the c/c'/c" ring of eukaryotic $H^+$ V-ATPases. The significance of this X-ray data is that known inhibitors of $H^+$ V-ATPases bind the c subunit (Pàli et al., 2004; Huss et al., 2002), holding the promise of X-ray data on ligand/receptor binding of an inhibitor.

V-ATPases have been implicated in a number of disease states, including type 1 diabetes (Myers et al., 2003a; Myers et al., 2003b), osteoporosis (Nomiyama et al., 2005; Sundquist et al., 1990) and several cancers (Sennoune et al., 2004) such as cervical (Ellegaard et al., 1975), breast (Martinez-Zaguilan et al., 1999b) and melanoma (Martinez-Zaguilan et al., 1998). Metastatic breast cancer cells have been demonstrated to show significant increases in the number of V-ATPase enzymes on their plasma membranes (Martinez-Zaguilan et al., 1993; Sennoune et al., 2004). Cancer cells require low pH cytoplasm and depend largely on V-ATPases to maintain that acidity (Martinez-Zaguilan et al., 1993; Raghunand et al., 1999)

Bafilomycin $A_1$ (4, FIG. 3) is the prototypical V-ATPase inhibitor (Zhang et al., 1994) although its binding and specificity are not nearly as great as more recently discovered inhibitors such as salicylihalamides (vis 5) (Erickson et al., 1997; Boyd et al., 2001) oximidines (Kim et al., 1999), lobatamides (McKee et al., 1998; Shen et al., 2002) and palmerolides. Besides bafilomycins, the concanamycins (Huss et al., 2002), are similarly configured macrocycles while the poecillastrins and chondropsins (Xie et al., 2004) are considerably larger macrolides comprised of, in addition to a lactone linkage, a lactam linkage.

(4)

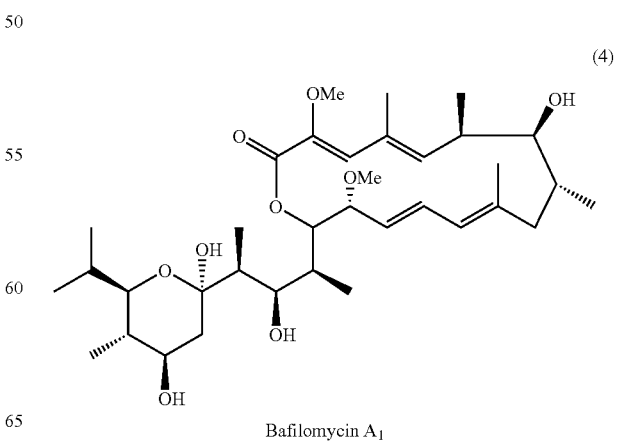

Bafilomycin $A_1$

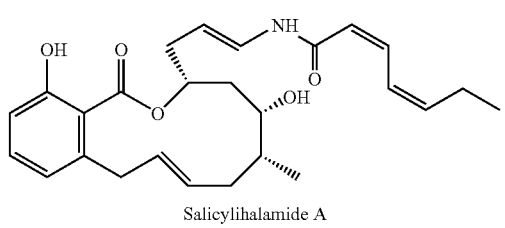

Salicylihalamide A

Scheme 7: Natural product diversity based on structure-activity profile

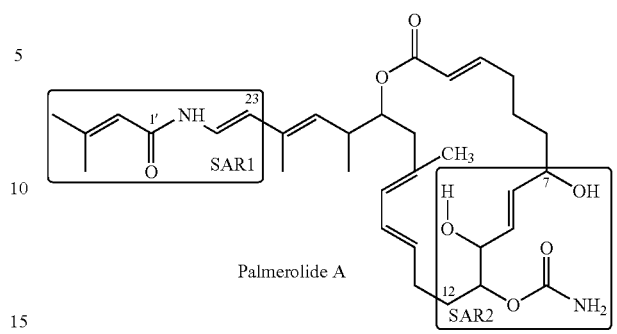

Palmerolide A

V-ATPase inhibitors are poised to become a new target of cancer intervention (Chene et al., 2003; Beutler et al., 2003). Key discoveries leading to first-in-class drugs, such as taxol was for inhibition of tubulin depolymerization (Horwitz et al., 2004), ultimately lead to a proliferation of drugs for the indication and greatly enhance treatment options. Histone deacetylase (HDAC) inhibitors (Arts et al., 2003) are similarly undergoing a serge in interest as the Food and Drug Administration (FDA) has recently approved several Investigational New Drug (IND) applications. Among several potent V-ATPase inhibitors now known it is expected that one will soon emerge as a model to move forward for ED approval.

The subject functional group manipulation approach begins with the 'Rule of 5' principles elaborated by Lipinski et al., 2001 to address Absorption, Distribution, Metabolism, Excretion and Toxicity (ADMET) issues. Among Lipinski's Rules, palmerolides already hold up well: there are 5 or fewer H-bond donors, M Log P is approximately 1.8 to 2.76 (calculated using SimulationsPlus, Inc. (Lancaster, Calif.) ADMET Predictor software) and there are less than 10 H-bond acceptors. The molecular weights are a bit high, spanning the mid-500's to 610; palmerolide E is the only member less than 500, but it lacks the vinyl amide required for V-ATPase activity. Refining our approach with ADMET Predictor, it is clear that solubility and permeability are areas to focus derivatization studies and the two appear to track in opposing trends. Thus, solubility improves with the addition of polar functional groups while permeability improves with removal of polar functional groups. Reconciliation of this dichotomy will take place in the biological evaluation: compounds prepared according to teachings herein can be evaluated for melanoma and/or V-ATPase activity, as described above, and those retaining sufficient bioactivity (sub-millimolar) and displaying promising ADMET properties (based on evaluation by ADMET Predictor) can be subjected to the hollow fiber and/or xenograph assays.

Loss of the C-24 amide results in reduced activity and one alternate arrangement of the C-6 through C-12 hydroxylation/olefination pattern also results in similarly reduced activity, proven by the palmerolides C (7) and E (9), which have undergone NCI 60 cell line bioassay. Other palmerolides can be similarly assayed.

For chemical derivatization studies, the palmerolide gross structure will be divided into three areas of interest: (1) the C-24 terminus and the associated vinyl amide (SAR1 region, Scheme 7); (2) the hydroxylation/olefination juxtaposition at C-7 through C-12 (SAR2 region, Scheme 7); and (3) the group of olefins, which can be manipulated chemically.

Derivatization studies can be conducted to increase polar groups in each region, to decrease polar groups in each region, and to make modifications without changing the number of polar groups. Permutations of polar group manipulations on different parts of the core structure lead to other possible modifications. As biological data accumulates, one selects the desired bioactivity profiles (potency and ADMET Predictor properties), rather than merely generating large numbers of derivatives. Described below are manipulations focused by area as well as manipulations to add, remove, or leave unchanged, the number of polar groups.

i. The SAR1 Region

The region designated as SAR1 can be evaluated by at least four natural products. Palmerolides A (1), D (8), E (9) and F (10) differ only in the nature of the terminus of the palmerolide parent chain. Synthetic modifications to be introduced to further probe the C-24 terminus can include the following chain terminating groups:

Retention of Polar Functional Groups:

Non-Conjugated:

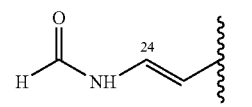

30

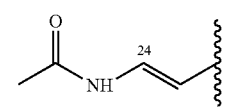

31

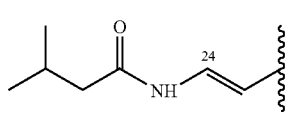

32

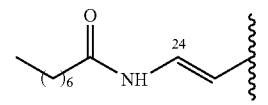

33

Conjugated:

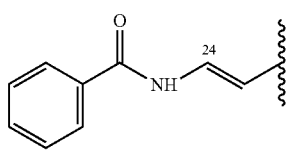

34

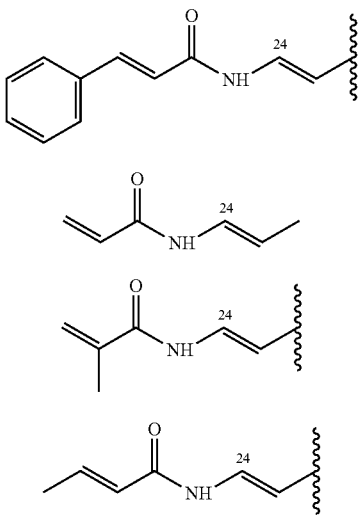

Reduction in the Number of Polar Groups:

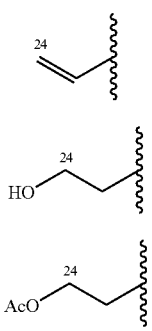

Addition of Polar Functional Groups:
Non-Conjugated:

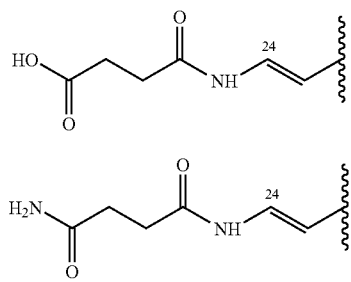

Conjugated:

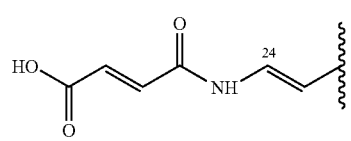

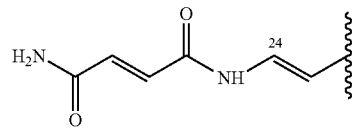

Preparation of derivatives 30 to 45 can be accomplished by the copper-catalyzed vinyl amidation reaction (Scheme 8) (Shen et al., 2000). High yields of stereocontrolled E vinyl amide analogues of palmerolides can be prepared by coupling of the desired amide with a vinyl iodide 46 using copper (I) thiophenecarboxylate (CuTC) as catalyst.

Scheme 8.

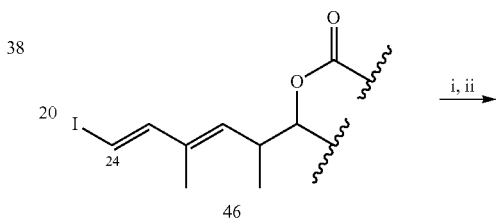

46

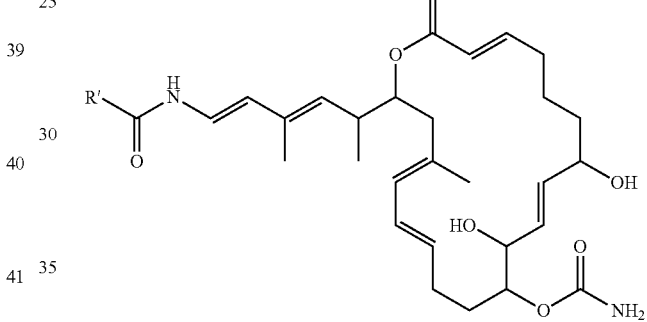

30-45 i: CuTC, N,N'-dimethyl-ethylenediamine, $K_2CO_3$, 50° C., R'CONH$_2$.
ii: HF•pyridine/pyridine.

The necessary E-vinyl iodide 46 can be prepared in one of two ways. The most direct route involves chromium-catalyzed (Takai olefination, Takai et al., 1986) homologation of tri-t-butylsilyl-protected palmerolide E (vis 47, Scheme 9). Note that since functionalization of the palmerolides is not unlike that of discodermolide (Gunasekera et al., 1990), their stability to conditions described herein can be verified by synthetic procedures applied to discodermolide as are well known in the art (Paterson et al., 2001; Smith et al., 2000).

Scheme 9.

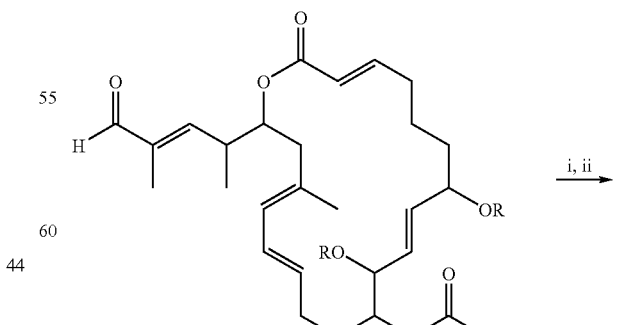

Palmerolide E (9): R = H
47: R = TBS

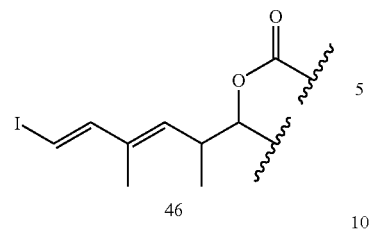

46 i: TBSCl, imidazole. ii: CHI₃, CrCl₂, THF, 0° C.

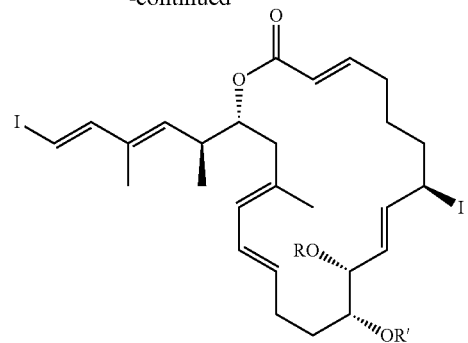

49 i) TBSCl, imidazole. ii) tetrachlorophthalic anhydride, Δ. iii) a. hydrazine, b. TsOH/H₂O. iv) hydrazine. v) I₂, DBU Alternately, vinyl iodide 46 can be prepared from Palmerolide A; while more steps are involved, this may be desired since Palmerolide A is more predominant in the tunicate. Thus, palmerolide A can be suitably protected (Scheme 10) to differentiate the C-7 and C-10 oxygen functions from the C-11 oxygen function, then the amide selectively hydrolyzed (Eaton et al., 1988) and the resultant phthalimide hydrolyzed to produce aldehyde 48. Aldehyde 48 is amenable to direct conversion to the vinyl iodide using Danishefsky's method (Di Grandi et al., 1993), the latter of which produces a vinyl iodide directly from a ketone. The thermodynamically E vinyl iodide (49) results. The Carbamate hydrolyzes under the conditions employed; the p-methoxybenzyl ether (PMBO (C=NH)CCl₃, PPTS) (Nakajima et al., 1988) protecting group is used for that position, to distinguish it in future procedures from the C-7 and C-10 oxygenated functions.

If the Danishefsky method (Scheme 9) is undesirable, one can employ degradation of the aldehyde (48) to the protected palmerolide E (47, R=PMB) via Baeyer-Villiger oxidation, hydrolysis of the resultant formyl ester, then Dess-Martin oxidation (Dess et al., 1991) to the aldehyde (Scheme 11). Intermediate 47 can then be elaborated into the desired vinyl iodide 46 as shown in Scheme 9. Note that Baeyer-Villiger reagents such as those employing Lewis-acid catalysis of trimethylsilylperoxide can often be accomplished in the presence of olefins without fear of epoxidation (Brink et al., 2004).

Scheme 10.

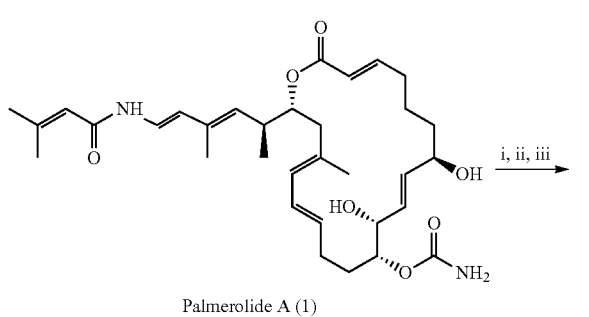

Palmerolide A (1)

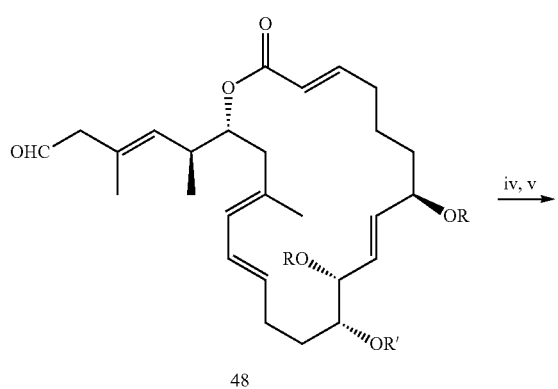

48

Scheme 11.

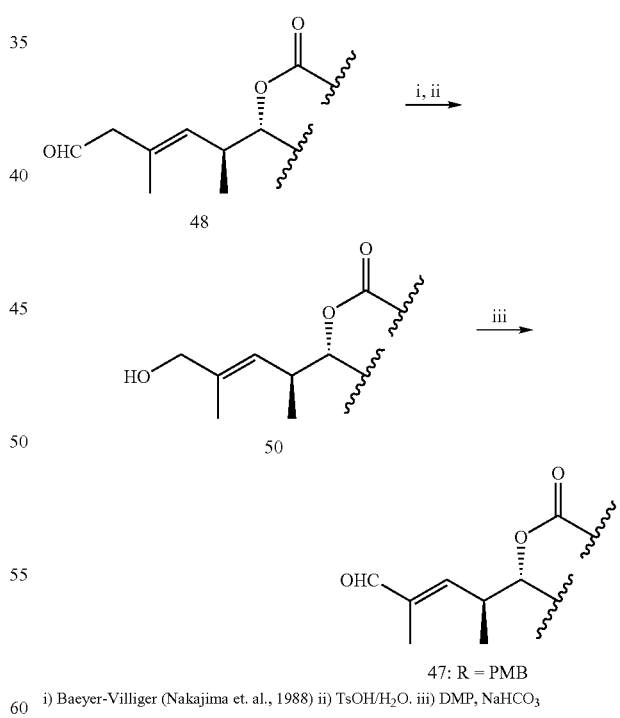

47: R = PMB i) Baeyer-Villiger (Nakajima et. al., 1988) ii) TsOH/H₂O. iii) DMP, NaHCO₃

Palmerolide analogues 39-41 can be prepared from the Wittig reaction of protected palmerolide E (47) with methyl triphenyl-phosphonium bromide/BuLi (yielding 39), NaBH₄/CoCl₂ reduction of hydroxymethyl derivative 48 (yielding 40) or acetylation of 40 (yielding 41).

ii. SAR2 Region

The C-7 to C-12 SAR2 region can be probed by natural products including palmerolides A (1), B (6) and C (7), which differ only in the SAR2 region. Palmerolide C is less potent than palmerolide A. Further synthetic derivatizations can assess the role of the alcohol groups based on modification of template 51 by retention, reduction and addition of polar functional groups. Alternate modifications are readily obtained.

SAR2 Modification Template 1 (51)
Retention of Polar Functional Groups:

|     | $R_1$ | $R_2$ | $R_3$ |
|-----|-------|-------|-------|
| 52: | p-OH Bn | H | $CONH_2$ |
| 53: | H | p-OH Bn | $CONH_2$ |
| 54: | p-OH Bn | p-OH Bn | $CONH_2$ |
| 55: | H | H | H |
| 56: | H | H | p-OH Bn |
| 56A: | $(CH_3)_2CHCHNHCO$ | H | $CONH_2$ |
| 56B: | $(CH_3)_2CHCHNHCO$ | $(CH_3)_2CHCHNHCO$ | $CONH_2$ |

Reduction of Polar Functional Groups:

|     | $R_1$ | $R_2$ | $R_3$ |
|-----|-------|-------|-------|
| 57: | Me | H | $CONH_2$ |
| 58: | H | Me | $CONH_2$ |
| 59: | Me | Me | $CONH_2$ |
| 60: | H | H | Me |
| 61: | =O | H | $CONH_2$ |
| 62: | H | =O | $CONH_2$ |
| 63: | $CONH_2$ | H | $CONH_2$ |
| 64: | H | $CONH_2$ | $CONH_2$ |
| 65: | $CONH_2$ | $CONH_2$ | $CONH_2$ |

SAR2 Modification Template 2 (66)
Addition of Polar Functional Groups (Template 2):

|     | $R_1$ | $R_2$ | $R_3$ |
|-----|-------|-------|-------|
| 67: | $CONH_2$ | H | $CONH_2$ |
| 68: | H | $CONH_2$ | $CONH_2$ |
| 69: | $CONH_2$ | $CONH_2$ | $CONH_2$ |

Preparation of Derivatives 52-69:

Reaction at C-7 precedes reaction at C-10 (Diyabalanage et al., 2006). Thus C-7 mono-derivatized compounds will be prepared directly. C-10 mono-derivatives will be prepared by a protection/deprotection of C-7 (tri-t-butylsilyl ether) sequence. The des-carbamato (55) reaction is described in Scheme 10; suitably protected C-7 and C-10 alcohols will provide access to modification of C-11. Carbamates can be interchanged among C-7, C-10 and C-11 ($Cl_3CC(O)NCHO$, then $K_2CO_3$) (Kocovsky 1986) if warranted by bioactivity profiles of the acetates 63-65). Valine esters 62 and 63 are modeled after the similar valaciclovir prodrug, which demonstrated significantly improved pharmacodynamic properties (Guglielmo et al., 2004). Compounds 67 to 69 can be prepared from osmimum tetroxide dihydroxylation of 63-65 (forming diastereomeric products such that two products from each of 63 to 65 will result, after separation).

iii. Role of the Olefins

Finally, evaluation of the role of the olefin functions takes advantage of selective hydrogenation catalysts. Perhydrogenation, resulting in 70, is achieved by treating Palmerolide A with $H_2$, Pd/C, while nickel boride provides a selective hydrogenation of disubstituted olefins (71) (Choi et al., 1996). Selective reduction of the olefin involved in the α,β-unsaturated carbonyls (vis 72) can be achieved with 10% Pd/C and ammonium formate (Ram et al., 1992). Selective reduction of the lone non-conjugated olefin (73) can be achieved by a number of hydrogenation techniques, such as with the borohydride exchange resin/$Ni_2B$ catalyst (Yoon 1996). These derivatives of palmerolide A, in addition to other palmerolide natural products, which would yield different hydrogenation products, provide evidence as to the role of olefins in the bioactivity profiles of the palmerolides.

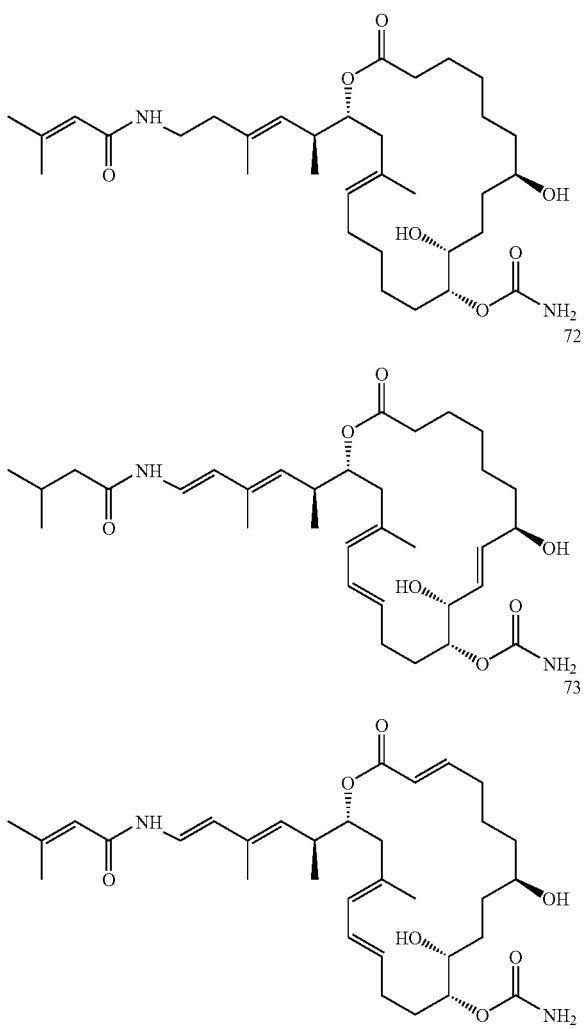

iv. Combinations of Derivatization

Modifications described for SAR1, SAR2 and/or hydrogenation can readily be combined if desired by bioactivity profiles and/or ADMET Predictor simulations.

The total synthesis of natural products is a major tool in the determination of the unambiguous structure of a compound. Total synthesis also serves as a successful strategy for the formation of analogues of the natural product by simple variation of starting materials or reactions in the synthetic scheme. Our proposed synthetic studies toward the palmerolides detail a convergent approach whereby each component can be varied to provide analogues inspired by X-ray co-crystallization studies with V-ATPase and by computational predictions using ADMET. The synthesis will also be used to confirm the structure and absolute stereochemistry of the palmerolides. This is especially important for less abundant palmerolides such as palmerolide D, E, and F due to the trace quantities that can be isolated.

The synthesis is loosely based upon fragments that could be obtained from the degradation studies (shown earlier) using the reductive ozonolysis of palmerolide A. With the degradative studies in mind we devised a retrosynthetic analysis of palmerolide A (Scheme 12). Our retrosynthesis divides the molecule into 3 major segments. The macrocylcic core of palmerolide A should be easily formed by a ring-closing metathesis of the precursor 76 (Grubbs et al., 1995). The metathesis precursor 76 could be formed from the esterification of alcohol 77 with 78. Fragments 79 and 80 could reasonably be coupling partners for a Heck reaction to produce the desired alcohol fragment 77 (Harris et al., 1996). Amide 80 could be inserted into the C-21 side chain by means of a copper-catalyzed amidation reaction directly related to work the Co-PI helped develop (Shen et al., 2000; Klapars et al., 2001; Jiang et al., 2003). The vinyl iodide 82 required for the amidation reaction could be synthesized by employing the Takai olefination of the corresponding aldehyde precursor. (Takai et al., 1986) The C-22 double bond could, in turn, be formed by using the Schlosser modification of the Wittig reaction. (Schlosser et al., 1966) This should lead to selective formation of the (E)-alkene. The stereochemistry of C-20 and C-21 could be established by means of the highly predictive diastereoselective aldol reaction that was developed by Evans. (Evans et al., 1981) The chiral diol 79 could, in turn, be prepared enantioselectively using the Sharpless asymmetric dihydroxylation (Jacobsen et al., 1988). The asymmetric dihydroxylation could also be employed to form the chiral alcohol fragment 78. This leads to the enantioselective formation of the chiral secondary alcohol on C-8. The vinylogous ester in fragment 78 may be prepared by a Horner-Wadsworth-Emmons olefination reaction (Stocksdale et al., 1998).

Scheme 12. Retrosynthetic analysis of palmerolide A (1)

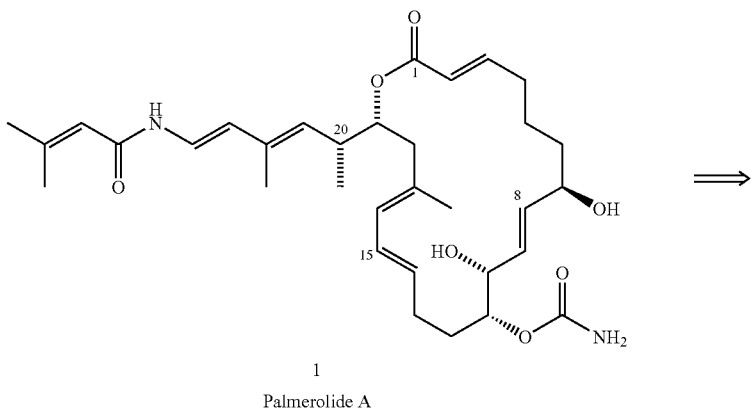

1
Palmerolide A

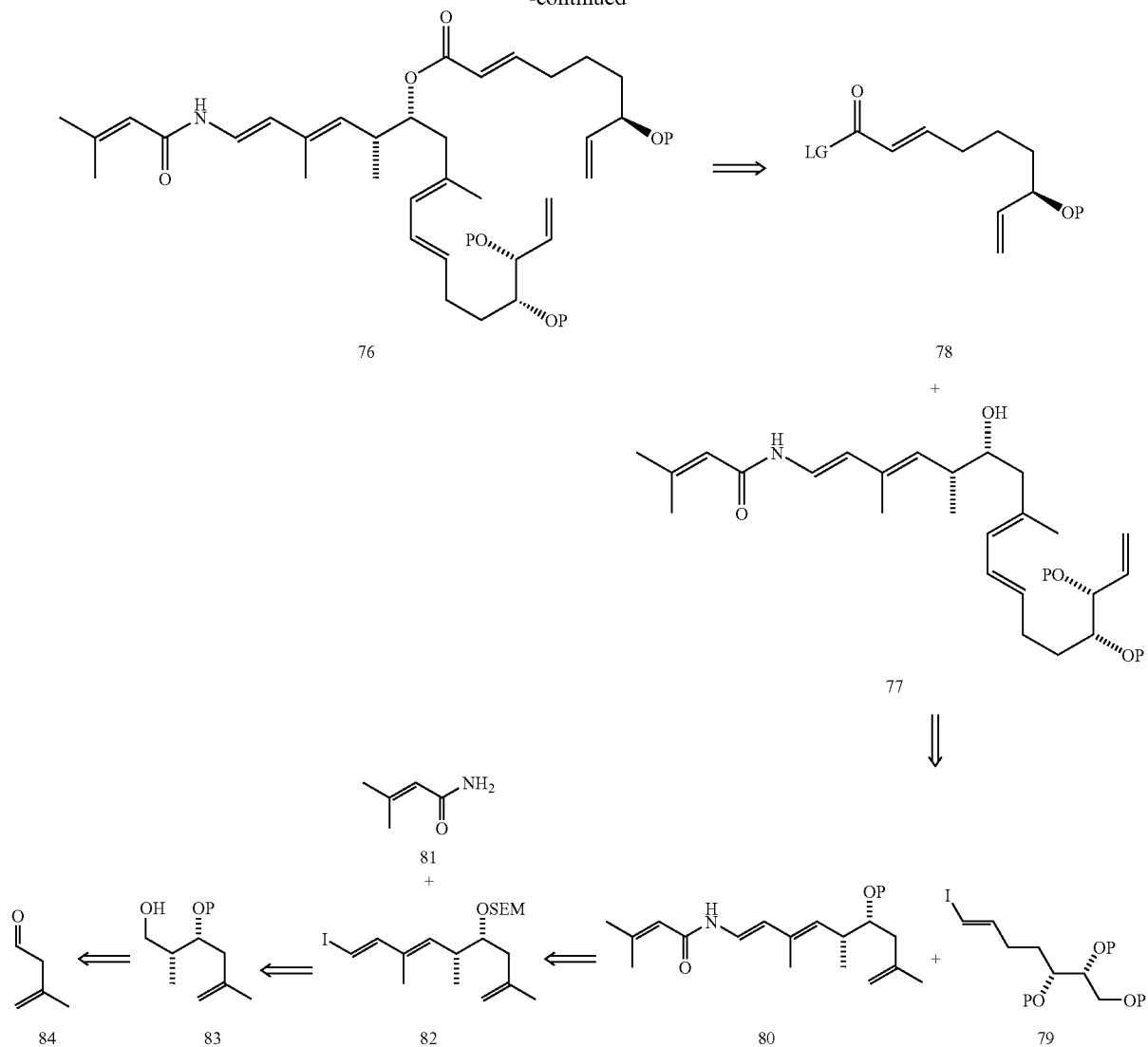

The synthesis of palmerolide A begins with the construction of fragment 79. Commercially available alkynyl alcohol 85 (Scheme 13) is protected as the TBDPS ether by treating the alcohol with imidazole and TBDPS-Cl in a known procedure (Hanessian et al., 1975). Treatment of alkyne 86 with paraformaldehyde and n-BuLi results in the previously known formation of propargylic alcohol 87 (Nicolaou et al., 1989). The treatment of 87 with Red-Al (Sodium bis(2-methoxyethoxy)aluminium hydride) should result in the formation of the known E-substituted allylic alcohol 88. Asymmetric dihydroxylation of 88 with Sharpless conditions should lead to the formation of desired diol 89 with high enantioselectivity (Jacobsen et al., 1988). It should be noted at this point that the Sharpless asymmetric aminohydroxylation could be employed at this stage of the synthesis (Li et al., 1996). This would lead to the formation of an enantiopure 1,2-amino alcohol. The amide nucleophile generally prefers the less hindered carbon of the alkene. Based upon that observation, the protected amine should be installed on C-11 of palmerolide A. This aminohydroxylation route could provide an aza variant of palmerolides. The two secondary alcohol groups of compound 89 can be selectively protected as an acetonide upon treatment with acetone and TsOH (Coe et al., 1989). This would protect the two secondary alcohols in favor of the primary alcohol due to the thermodynamic stability of the product. At this point, the primary alcohol in 90 can be protected with a TIPS group (Cunico et al., 1980). The acetonide could then be opened with FeCl$_3$ and SiO$_2$ in chloroform (Kim et al., 1986). This should open the acetonide and not affect the silyl protected alcohols. The secondary alcohol on C-12 can now be protected with TBS-Cl and imidazole. (Corey et al., 1972) The C-12 alcohol protection should be the major product due to the bulk of the TIPS protecting that is present on the C-10 hydroxyl group. The C-11 alcohol can now be protected with MOM-Cl, NaH in THF (Kluge et al., 1972). The ability to protect all of the hydroxyl groups with different protecting groups is vital to this study because it allows for our main goal, the derivatization of palmerolide A. The aldehyde 92 can be prepared by selectively deprotecting the TBDPS group followed by oxidation with Dess-Martin periodinane (Dess et al., 1983). The aldehyde can then be converted to vinyl iodide 93 via Takai olefination (Jiang et al., 2003). This olefination procedure forms the (E)-vinyl iodide selectively. This vinyl iodide would have the correct stereochemistry required for the Heck reaction later in the synthetic route Scheme 13.

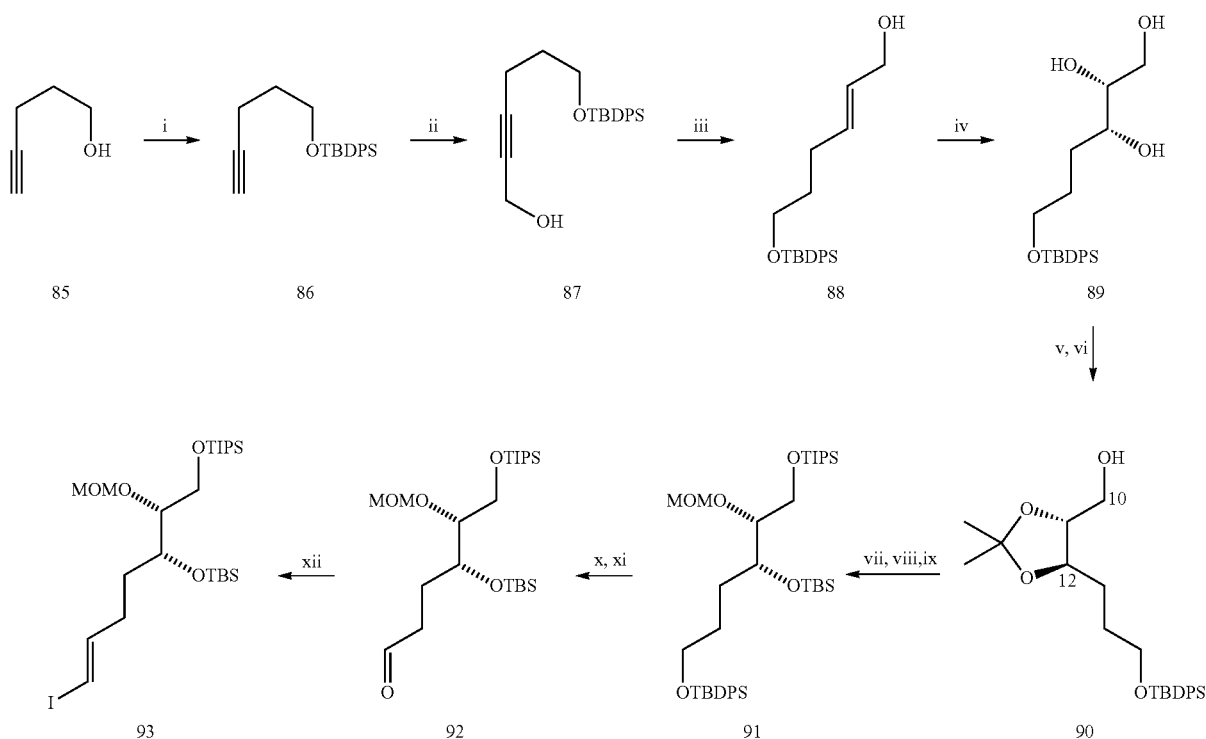

i) TBDPSCl, imidazole, DMF. ii) BuLi, (CH$_2$O)$_n$, THF. iii) Red-Al, Et$_2$O. iv) AD-mix β, t-BuOH/H$_2$O. v) Acetone, TsOH. vi) TIPS-Cl, pyrdine. vii) FeCl$_3$/SiO$_2$, CHCl$_3$. viii) TBS-Cl imidazole, DMF. ix) MOM-Cl, NaH, THF. x) 5 N NaOH, EtOH. xi) Dess-Martin periodinane, DCM. xii) CHI$_3$, CrCl$_2$, THF, 0° C.

The next major step in the synthesis of palmerolide A is the preparation of fragment 78 from the retrosynthesis. The synthesis of 78 begins with the oxidation of 94 (Scheme 14) with Dess-Martin periodinane (Dess et al., 1983). Sharpless asymmetric dihydroxylation of the alkene would lead to the enantioselective formation of diol 95 (Jacobsen et al., 1988). The primary alcohol would be selectively protected with TBDPS-Cl and imidazole (Hanessian et al., 1975). The secondary hydroxyl group can be converted to SEM ether 96 with SEM-Cl and DIPEA in dichloromethane (Lipshutz et al., 1980). The formation of 97 can be accomplished by a Horner-Wadsworth-Emmons olefination reaction (Stocksdale et al., 1998). This would be followed by the deprotection of the TBDPS group with 5 N NaOH in EtOH and oxidation of the alcohol with Dess-Martin periodinane, giving compound 98 (Dess et al., 1983). Petassis olefination of the aldehyde functional group would give olefin 99 (Petassis et al., 1990). Reduction of the ester functional group in compound 99 with DIBAL would give aldehyde 100 (Sunazuka et al., 2000). Oxidation of the aldehyde under Jones oxidation conditions would lead to the formation of carboxylic acid 101 (Bowden et al., 1946). Compound 101 could be used directly to form the ester bond later in the synthesis. However, conversion of the acid to the acid chloride with oxalyl chloride 102 would lead to a milder esterification.

Scheme 14.

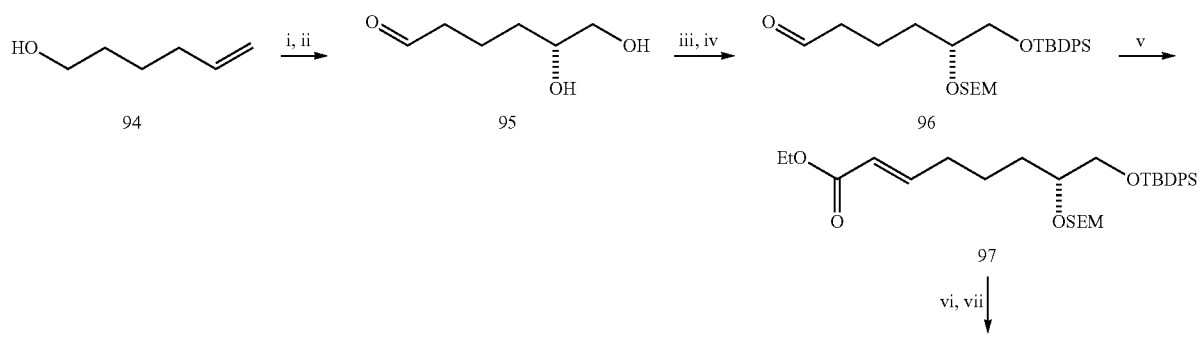

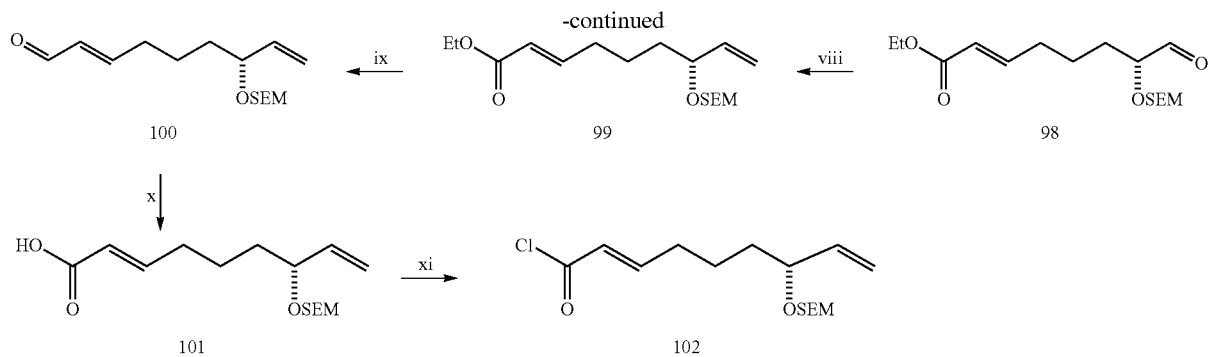

i) Dess-Martin periodinane, DCM. ii) AD-mix β, t-BuOH/H₂O. iii) TBDPS-Cl, imidazole, DMF. iv) SEM-Cl, DIPEA, DCM. v) Triethylphosphonoacetate, KHMDS, 18-crown-6, toluene vi) 5 N NaOH, EtOH. vii) Dess-Martin periodinane. viii) Cp₂Ti(Me₂), THF, reflux. ix) DIBAL-H, Et₂O. x) NaClO₂, NaH₂PO₄, 2-methyl-2-butene, t-BuOH. xi) (COCl)₂, Benzene.

The last fragment of the molecule that needs to be prepared is the C-17 through C-25 amide side chain. The first step (Scheme 15) in the synthesis of this fragment is the PDC oxidation of the commercially available geraneol, to yield 103. (Reiter et al., 2003). The use of Evans diastereoselective Aldol condensation at this point would allow for the formation of the 104 (Evans et al., 1981). This Evans methodology has proven to be one of the most dependable tools available to a synthetic chemist for the formation of syn-selective Aldol products. The R group of the oxazolidinone can be varied in order to obtain the product with the highest diastereomeric excess. Protection of the alcohol in compound 104 leads to the formation of 105 (Lipshutz et al., 1980). The oxazolidinone auxiliary will then be removed by exposure of 105 to NaOMe in MeOH to lead to the formation of ester 106 (Evans et al., 1981). The reduction of ester 106 with LiAlH₄ followed by subsequent bromination with PPh₃ and Br₂ should lead to the formation of bromide 107 (Wiley et al., 1964). The use of the Schlosser variant of the Wittig reaction of 107 with 108 should lead to the exclusive formation of (E)-alkene 109 (Schlosser et al., 1966). Compound 109 could then be subjected to the synthetic sequence in Scheme 16 followed by deprotection of the acetal. This would allow for the synthesis of palmerolide E. Deprotection of the acetal followed by Takai olefination would lead to compound 110 (Takai et al., 1986; Hagiwara et al., 1987). Copper-catalyzed coupling of the vinyl iodide with the necessary amide would provide 111 (Shen et al., 2000; Klapars et al., 2001; Jiang et al., 2003). Variation of the amide employed in this coupling could lead to the synthesis palmerolides D and F.

Scheme 15.

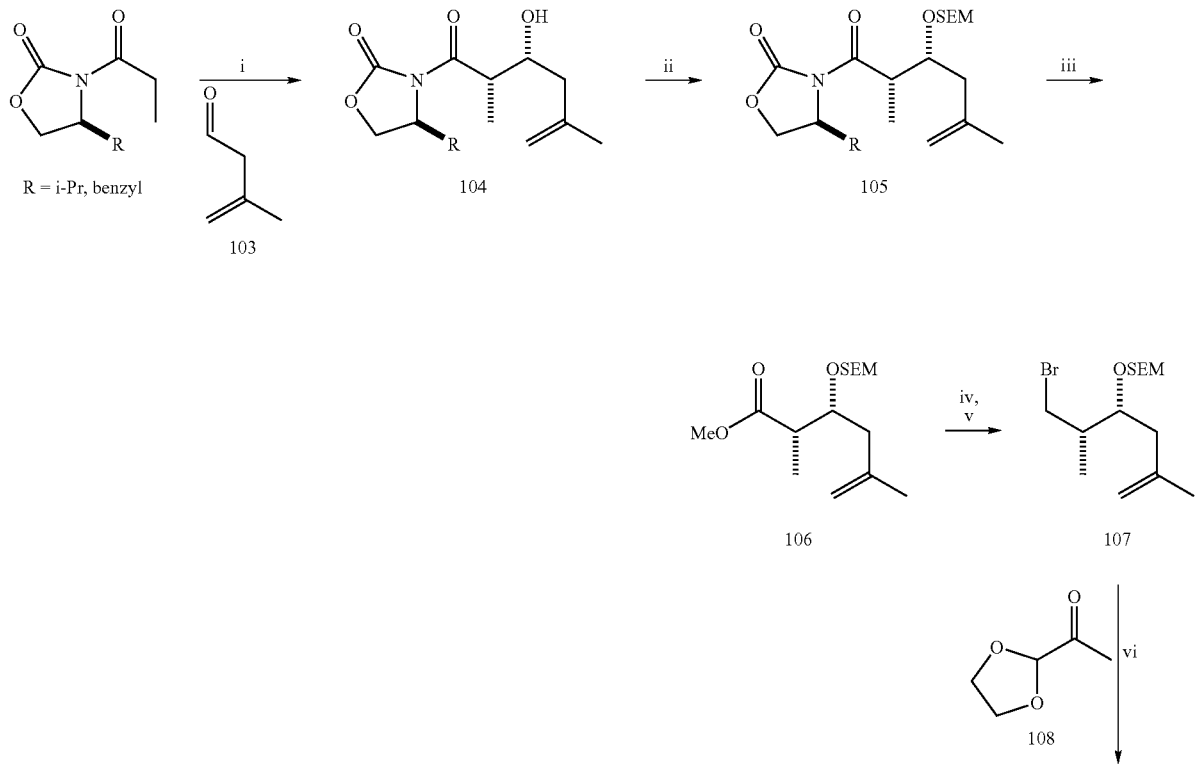

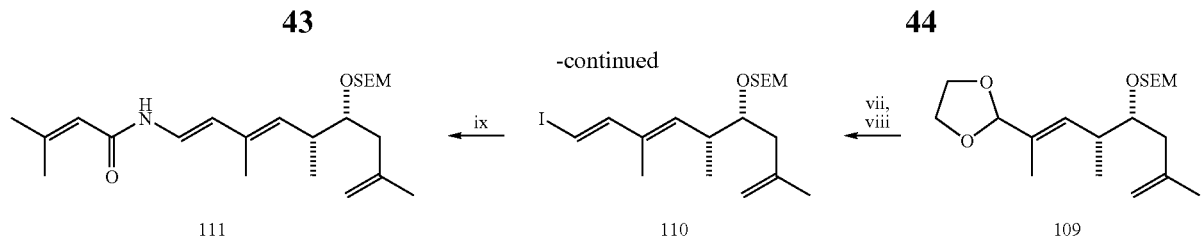

i) a) Bu₂BOTf, DIPEA, DCM, 0° C. then add 103, -78 to 0° C. b) MeOH/30% H₂O₂. ii) imidazole, SEM-Cl, DMF. iii) NaOMe, MeOH. 0° C. iv) LiAlH₄, Et₂O. v) PPh₃, Br₂, Triglyme. vi) PPh₃, PhLi, LiBr, Et₂O, toluene, then add 108. vii) PPTS, acetone, H₂O, Δ. viii) CHI₃, CrCl₂, THF, 0° C. ix) amide, CuTC, N,N′-dimethyl-ethylenediamine, K₂CO₃, 50° C.

The final stages of the synthesis of palmerolide A would begin (Scheme 16) with a Heck coupling of vinyl iodide 93 and alkene 111, which should result in the formation of diene 112 (Harris et al., 1996). Deprotection of the TIPS group followed by subsequent Petasses olefination would provide compound 113 (Petassis et al., 1990). We are favoring the use of Petassis olefination due to the methods ability to tolerate the presence of the functional groups present in compound 112. Deprotection of the SEM group in compound 113 followed by subsequent esterification with compound 101 should lead to the formation of 114 (Schlessinger et al., 1986). Ring-closing metathesis of 114 using the second-generation Grubbs catalyst could lead to the formation of macrocycle 115 (Grubbs et al., 1995). It has been observed that the metathesis reaction has been used successfully to close a macrocycle in the synthesis of natural products with structural similarities to palmerolide A. For example, the RCM approach in the epothilone family of natural products tends to favor the formation of the (E)-double-bond (Meng et al., 1997). Formation of carbamate 116 may be accomplished by treatment of 115 with isocyanic acid and CuCl (Duggan et al., 1989). The final step in the synthesis of palmerolide A is the global deprotection of the remaining protecting groups with MgBr₂ and BuSH in Et₂O (Kim et al., 1991). This is a mild deprotection procedure that should not open the lactone or cleave the carbamate functional groups present.

Scheme 16.

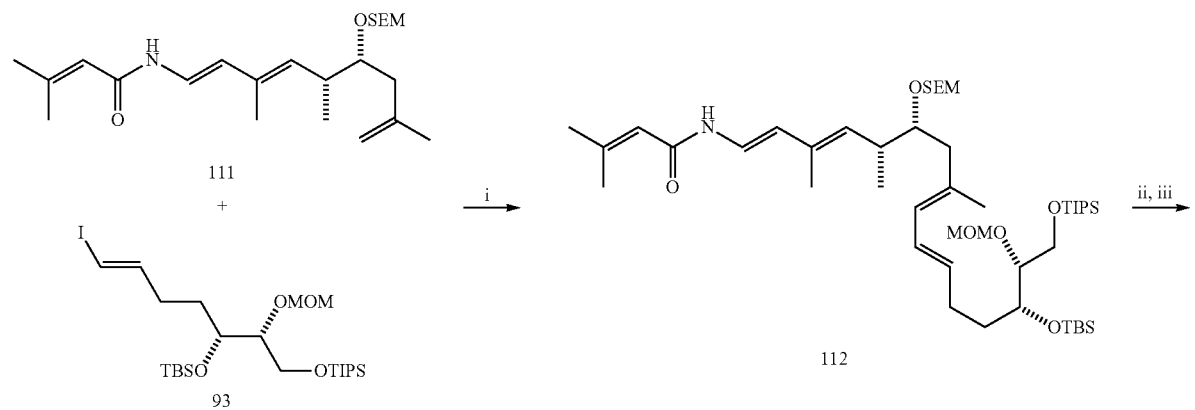

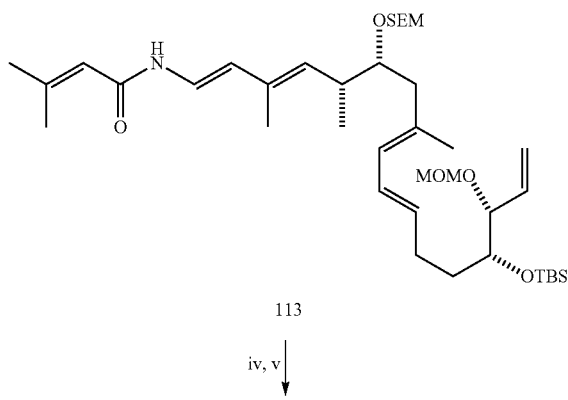

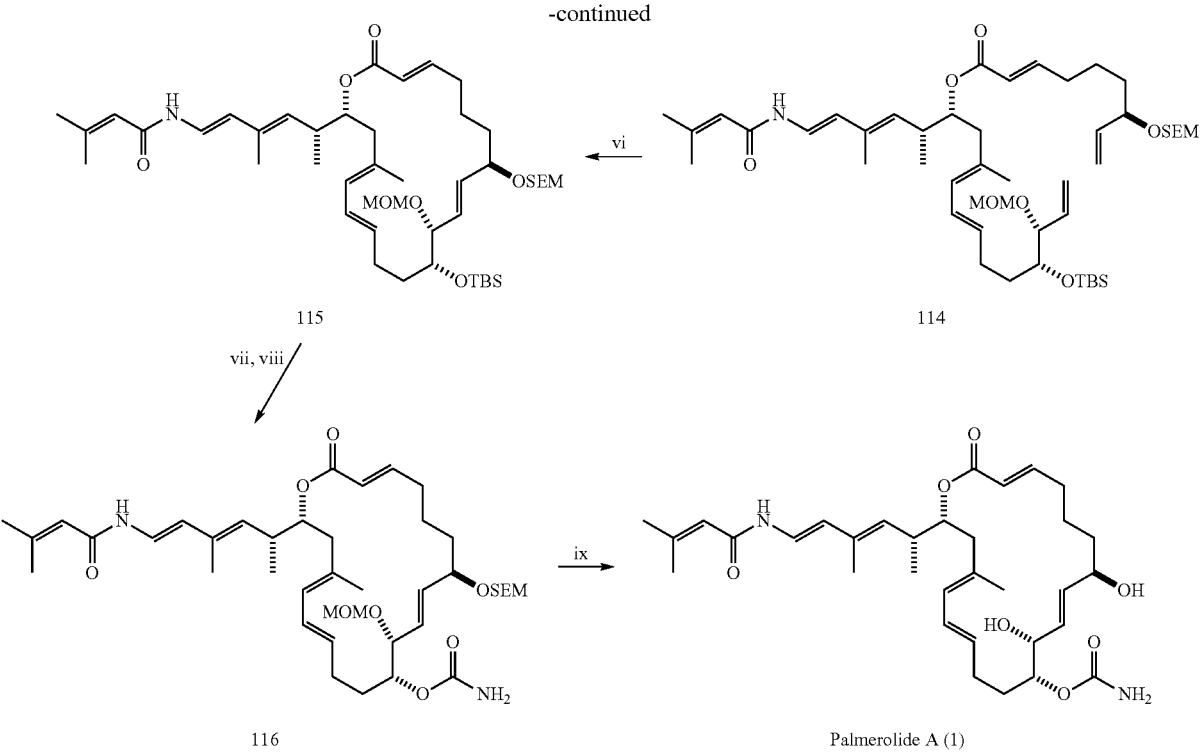

i) Pd(PPh₃)₄, Et₃N, DMF. ii) 40% KOH, MeOH, reflux. iii) Cp₂Ti(Me₂), Toluene. iv) TFA, DCM, 0° C. v) NaH, DMF, 101. vi) Grubb's second generation catalyst, Toluene, Δ. vii) AcOH, H₂O, THF. viii) HNCO, CuCl, DMF. ix) MgBr₂, Et₂O, BuSH, rt.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 6,750,247
U.S. Pat. No. 6,960,648
U.S. Patent Application No. 20030032594
Diyabalanage, T. K.; Amsler, C. D.; McClintock, J. B.; Baker, B. J. (2006) "Palmerolide A, a cytotoxic macrolide from the Antarctic tunicate *Synoicum adareanum. J. Am. Chem. Soc.*, 128, 5630-5631.
Sun-Wadaa, G. H.; Y. Wadaa; M. Futa (2004) "Diverse and essential roles of mammalian vacuolar-type proton pump ATPase: toward the physiological understanding of inside acidic compartments" *Biochim. Biophys. Acta* 1658:106-114.
Nishi, T.; M. Forgac (2002) "The vacuolar (H⁺)-ATPases— Nature's most versatile proton pumps" *Nat. Rev. Mol. Cell. Biol.* 3: 94-103.
Morel, N.; J. C. Dediu; J.- M. Philippe (2003) "Specific sorting of the al isoform of the V—H⁺ ATPase a subunit to nerve terminals where it associates with both synaptic vesicles and the presynaptic plasma membrane" *J. Cell Sci.* 116:4751-4762.
Nomiyama, H.; K. Egami; N. Wada; K. Tou; M. Horiuchi (2005) "Identification of genes differentially expressed in osteoclast-like cells" *J. Interferon Cyto. Res.* 25:227-231.
Martinez-Zaguilan, R.; R. M. Lynch; G. M. Martinez; R. J. Gillies (1993) "Vacuolar-type H⁺-ATPases are functionally expressed in plasma membranes of human tumor cells" *Am. J. Physiol. Cell Physiol.* 265:C1015-C1029.
Martinez-Zaguilan, R. (1999a) "Angiostatin's partners" Science 284:433-434.
Laurencot, C. M.; P. A. Andrews; K. A. Kennedy (1995) "Inhibitors of intracellular pH regulation induce cisplatin resistance in EMT6 mouse mammary tumor cells" *Oncol. Res.* 7:363-369.
Raghunand, N.; R. Martinez-Zaguilan; S. Wright; R. J. Gillies (1999) "pH and drug resistance. II. Turnover of acidic vesicles and resistance to weakly basic chermotherapeutic drugs" *Biochem. Pharmacol.* 57: 1047-1058.
Martinez-Zaguilan, R.; N. Raghunand; R. M. Lynch; W. Bellamy; G. M. Martinez; B. Rojas; D. Smith; W. S. Dalton; R. J. Gillies (1999b) "pH and drug resistance. I. Functional expression of plasmalemmal V-type H⁺-ATPase in drug-resistant human breast carcinoma cell lines" *Biochem. Pharmacol.* 57:1037-1046.
Sennoune, S. R.; D. F. Luo; R. Martinez-Zaguilan (2004) "Plasmalemmal vacuolar-type H⁺-ATPase in cancer biology" *Cell Biochem. Biophys.* 40:185-206.
Martinez-Zaguilan, R.; G. M. Martinez; A. Gomez; M. J. Hendrix; R. J. Gillies (1998) "Distinct regulation of pH$^{in}$ and [CA²⁺]$^{in}$ in human melanoma cells with different metastatic potential" *J. Cell Physiol.* 176:196-205.
Jones, R. P. O.; I. E. Hunt; J. Jaeger; A. Ward; J. O'Reilly; E. A. Barratt; J. B. C. Findlay; M. A. Harrison (2001) "Expression, purification and secondary structure analysis of *Saccharomyces cerevisiae* vacuolar H⁺-ATPase subunit F (VMA7p)" *Mol. Membrane. Biol.* 18:283-290.

Murata, T.; I. Yamato; Y. Kakinuma; A. G. W. Leslie; J. E. Walker (2005) "Structure of the rotor of the V-type Na+-ATPase from *Enterococcus hirae*" *Science* 308: 654-659.

Páli, T., G. Whyteside, N. Nixon, T. P. Kee, S. Ball, M. A. Harrison, J. B. C. Findlay, M. E. Finbow, D. Marsh (2004) "Interaction of inhibitors of the vacuolar H+-ATPase with the transmembrane $V_o$-sector" *Biochem.* 43:12297-12305.

Huss, M., G. Ingenhorst, S. König, M. Gaβel, S. Dröse, A. Zeeck, K. Altendorf, H. Wieczorek (2002) "Concanamycin A, the specific inhibitor of V-ATPases, binds to the $V_o$ subunit c" *J. Biol. Chem.* 277: 40544-40548.

Myers, M. A., I. R. Mackay, P. Z. Zimmet (2003) "Toxic type 1 diabetes" *Rev. Endo. Metab. Disord.* 4:225-231.

Myers, M. A., K. D. Hettiarachchi, J. P. Ludeman, A. J. Wilson, C. R. Wilson, P. Z. Zimmet (2003) "Dietary microbial toxins and type 1 diabetes" *Ann. N.Y. Acad. Sci.* 1005: 418-422.

Sundquist, K., P. Lakkakorpie, B. Wallmark, K. Vaananen (1990) "Inhibition of osteoclast proton transport by bafilomycin A1 abolishes bone resorption" *Biochem. Biophys. Res. Commun.* 168:309-313.

Ellegaard, J., H. Traunberg, V. Esmann (1975) "Elevated lymphocyte ATP-ase activity in patients with cancer of the uterine cervix" *Acta Obstet. Gynecol. Scand.* 54:223-226.

Zhang, J., Y. Feng, M. Forgac (1994) "Proton conduction and bafilomycin binding by the $V_0$ domain of the coated besical V-ATPase" *J. Biol. Chem.* 269:23518-23523.

Erickson, K. L., J. A. Beutler, J. H. Cardellina, M. R. Boyd (1997) "Salicylihalamides A and B, novel cytotoxic macrolides from the marine sponge *Haliclona* sp." *J. Org. Chem.* 62:8188-8192.

Boyd, M. R., C. Farina, P. Belfiore, S. Gagliardi, J. S. Kim, Y. Hayakawa, J. A. Beutler, T. C. McKee, B. J. Bowman, E. J. Bowman (2001) "Discovery of a novel antitumor benzolactone enamide class that selectively inhibits mammalian vacuolar-type (H+)-ATPases" *J. Pharmacol. Exp. Ther.* 297:114-120.

Kim, J. W., K. Shin-ya, K. Furihata, Y. Hayakawa, H. Seto (1999) "Oximidines I and II: Novel antitumor macrolides from *Pseudomonas* sp." *J. Org. Chem.* 64:153-155.

McKee, T. C., D. L. Galinis, L. K. Pannell, J. H. Cardellina, J. Laakso, C. M. Ireland, L. Murray, R. Capon, M. R. Boyd (1998) "The lobatamides, novel cytotoxic macrolides from southwestern Pacific tunicates" *J. Org. Chem.* 63:7805-7810.

Shen, R., C. T. Lin, E. J. Bowman, B. J. Bowman, J. A. Porco, Jr. (2002) "Synthesis and V-ATPase inhibition of simplified lobatamide analogues" *Org. Lett.* 4:3103-3106.

Bowman, E. J., K. R. Gustafson, B. J. Bowman, M. R. Boyd (2003) "Identification of a new chondropsin class of antitumor compound that selectively inhibits V-ATPases" *J. Biol. Chem.* 278:44147-44152.

Bowman, E. J., L. A. Graham, T. H. Stevens, B. J. Bowman (2004) "The bafilomycin/concanamycin binding site in subunit c of the V-ATPases from *Neurospora crassa* and *Saccharomyces cerevisiae*" *J. Biol. Chem.* 279:33131-33138.

Xie, X.-S., D. Padron, X. Liao, J. Wang, M. G. Roth, J. K. De Brabander (2004) "Salicylihalamide A inhibits the $V_0$ sector of the V-ATPase through a mechanism distinct from bafilomycin $A_1$" *J. Biol. Chem.* 279:19755-19763.

Chene, P. (2003) "The ATPases: a new family for a family-based drug design approach" *Expert Opin. Thera. Tar.* 7:453-461.

Beutler, J. A., T. C. McKee (2003) "Novel marine and microbial natural product inhibitors of vacuolar ATPase" *Curr. Med. Chem.* 10:787-796.

Horowitz, S. B. (2004) "Personal recollections of the early development of taxol" *J. Nat. Prod.* 67:136-138.

Arts, J., S. de Shepper, K. Van Emelen (2003) "Histone deacetylase inhibitors: from chromatin remodeling to experimental cancer therapeutics" *Curr. Med. Chem.* 10:2342-2350.

Ohtani, I., T. Kusumi, Y. Kashman, H. Kakisawa (1991) "High-field FT NMR application of Mosher's method. The absolute configurations of marine terpenoids" *J. Am. Chem. Soc.* 113:4092-4096.

Murata, M., S. Matsuoka, N. Matsumori, G. K. Paul, K. Tahibana (1999) "Absolute configuration of Amphidinol 3, the first complete structure determination from amphidinol homologues: Application of a new configuration analysis based on carbon-hydrogen spin-coupling constants" *J. Am. Chem. Soc.* 121:870-871.

Foucault, A. P., P. Durand, E. Camacho-Frias, F. Le Goffic (1993) "Biphasic mixture of water, dimethyl sulfoxide, and tetrahydrofuran for use in centrifugal partition chromatography" *Anal. Chem.* 65:2150-2154.

Amundson, S. A., T. G. Myers, D. Scudiero, S. Katada, J. C. Reed, A. J. Fornace, Jr. (2000) "An informatics approach identifying markers of chemosensitivity in human cancer cell lines" *Cancer Res.* 60:6101-6110.

Lin, J., H. F. Dong, J. J. Oppenheim, O. M. Howard (2003) "Effects of astragali radix on the growth of different cancer cell lines" *World J. Gastroenterol.* 9:670-673.

Miracco, C., E. Maellaro, L. Pacenti, B. De. Bello, M. A. Valentini, P. Rubegin, L. Pirtoli, C. Volpi, R. Santopietro, P. Tosi (2003) "Evaluation of MDR1, LRP, MRP, and topoisomerase IIα gene mRNA transcripts before and after interferon-α, and correlation with the mRNA expression level of the telomerase subunits hTERT and TEP1 in five unselected human melanoma cell lines" *Int. J. Oncol.* 23:213-220.

Vogt, A, E. N. Kalb, J. S. Lazo (2004) "A scalable high-content cytotoxicity assay insensitive to changes in mitochondrial metabolic activity" *Oncol. Res.* 14:305-314.

Balimane, P. V., Y.- H Han, S. Chong (2006) "Current industrial practices of assessing permeability and P-glycoprotein interaction" *AAPS J.* 8:E1-E-13.

De Bruijn, J., Busser, F., Seiner, W., Hermens, J. (1989) "Determination of octanol/water partition coefficients for hydrophobic organic chemicals with the 'slow-stirring' method" *Environ. Toxicol. Chem.* 8:449-512.

Blunt, J. W., Munro, M. H. G. (2004) Marin Lit., University of Canterbury, Christchurch, New Zealand, ver 12.4.

Crews, P., Rodriguez, J., Jaspars, M. (1998) "Organic structure analysis" New York: Oxford University Press, p. 552.

Silverstein, R. M., Webster, F. X. (1998) "Spectrometric identification of organic compounds" $6^{th}$ ed., New York: J. Wiley, p. 482.

Aue, W. P., Bartholdi, E., Ernst, R. R. (1976) "Two-dimensional spectroscopy. Application to nuclear magnetic resonance" *J. Chem. Phys.* 64:2229-2246.

Braunschweiler, L., Ernst, R. R. (1983) "Coherence transfer by isotropic mixing: application to proton correlation spectroscopy" *J. Mag. Res.* 53:521-528.

Bax, A., Subramanian, S. (1986a) "Improved resolution and sensitivity in $^1$H detected heteronuclear multiple-bond correlation spectroscopy" *J. Mag. Res.* 78:186-191.

Bodenhausen, G., Ruben, D. J. (1980) "Natural abundance nitrogen-15 NMR by enhanced heteronuclear spectroscopy" *Chem. Phys. Lett.* 69:185-189.

Bax, A., Summers, M. (1986b) "$^1$H and $^{13}$C Assignments from sensitivity-enhanced detection of heteronuclear multiple-bond connectivity by 2D multiple quantum NMR" *J. Am. Chem. Soc.* 108:2093-2094.

Maudsley, A. A., Wokaun, A., Ernst, R. R. (1978) "Coherence transfer echoes" *Chem. Phys. Lett.* 55:9-14.

Ruiz-Cabello, J., Vuister, G. W., Moonen, C. T. W., van Gelderen, P., Cohen, J. S., van Zijl, P. C. M. (1992) "Gradient-enhanced heteronuclear correlation spectroscopy. Theory and experimental aspects" *J. Mag. Res.* 100:282-302.

Bax, A., Freeman, R., Kempsell, S. P. (1980) "Natural abundance $^{13}$C-$^{13}$C coupling observed via double-quantum coherence" *J. Am. Chem. Soc.* 102:4849-4851.

Griesinger, C., Sorensen, O. W., Ernst, R. R. (1985) "Two-dimensional correlation of connected NMR transitions" *J. Am. Chem. Soc.* 107:6394-6396.

Furihata, K., Seto, H. J. (1999) "Resolved HMBC, a new NMR technique for measuring heteronuclear long-range coupling constants" *Tetrahedron Lett.* 40:6271-6275.

Yoshida, W., Bryan, P., Baker, B. J., McClintock, J. B. (1995) "Pteroenone, the feeding deterrent substance from the Antarctic pteropod *Clione antarctica*" *J. Org. Chem.* 60:780-782.

Ankisetty, S., Nandiraju, S., Win, H., Park, Y. C., Amsler, C. D., McClintock, J. B., Baker, J. A., Diyabalanage, T. K., Pasaribu, A., Singh, M. P., Maiese, W. M., Walsh, R. D., Zaworotko, M. J., Baker, B. J. (2004) "Chemical Investigation of Predator-Deterred Macroalgae from the Antarctic Peninsula" *J. Nat. Prod.* 67:1295-1302.

Wu, Y., Esser, L., De Brabander, J. K. (2000) "Revision of the absolute configuration of salicylihalamide A through asymmetric total synthesis" *Angew. Chem. Int. Ed.* 39:4308-4310.

Hoye, T. R., Mayer, M. J., Vos, T. J., Ye, Z. (1998) "A general, practical, and versatile strategy for accessing ω-functional 1,2-diols of high enantiomeric excess" *J. Org. Chem.* 63:8554-8557.

Zhu, Q., Qiao, L., Wu, Y., Wu, Y.- L. (2001) "Studies toward the total synthesis of clavulactlone" *J. Org. Chem.* 66:2692-2699.

Dolder, M., Xie, S., Tamm, C. (1990) "Synthetic studies directed toward the pseurotins. I. Synthesis of related furan-3(2H)-ones" *Helv. Chem. Acta* 73:63-68.

Ohi, H., Inoue, S., Iwabuchi, Y., Irie, H., Hatakeyama, S. (1999) "Efficient route to functionalized eight-membered lactones based on intramolecular silicon-directed acylative ring-opening reactions of (tetrahydro-2-furyl)propanoic acid derivatives" *Synlett* 1757-1759.

Mancuso, A. J., Swern, D. (1981) "Activated dimethyl sulfoxide: useful reagents for synthesis" *Synthesis* 165-185.

Brunner, H., Lautenschlager, H.- H. (1989) "Synthesis of new optically active bis- and tris(phosphines)" *Synthesis* 706-709.

Larcheveque, M., Lalande, J. (1984) "Synthese enantiospecifique du 5-hexadecanolide, pheromone de 'Vespa Orientalis'" *Tetrahedron* 40:1061-1065.

Lipinski, C. A., Lombardo, F., Dominy, B. W., Feeney, P. J. (2001) "Experimental and computational approaches to estimate solubility and permeability in drug discovery and development setting" *Adv. Drug Delev. Rev.* 46:3-26.

Shen, R., Porco, Jr., J. A. (2000) "Synthesis of enamides related to the salicylate antitumor macrolides using copper-mediated vinylic substitution" *Org. Lett.* 2:1333-1336.

Talkai, K., Nitta, K., Utimoto, K. (1986) "Simple and selective method for RCHO→(E)-RCH=CHX conversion by means of a CHX$_3$—CrCl$_2$ system" *J. Am. Chem. Soc.* 108:7408-7410

Gunasekera, S. P., Gunasekera, M., Longley, R. E., Schulte, G. K. (1990) "Discodermolide: a new bioactive polyhydroxylated lactone from the marine sponge *Discoderma dissoluta*" *J. Org. Chem.* 55:4912-4915.

Paterson, I., Florence, G. J., Gerlach, K., Scott, J. P., Sereinig, N. (2001) "A practical synthesis of (+)-discodermolide and analogues: Fragment union by complex aldol reactions" *J. Am. Chem. Soc.* 123:9535-9544.

Smith, III, A. B., Beauchamp, T. J., LaMarche, M. J., Kaufman, M. D., Qiu, Y., Arimoto, H., Jones, D. R., Kobayashi, K. (2000) "Evolution of a gram-scale synthesis of (+)-discodermolide" *J. Am. Chem. Soc.* 122:8654-8664.

Eaton, J. T., Rounds, W. D., Urbanowicz, J. H., Gribble, G. W. (1988) "Hydrolysis in the absence of bulk water 1. Chemoselective hydrolysis of amides using tetrahalophthalic anhydrides" *Tetrahedron Lett.* 29:6553-6556.

Di Grandi, M. J., Jug, D. K., Krol, W. J., Danishefsky, S. J. (1993) "Synthesis of competent nucleophiles for delivering the A ring of taxol" *J. Org. Chem.* 58:4989-4992.

Nakajima, N., Horita, K., Abe, R., Yonemitsu, O. (1988) "MPM (4-methoxybenzyl) protection of hydroxy functions under mild acidic conditions" *Tetrahedron Lett.* 29:4139-4142.

Dess, D. B., Martin, J. C. (1991) "A useful 12-I-5 triacetoxyperiodinane (the Dess-Martin periodinane) for the selective oxidation of primary or secondary alcohols and a variety of related 12-I-5 species" *J. Am. Chem. Soc.* 113:7277.

Brink, G.- J., Arends, I. W. C. E., Sheldon, R. A. (2004) "The Baeyer-Villiger reaction: New developments toward greener procedures" *Chem. Rev.* 104:4105-4123.

Kocovsky, P. (1986) "Carbamates: A method of synthesis and some synthetic applications" *Tetrahedron Lett.* 27:5521-5524.

Guglielmo, B. J., MacDougall, C. (2004) "Pharmacokinetics of valaciclovir" *J. Antimicrob. Chemother.* 53:899-901.

Choi, J., Yoon, N. M. (1996) "An excellent nickel boride catalyst for the selective hydrogenation of olefins" 597-599.

Ram, S., Spicer, L. D. (1992) "Catalyst type and concentration dependence in catalytic transfer hydrogenolysis of α,β-unsaturated carbonyls and nitrites via ammonium formate" *Synth. Comm.* 22:2683-2690.

Yoon, N. M. (1996) "Selective reduction of organic compounds with aluminum and boron hydrides" *Pure Appl. Chem.* 68:843-848.

Grubbs, R. H., Miller, S. J., Fu, G. C. (1995) "Ring-closing metathesis and related processes in organic synthesis" *Acc. Chem. Res.* 28:446-452.

Harris, L., Jarowicki, K., Kocienski, P., Bell, R. (1996) "Synthetic approaches to rapamycin. 3. Synthesis of a C1-C21 fragment" *Synlett* 903.

Klapars, A., Antilla, J. C., Huang, X., Buchwald, S. L. (2001) "A general and efficient copper catalyst for the amidation of aryl halides and the N-arylation of nitrogen heterocycles" *J. Am. Chem. Soc.* 123:7727-7729.

Jiang, L., Job, G. E., Klapars, A., Buchwald, S. L. (2003) "Copper catalyzed coupling of amides and carbamates with vinyl halides" *Org. Lett* 5:3667-3669.

Schlosser, M., Christmann, K. F. (1966) "Trans-selective olefin synthesis" *Angew. Chem. Int. Ed. Engl.* 5:126.

Evans, D. A., Bartoli, J., Shih, T. L. (1981) "Enantioselective aldol condensations. 2. Erythro-selective chiral aldol condensations via boron enolates" *J. Am. Chem. Soc.* 103:2127-2109.

Jacobsen, E. N., Marko, I., Mungall, W. S., Schroeder, G., Sharpless, K. B. (1988) "Asymmetric dihydroxylation via ligand accelerated catalysis" *J. Am. Chem. Soc.* 110:1968-1970.

Stocksdale, M. G., Ramurthy, S., Miller, M. J. (1998) "Asymmetric total synthesis of an important 3-(hydroxymethyl) carbocephalosporin" *J. Org. Chem.* 63:1221-1225.

Hanessian, S., Levallee, P. (1975) "Preparation and synthetic utility of tert-butyl diphenylsilyl ethers" *Can. J. Chem.* 53:2975-2977.

Nicolaou, K. C., Prasad, C. V. C., Somers, P. K., Hwang, C.-K. (1989) "Activation of 7-endo over 6-exo epoxide openings. Synthesis of oxepane and tetrahydropyran systems" *J. Am. Chem. Soc.* 111:5335-5340.

Li, G., Chang, J.- T. Sharpless, K. B., (1996) "Catalytic aminohydroxylations (AA) of olefins," *Angew Chem. Int. Ed. Engl.*, 35:451-454.

Coe, J. W., Roush, W. R. (1989) "Studies of an intramolecular Diels-Adler approach to the nargenicins; involvement of boat-like transition states in the cyclizations of substituted 1,7,9-decatrien-3-ones" *J. Org. Chem.* 54:915-930.

Cunico, R. F., Bedell, L. (1980) "The triissopropylsilyl group as a hydroxyl-protecting function" *J. Org. Chem.* 45:4797-4798.

Kim, K. S., Song, Y. H. Lee, B. H., Hahn, E. S. (1986) "Efficient and selective cleavage of acetals and ketals using ferric chloride adsorbed on silica gel" *J. Org. Chem.* 51:404-407.

Corey, E. J., Venkateswarlu, A. (1972) "Protection of hydroxyl groups as tert-butyldimethylsilyl derivatives" *J. Am. Chem. Soc.* 94:6190-6191.

Kluge, A. F., Untch, K. G., Fried, J. H. (1972) "Synthesis of prostaglandin models and prostaglandins by conjugate addition of a functionalized organocopper reagent," *J. Am. Chem. Soc.* 94:7827-7832.

Dess, D. B., Martin, J. C. (1983) "Readily accessible 12-I-5 oxidant for the conversion of primary and secondary alcohols to aldehydes and ketones" *J. Org. Chem.* 48:4155-4156.

Lipshutz, B. H., Pegram, J. J. (1980) "Beta-(trimethylsilyl) ethoxymethyl chloride—a new reagent for the protection of the hydroxyl group" *Tetrahedron Lett.* 21:1935-1939.

Petassis, N. A., Bzowej, E. I. (1990) "Titanium-mediated carbonyl oldfinations. 1. Methylenations of carbonyl compounds with dimethyltitanocene" *J. Am. Chem. Soc.* 12:6392-6394.

Sunazuka, T., Hirose, T., Shirahata, T., Harigayam Y., Hayashi, M., Komuyama, K., Omura, S., Smith, III, A. B. (2000) "Total synthesis of (+)-madindoline A, and (-)-mandinoline B, potent, selective inhibitors of interleukin 6. Determination of the relative and absolute configurations" *J. Am. Chem. Soc.* 122:2122-2123.

Bowden, K., Heilbron, I. M., Jones, E. R. H., Weedon, B. C. L. (1946) "Acetylenic compounds. I. Preparation of acetylenic ketones by oxidation of acetylenic carbinols and glycols" *J. Chem. Soc.* 39-45.

Reiter, B., Burger, B. V., Dry, J. (2003) "Mammalian exocrine secretions. XVIII: Chemical characterization of interdigital secretion of red hartebeest, *Alcelaphus buselophus caoma*" *J. Chem. Ecol.* 29:2235-2252.

Wiley, G. A., Hershkowitz, R. L., Rein, B. M., Chung, B. C. (1964) "Studies in organophosphorns chemistry. I. Conversion of alcohols to halides by tertiary phosphine dihaldes" *J. Am. Chem. Soc.* 86:964-965.

Hagiwara, H., Uda, H., (1987) "A total synthesis of (+)-Perrottetianal-A" *J. Chem. Soc. Chem. Comm.* 1351-1353.

Schlessinger, R. H., Poss, M. A., Richardson, S. (1986) "Total synthesis of (+)-Rosaramicin aglycone and its diacetate" *J. Am. Chem. Soc.* 108:3112.

Meng, D., Bertinato, P., Balog, A., Su, D-S., Kanmenecka, T., Sorensen, E. J., Danishefsky, S. J. (1997) "Total synthesis of epothilones A and B" *J. Am. Chem. Soc.* 119:10073-10092.

Duggan, M. E., Imagire, J. S. (1989) "Copper(I) chloride catalyzed addition of alcohols to alkyl isocyanates. A mild and expedient method for alkyl carbamate formation" *Synthesis* 131-132.

Kim, S., Kee I. S., Park, Y. H., Park, J. H. (1991) "Selective cleavage of acetal-type ethers with magnesium bromide and butyl mercaptan in diethyl-ether" *Synlett* 183-184.

We claim:

1. An isolated Palmerolide compound of formula I:

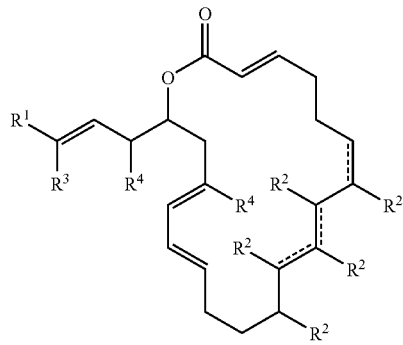

wherein:

===== = single or double bond $R^1$ is carboxaldehyde, —CHCHNHC(O)-Alkyl, —OC-Alkyl, —OC-aryl, —OC-amino, aryl, amino, -vinylamido, arylamido, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, a halogen, or —CHO, any of which can be optionally substituted with H, alkyl, alkoxy, —OH, —$NO_2$, —$NH_2$, —COON, a halogen, or —$CH_3$;

$R^2$ is, independently, OH, O-Acyl, carbamate, H, O-alkyl, amino, —OC($NH_2$)O, —$OSO_3H$, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, a halogen, or oxo, wherein at least one $R^2$ is —OC($NH_2$)O or —$OSO_3H$;

$R^3$ is H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, halogen, any of which can be optionally substituted with alkyl, alkoxy, —OH, —$NO_2$, —$NH_2$, —COOH, a halogen, or —$CH_3$;

$R^4$ is, independently, H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, halogen, any of which can be optionally substituted with alkyl, alkoxy, —OH, —$NO_2$, —$NH_2$, —COOH, a halogen, or —$CH_3$;

or a stereoisomer or a pharmaceutically acceptable salt thereof; wherein said compound does not have the structure:

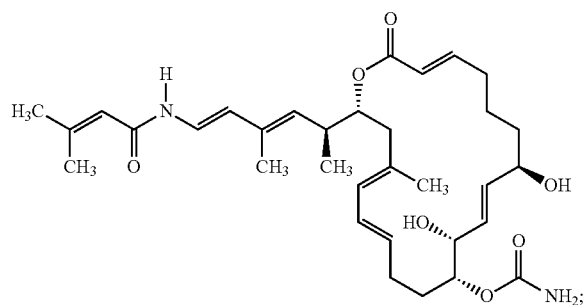

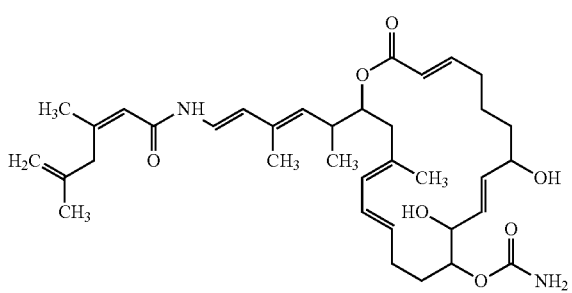

or;

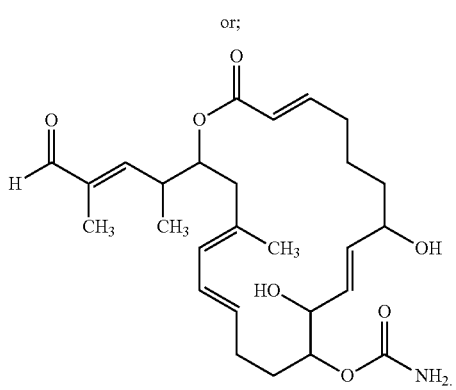

2. The Palmerolide compound according to claim 1, wherein at least one $R^2$ is —OC(NH$_2$)O.

3. The Palmerolide compound according to claim 1, wherein $R^3$ is methyl.

4. The Palmerolide compound according to claim 1, wherein at least one $R^4$ is methyl.

5. The Palmerolide compound according to claim 1, wherein $R^1$ is —CHCHNHC(O)CHC(CH$_3$)$_2$.

6. The Palmerolide compound according to claim 1, wherein $R^1$ is —CHCHNHC(O)CHC(CH$_3$)CH$_2$C(CH$_3$)CH$_2$.

7. The Palmerolide compound according to claim 1, wherein $R^1$ is —CHCH—NHC(O)CH$_2$C(CH$_3$)CH$_2$.

8. The Palmerolide compound according to claim 1, wherein $R^1$ is —CH=O.

9. The Palmerolide compound according to claim 1, wherein at least one $R^2$ is —OH.

10. The Palmerolide compound according to claim 1, wherein at least one $R^2$ is —OSO$_3$H.

11. The Palmerolide compound according to claim 1, wherein at least two $R^2$ are —OH and at least one $R^2$ is —OC(NH$_2$)O, and optionally $R^3$ and $R^4$ are —CH$_3$.

12. The Palmerolide compound according to claim 1, wherein said compound has the structure:

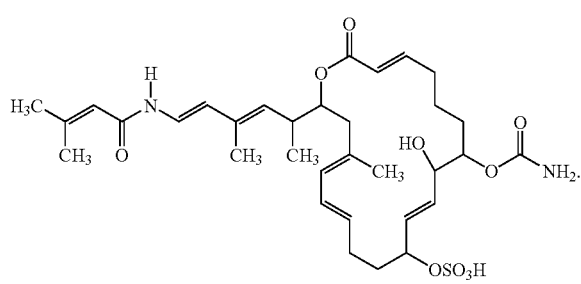

13. The Palmerolide compound according to claim 1, wherein said compound has the structure:

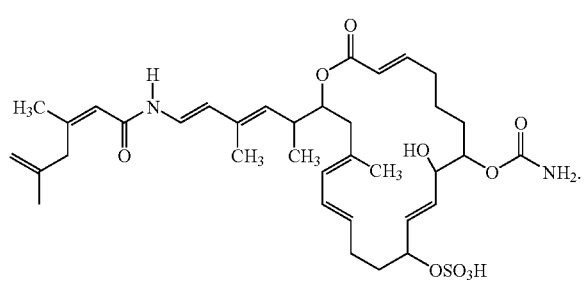

14. The Palmerolide compound according to claim 1, wherein both $R^4$ are methyl.

15. An isolated Palmerolide compound of formula II:

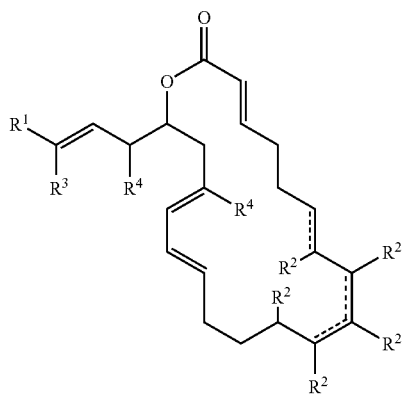

wherein:
===== =single or double bond
$R^1$ is carboxaldehyde, —CHCHNHC(O)-Alkyl, —OC-Alkyl, —OC-aryl, —OC-amino, aryl, amino, -vinylamido, arylamido, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, a halogen, or —CHO, any of which can be optionally substituted with H, alkyl, alkoxy, —OH, —NO$_2$, —NH$_2$, —CO OH, a halogen, or —CH$_3$;

$R^2$ is, independently, OH, O-Acyl, carbamate, H, O-alkyl, amino, —OSO$_3$H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, a halogen, or oxo;

$R^3$ is H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, halogen, any of which can be optionally substituted with alkyl, alkoxy, —OH, —NO$_2$, —NH$_2$, —COOH, a halogen, or —CH$_3$;

$R^4$ is, independently, H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, halogen, any of which can be optionally substituted with alkyl, alkoxy, —OH, —NO$_2$, —NH$_2$, —COOH, a halogen, or —CH$_3$;

or a stereoisomer or a pharmaceutically acceptable salt thereof; wherein said compound does not have the structure:

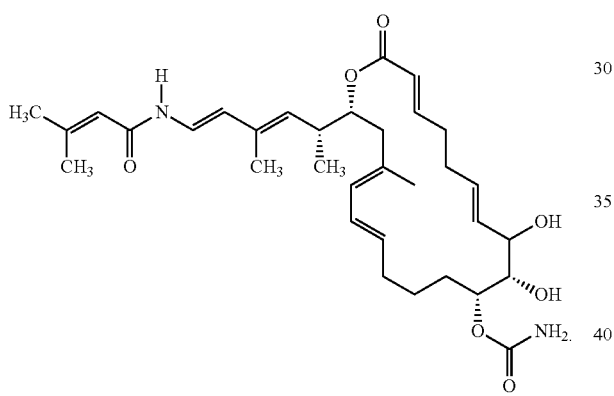

16. The Palmerolide compound according to claim 15, wherein at least one $R^2$ is —OC(NH$_2$)O.

17. The Palmerolide compound according to claim 15, wherein $R^3$ is methyl.

18. The Palmerolide compound according to claim 15, wherein at least one $R^4$ is methyl.

19. The Palmerolide compound according to claim 15, wherein $R^1$ is —CHCHNHC(O)CHC(CH$_3$)$_2$.

20. The Palmerolide compound according to claim 15, wherein $R^1$ is —CHCHNHC(O)CHC(CH$_3$)CH$_2$C(CH$_3$)CH$_2$.

21. The Palmerolide compound according to claim 15, wherein $R^1$ is —CHCH—NHC(O)CH$_2$C(CH$_3$)CH$_2$.

22. The Palmerolide compound according to claim 15, wherein $R^1$ is —CH=O.

23. The Palmerolide compound according to claim 15, wherein at least one $R^2$ is —OH.

24. The Palmerolide compound according to claim 15, wherein at least one $R^2$ is —OSO$_3$H.

25. The Palmerolide compound according to claim 15, wherein at least two $R^2$ are —OH and at least one $R^2$ is —OC(NH$_2$)O, and optionally $R^3$ and $R^4$ are —CH$_3$.

26. The Palmerolide compound according to claim 15, wherein said compound has the structure:

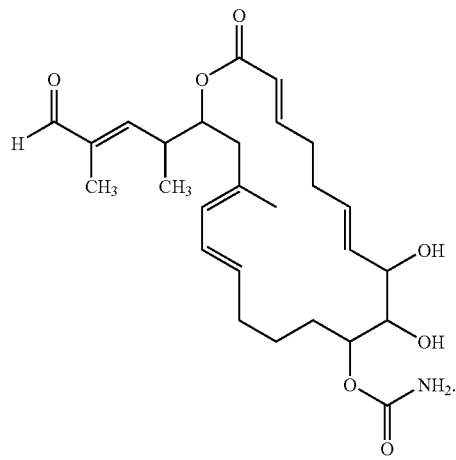 [SMILES: C/C(C=O)=C\C(C)C1C/C(C)=C/C=C/CCCC(OC(N)=O)C(O)C(O)/C=C/CC/C=C/C(=O)O1]

27. The Palmerolide compound according to claim 15, wherein both $R^4$ are methyl.

28. A composition comprising a pharmaceutically acceptable carrier and a Palmerolide compound of any of formula I:

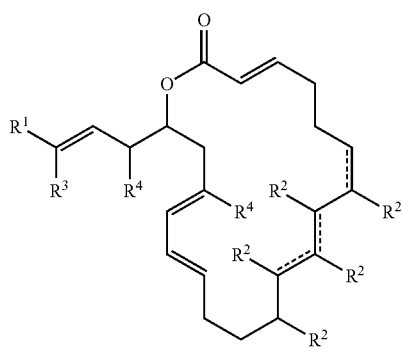

wherein:
===== =single or double bond $R^1$ is carboxaldehyde, —CHCHNHC(O)-Alkyl, —OC-Alkyl, —OC-aryl, —OC-amino, aryl, amino, -vinylamido, arylamido, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, a halogen, or —CHO, any of which can be optionally substituted with H, alkyl, alkoxy, —OH, —NO$_2$, —NH$_2$, —COOH, a halogen, or —CH$_3$;

$R^2$ is, independently, OH, O-Acyl, carbamate, H, O-alkyl, amino, —OC(NH$_2$)O, —OSO$_3$H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, a halogen, or oxo, wherein at least one $R^2$ is —OC(NH$_2$)O or —OSO$_3$H;

$R^3$ is H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, halogen, any of which can be optionally substituted with alkyl, alkoxy, —OH, —NO$_2$, —NH$_2$, —COOH, a halogen, or —CH$_3$;

R$^4$ is, independently, H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, halogen, any of which can be optionally substituted with alkyl, alkoxy, —OH, —NO$_2$, —NH$_2$, —COOH, a halogen, or —CH$_3$;

or a stereoisomer or a pharmaceutically acceptable salt thereof; wherein said compound does not have the structure:

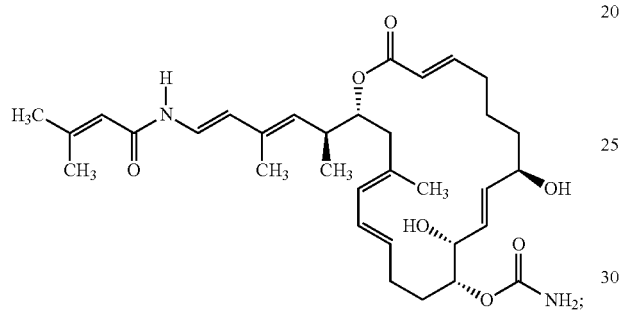

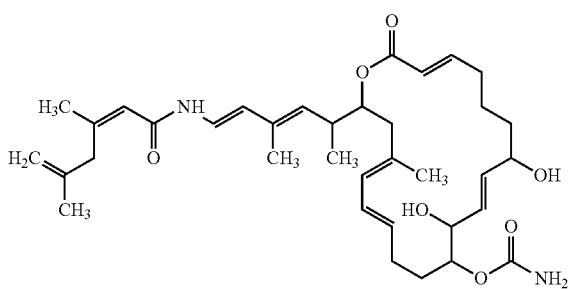

or;

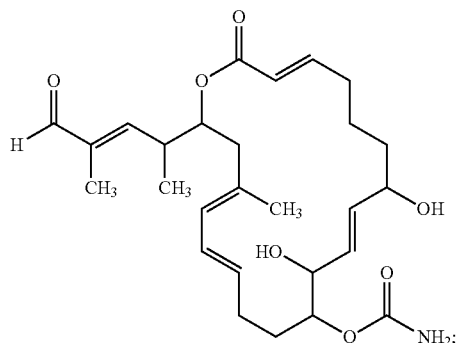

or of formula II:

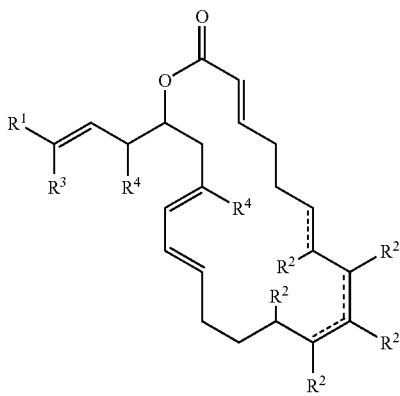

wherein:
===== =single or double bond

R$^1$ is carboxaldehyde, —CHCHNHC(O)-Alkyl, —OC-Alkyl, —OC-aryl, —OC-amino, aryl, amino, -vinylamido, arylamido, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, a halogen, or —CHO, any of which can be optionally substituted with H, alkyl, alkoxy, —OH, —NO$_2$, —NH$_2$, —COON, a halogen, or —CH$_3$;

R$^2$ is, independently, OH, O-Acyl, carbamate, H, O-alkyl, amino, —OSO$_3$H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, a halogen, or oxo;

R$^3$ is H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, halogen, any of which can be optionally substituted with alkyl, alkoxy, —OH, —NO$_2$, —NH$_2$, —COOH, a halogen, or —CH$_3$;

R$^4$ is, independently, H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, halogen, any of which can be optionally substituted with alkyl, alkoxy, —OH, —NO$_2$, —NH$_2$, —COOH, a halogen, or —CH$_3$;

or a stereoisomer or a pharmaceutically acceptable salt thereof; wherein said compound does not have the structure:

29. The composition according to claim 28, wherein at least one $R^2$ is —OC(NH$_2$)O.

30. The composition according to claim 28, wherein $R^3$ is methyl.

31. The composition according to claim 28, wherein at least one $R^4$ is methyl.

32. The composition according to claim 28, wherein $R^1$ is —CHCHNHC(O)CHC(CH$_3$)$_2$.

33. The composition according to claim 28, wherein $R^1$ is —CHCHNHC(O)CHC(CH$_3$)CH$_2$C(CH$_3$)CH$_2$.

34. The composition according to claim 28, wherein $R^1$ is —CHCH—NHC(O)CH$_2$C(CH$_3$)CH$_2$.

35. The composition according to claim 28, wherein $R^1$ is —CH=O.

36. The composition according to claim 28, wherein at least one $R^2$ is —OH.

37. The composition according to claim 28, wherein at least one $R^2$ is —OSO$_3$H.

38. The composition according to claim 28, wherein at least two $R^2$ are —OH and at least one $R^2$ is —OC(NH$_2$)O, and optionally $R^3$ and $R^4$ are —CH$_3$.

39. The composition according to claim 28, wherein said compound has the structure:

40. The composition according to claim 28, wherein said compound has the structure:

41. The composition according to claim 28, wherein said compound has the structure:

42. A kit comprising in one or more containers a Palmerolide of any of formula I:

wherein:
===== = single or double bond
$R^1$ is carboxaldehyde, —CHCHNHC(O)-Alkyl, —OC-Alkyl, —OC-aryl, —OC-amino, aryl, amino, -vinylamido, arylamido, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, a halogen, or —CHO, any of which can be optionally substituted with H, alkyl, alkoxy, —OH, —NO$_2$, —NH$_2$, —COON, a halogen, or —CH$_3$;
$R^2$ is, independently, OH, O-Acyl, carbamate, H, O-alkyl, amino, —OC(NH$_2$)O, —OSO$_3$H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, a halogen, or oxo, wherein at least one $R^2$ is —OC(NH$_2$)O or —OSO$_3$H;
$R^3$ is H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, halogen, any of which can be optionally substituted with alkyl, alkoxy, —OH, —NO$_2$, —NH$_2$, —COOH, a halogen, or —CH$_3$;

R$^4$ is, independently, H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, halogen, any of which can be optionally substituted with alkyl, alkoxy, —OH, —NO$_2$, —NH$_2$, —COOH, a halogen, or —CH$_3$;

or a stereoisomer or a pharmaceutically acceptable salt thereof; wherein said compound does not have the structure:

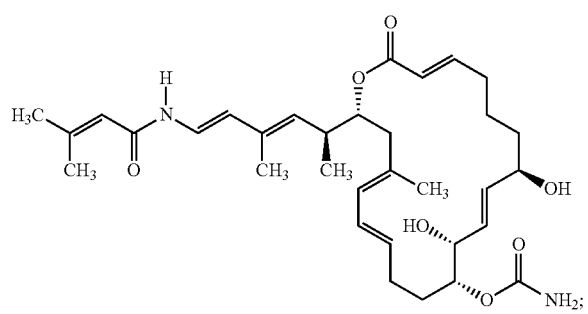

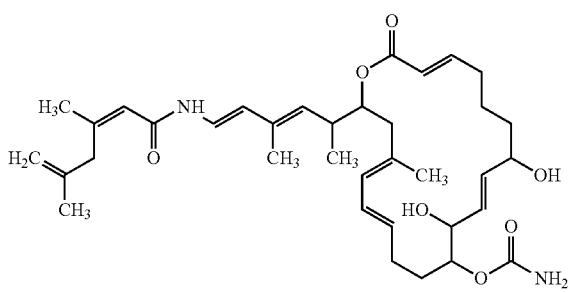

or;

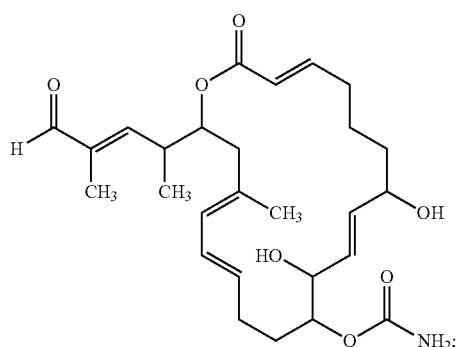

or of formula II:

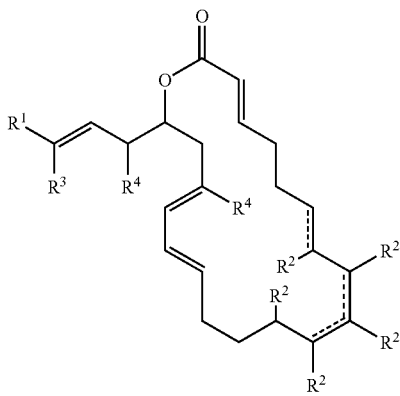

wherein:

===== =single or double bond

R$^1$ is carboxaldehyde, —CHCHNHC(O)-Alkyl, —OC-Alkyl, —OC-aryl, —OC-amino, aryl, amino, -vinylamido, arylamido, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, a halogen, or —CHO, any of which can be optionally substituted with H, alkyl, alkoxy, —OH, —NO$_2$, —NH$_2$, —COOH, a halogen, or —CH$_3$;

R$^2$ is, independently, OH, O-Acyl, carbamate, H, O-alkyl, amino, —OSO$_3$H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, a halogen, or oxo;

R$^3$ is H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, halogen, any of which can be optionally substituted with alkyl, alkoxy, —OH, —NO$_2$, —NH$_2$, —COOH, a halogen, or —CH$_3$;

R$^4$ is, independently, H, alkyl, alkoxy, cycloalkyl, cycloalkoxy, aryloxy, alkylcarbonyl; alkoxycarbonyl, cycloalkylcarbonyl, cycloalkoxycarbonyl, heteroalkyl, heterocycloalkyl, heteroaryl, arylcarbonyl, heteroarycarbonyl, heterocycloalkylcarbonyl, aryloxycarbonyl, heteroaryloxycarbonyl, heterocycloalkoxycarbonyl, halogen, any of which can be optionally substituted with alkyl, alkoxy, —OH, —NO$_2$, —NH$_2$, —COOH, a halogen, or —CH$_3$;

or a stereoisomer or a pharmaceutically acceptable salt thereof; wherein said compound does not have the structure:

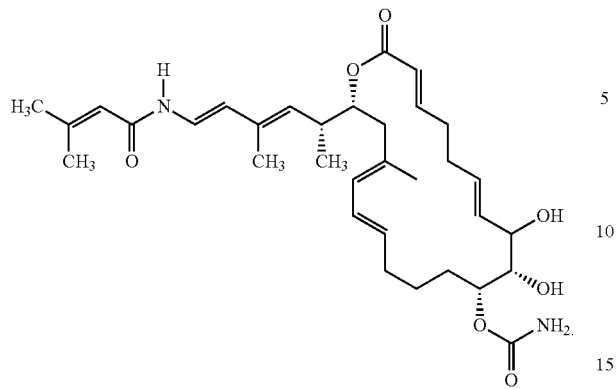

43. The kit according to claim 42, wherein said Palmerolide compound has the structure:

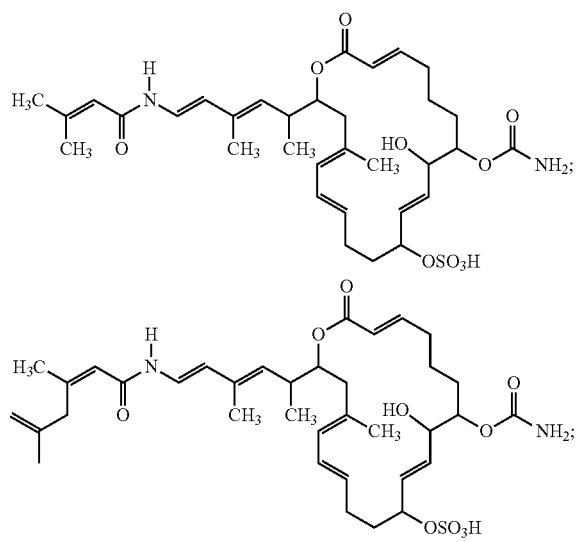

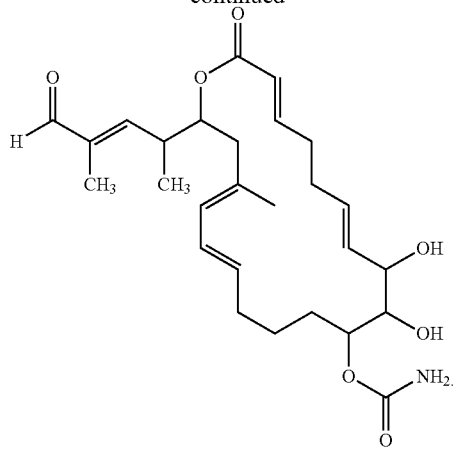

44. The kit according to claim 42, wherein at least one $R^2$ is —OC(NH$_2$)O.

45. The kit according to claim 42, wherein $R^3$ is methyl.

46. The kit according to claim 42, wherein at least one $R^4$ is methyl.

47. The kit according to claim 42, wherein $R^1$ is —CHCH-NHC(O)CHC(CH$_3$)$_2$.

48. The kit according to claim 42, wherein $R^1$ is —CHCH-NHC(O)CHC(CH$_3$)CH$_2$C(CH$_3$)CH$_2$.

49. The kit according to claim 42, wherein $R^1$ is —CHCH—NHC(O)CH$_2$C(CH$_3$)CH$_2$.

50. The kit according to claim 42, wherein $R^1$ is —CH=O.

51. The kit according to claim 42, wherein at least one $R^2$ is —OH.

52. The kit according to claim 42, wherein at least one $R^2$ is —OSO$_3$H.

53. The kit according to claim 42, wherein at least two $R^2$ are —OH and at least one $R^2$ is —OC(NH$_2$)O, and optionally $R^3$ and $R^4$ are —CH$_3$.

54. The kit according to claim 42, wherein both $R^4$ are methyl.

* * * * *

UNITED STATES PATENT AND TRADEMARK OFFICE
CERTIFICATE OF CORRECTION

PATENT NO. : 8,669,376 B2
APPLICATION NO. : 12/066938
DATED : March 11, 2014
INVENTOR(S) : Bill J. Baker et al.

It is certified that error appears in the above-identified patent and that said Letters Patent is hereby corrected as shown below:

In the Specification

Column 1,
Line 56, "Palmerolide E, Palmerolide E" should read --Palmerolide D, Palmerolide E--

Column 2,
Line 37, "cell (lines" should read --cell lines--

Column 8,
Line 62, "Up to X" should read --up to X--

Column 9,
Line 1, "Spiro rings" should read --spiro rings--

Column 20,
Line 8, "at 540 nm n." should read --at 540 nm.--

Column 25,
Line 59, "VI domain" should read --$V_1$ domain--

Column 27,
Line 26, "for ED approval" should read --for IND approval--

Signed and Sealed this
Ninth Day of September, 2014

Michelle K. Lee
*Deputy Director of the United States Patent and Trademark Office*

CERTIFICATE OF CORRECTION (continued)
U.S. Pat. No. 8,669,376 B2

Column 32,

Lines 1-15, " 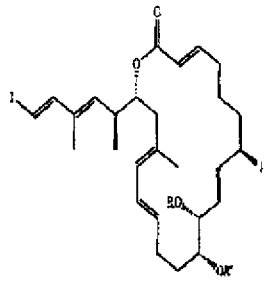 " should read -- 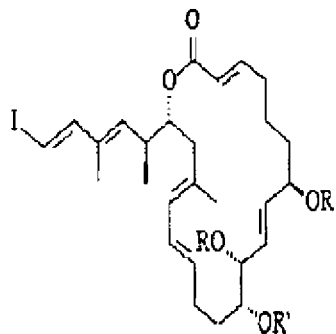 --

Column 49,
Line 55, "Talkai, K." should read --Takai, K.--
Line 60, "Discoderma" should read --Discodermia--

Column 50,
Line 31, "nitrites via" should read --nitriles via--

Column 51,
Line 57, "'Kanmenecka, T." should read --Kamenecka, T.--

In the Claims

Column 52,
Line 35, "-COON, a" should read -- -COOH, a--

Column 58,
Line 36, "-COON, a" should read -- -COOH, a--

Column 60,

Lines 27-41, " 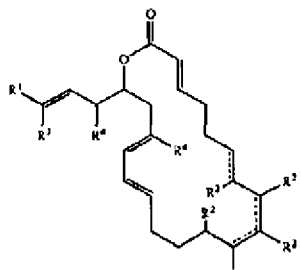 " should read -- 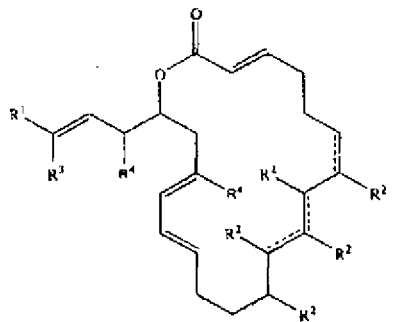 --

Column 60,
Line 55, "-COON, a" should read -- -COOH, a--

UNITED STATES PATENT AND TRADEMARK OFFICE
CERTIFICATE OF CORRECTION

PATENT NO.       : 8,669,376 B2
APPLICATION NO. : 12/066938
DATED            : March 11, 2014
INVENTOR(S)      : Baker et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1476 days.

Signed and Sealed this
Twenty-ninth Day of September, 2015

Michelle K. Lee
*Director of the United States Patent and Trademark Office*